(12) United States Patent
Chen et al.

(10) Patent No.: US 8,377,928 B2
(45) Date of Patent: Feb. 19, 2013

(54) 3-AMINOSULFONYL SUBSTITUTED INDOLE DERIVATIVES AND METHODS OF USE THEREOF

(75) Inventors: Kevin X. Chen, Edison, NJ (US); Stuart B. Rosenblum, West Orange, NJ (US); F. George Njoroge, Warren, NJ (US); Joseph A. Kozlowski, Princeton, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 49 days.

(21) Appl. No.: 12/743,023

(22) PCT Filed: Nov. 13, 2008

(86) PCT No.: PCT/US2008/083358
§ 371 (c)(1),
(2), (4) Date: May 14, 2010

(87) PCT Pub. No.: WO2009/064852
PCT Pub. Date: May 22, 2009

(65) Prior Publication Data
US 2010/0260711 A1    Oct. 14, 2010

Related U.S. Application Data

(60) Provisional application No. 60/988,521, filed on Nov. 16, 2007.

(51) Int. Cl.
*A61K 31/404* (2006.01)
*A61K 31/549* (2006.01)

(52) U.S. Cl. .......... 514/222.5; 514/415; 544/8; 548/483

(58) Field of Classification Search ........ 544/8; 548/483
See application file for complete search history.

(56) References Cited

U.S. PATENT DOCUMENTS

| | | | |
|---|---|---|---|
| 3,632,805 A | 1/1972 | Yamamoto et al. |
| 4,634,697 A | 1/1987 | Hamashima |
| 4,812,561 A | 3/1989 | Hamashima et al. |
| 4,933,443 A | 6/1990 | Hamashima et al. |
| 5,017,380 A | 5/1991 | Hamashima et al. |
| 6,800,434 B2 | 10/2004 | Saksena et al. |
| 6,838,475 B2 | 1/2005 | Arasappan et al. |
| 6,846,802 B2 | 1/2005 | Chen et al. |
| 6,911,428 B2 | 6/2005 | Zhu et al. |
| 6,914,122 B2 | 7/2005 | Venkatraman et al. |
| 7,012,066 B2 | 3/2006 | Saksena et al. |
| 2002/0160962 A1 | 10/2002 | Saksena et al. |
| 2004/0077704 A1 | 4/2004 | Beight et al. |
| 2005/0075331 A1 | 4/2005 | Pratt et al. |
| 2005/0101770 A1 | 5/2005 | Presta |
| 2005/0176648 A1 | 8/2005 | Saksena et al. |
| 2005/0249702 A1 | 11/2005 | Njoroge et al. |
| 2007/0274951 A1 | 11/2007 | Tong et al. |
| 2010/0098661 A1 | 4/2010 | Chen et al. |
| 2010/0196319 A1 | 8/2010 | Anilkumar et al. |
| 2010/0239527 A1 | 9/2010 | Anilkumar et al. |
| 2010/0260711 A1 | 10/2010 | Chen et al. |
| 2010/0322901 A1 | 12/2010 | Bennett et al. |
| 2011/0033417 A1 | 2/2011 | Anilkumar et al. |
| 2011/0104109 A1 | 5/2011 | Bennett et al. |
| 2011/0104110 A1 | 5/2011 | Anikumar et al. |
| 2011/0165118 A1 | 7/2011 | Chan et al. |

FOREIGN PATENT DOCUMENTS

| | | |
|---|---|---|
| AU | 2002313410 B2 | 7/2002 |
| DE | 648639 C | 8/1937 |
| EP | 0449196 A2 | 10/1991 |
| FR | 2768146 A1 | 3/1999 |
| JP | 4-149429 | 5/2004 |
| WO | 96/37619 A1 | 11/1996 |
| WO | 98/14181 A1 | 4/1998 |
| WO | 98/17679 A1 | 4/1998 |
| WO | 98/22496 A2 | 5/1998 |
| WO | 99/07734 A2 | 2/1999 |
| WO | 02/30895 A1 | 4/2002 |
| WO | 02/068412 A1 | 9/2002 |
| WO | 2004/035571 A1 | 4/2004 |
| WO | 2004/106328 A1 | 12/2004 |
| WO | 2005/034941 A1 | 4/2005 |
| WO | 2005/084315 A2 | 9/2005 |
| WO | 2005/087731 A1 | 9/2005 |
| WO | 2005/111018 A1 | 11/2005 |

(Continued)

OTHER PUBLICATIONS

Beaulieu et al., "Inhibitors of the HCV NS5B polymerase: New hope for the treatment of hepatitis C infections", Current Opinion in Investigational Drugs, 2004, vol. 5, pp. 838-850, No. 8.

(Continued)

*Primary Examiner* — Brian McDowell
(74) *Attorney, Agent, or Firm* — Melissa B. Wenk; Sheldon O. Heber

(57) ABSTRACT

The present invention relates to 3-Aminosulfonyl Substituted Indole Derivatives of Formula (I):

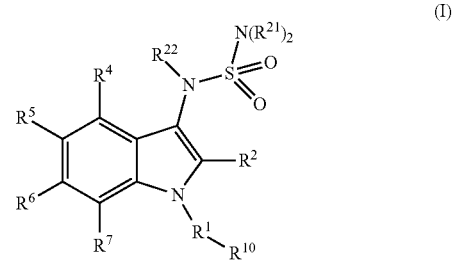

The invention also relates to compositions comprising at least one 3-Aminosulfonyl Substituted Indole Derivative, and methods of using the 3-Aminosulfonyl Substituted Indole Derivatives for treating or preventing a viral infection or a virus-related disorder in a patient.

15 Claims, No Drawings

FOREIGN PATENT DOCUMENTS

| | | |
|---|---|---|
| WO | 2006/020082 A1 | 2/2006 |
| WO | 2006/032541 A1 | 3/2006 |
| WO | 2006/034337 A2 | 3/2006 |
| WO | 2006/046030 A2 | 5/2006 |
| WO | 2006/076529 A1 | 7/2006 |
| WO | 2007/029029 A2 | 3/2007 |
| WO | 2007/038209 A2 | 4/2007 |
| WO | 2007/084413 A2 | 7/2007 |
| WO | 2007/084435 A2 | 7/2007 |
| WO | 2008/082484 A1 | 7/2008 |

OTHER PUBLICATIONS

Behrens et al., "Identification and properties of the RNA-dependent RNA polymerase of hepatitis C virus", The EMBO Journal, 1996, vol. 15, pp. 12-22, No. 1.
Bioworld Today, 9 (217):4 Nov. 10, 1998, pp. 1-5.
Birnbock et al., "Sulfate Derivatives of 2-Phenylindols as Novel Steroid Sulfatase Inhibitors", Biochemical Pharmacology, 1990, vol. 39, pp. 1709-1713, No. 11.
Bunker et al., "1,3-Diaryl-2-Carboxyindoles as Potent Non-Peptide Endothelin Antagonists", Bioorganic & Medicinal Chemistry Letters, 1996, vol. 6, pp. 1061-1066, No. 9.
Chemical and Pharmaceutical Bulletin, vol. 19, 1971, p. 263-270.
Denmark et al., "Palladium-Catalyzed Cross-Coupling Reactions of Silanolates: A Paradigm Shift in Silicon-Based Cross-Coupling Reactions", Chem. Eur. J., 2006, vol. 12, pp. 4954-4963.
Dimasi et al., "Characterization of Engineered Hepatitis C Virus NS3 Protease Inhibitors Affinity Selected from Human Pancreatic Secretory Trypsin Inhibitor and Minibody Repertoires", Journal of Virology, 1997, vol. 71, pp. 7461-7469, No. 10.
Elzouki et al., "Serine protease inhibitors in patients with chronic viral hepatitis", Journal of Hepatology, 1997, vol. 27, pp. 42-48.
Ferrari et al., "Characterization of Soluble Hepatitis C Virus RNA-Dependent RNA Polymerase Expressed in *Escherichia coli*", Journal of Virology, 1999, vol. 73, pp. 1649-1654, No. 2.
Fonseca et al., "Synthesis and antiviral evaluation of benzimidazoles, quinoxalines and indoles from dehydroabietic acid", Bioorganic & Medicinal Chemistry, 2004, vol. 12, pp. 103-112.
Forbes et al., "Synthesis, Biological Activity, and Molecular Modeling Studies of Selective 5-HT2C/2B Receptor Antagonists", J. Med. Chem., 1996, vol. 39, pp. 4966-4977, No. 25.
Goldsmith et al., "Studies in the Benzindole Series", J. Org. Chem, 1952, vol. 18, pp. 507-514.
Gopalsamy et al., "Design and synthesis of 2,3,4,9-tetrahydro-1H-carbazole and 1,2,3,4-tetrahydro-cyclopenta[b] indole derivatives as non-nucleoside inhibitors of hepatitis C virus NS5B RNA-dependent RNA polymerase", Bioorganic & Medicinal Chemistry Letters, 2006, vol. 16, pp. 2532-2534.
Humphrey et al., "Practical Methodologies for the Synthesis of Indoles", Chem. Rev., 2006, vol. 106, pp. 2875-2911.
International Search Report for International Application No. PCT/US2007/025754, mailed May 13, 2008, (4 pages).
Written Opinion for PCT/US2007/025754, filed Dec. 17, 2007, (7 pages).
International Search Report for International Application No. PCT/US2007/025765, mailed May 13, 2008, (6 pages).
Written Opinion for PCT/US2007/025765, filed Dec. 17, 2007, (8 pages).
International Search Report for International Application No. PCT/US2007/025757, mailed Mar. 6, 2009, (8 pages).
Written Opinion for PCT/US2007/025757, filed Dec. 17, 2007 (12 pages).
International Search Report for International Application No. PCT/US2008/010130, mailed Jan. 22, 2009, (5 pages).
Written Opinion for PCT/US2008/010130, filed Aug. 27, 2008 (9 pages).
International Search Report for International Application No. PCT/US2008/010149, mailed Feb. 2, 2009, (5 pages).
Written Opinion for PCT/US2008/010149, filed Aug. 27, 2008 (6 pages).
Tan et al., "Hepatitis C Therapeutics: Current Status and Emerging Strategies", Nature Reviews, 2002, vol. 1, pp. 867-881.
Written Opinion for PCT/US2008/083358, filed Nov. 13, 2008 (5 pages).
International Search Report for International Application No. PCT/US2008/010148, mailed Dec. 9, 2008, (3 pages).
Written Opinion for PCT/US2008/010148, filed Aug. 27, 2008 (7 pages).
International Search Report for International Application No. PCT/US2009/046822, mailed Oct. 7, 2009, (5 pages).
Written Opinion for PCT/US2009/046822, filed Jun. 10, 2009 (8 pages).
Ingallinella et al., "Potent Peptide Inhibitors of Human Hepatitis C Virus NS3 Protease are Obtained by Optimizing the Cleavage Products", Biochemistry, 1998, vol. 37, pp. 8906-8914.
Journal of Heterocyclic Chemistry, vol. 12, 1975, pp. 351-358.
Journal of Medicinal Chemistry, vol. 23, No. 7, 1980, pp. 764-773.
Journal of Organic Chemistry, vol. 27, 1962, pp. 3782-3786.
Landro et al., "Mechanistic Role of an NS4A Peptide Cofactor with the Truncated NS3 Protease of Hepatitis C Virus: Elucidation of the NS4A Stimulatory Effect via Kinetic Analysis and Inhibitor Mapping", Biochemistry, 1997, vol. 36, pp. 9340-9348.
Lindsay et al., "SmI2-Promoted Radical Addition Reactions with N-(2-Indolylacyl)oxazolidinones: Synthesis of Bisindole Compounds", Journal of Organic Chemistry, 2007, vol. 72, pp. 4181-4188, No. 11.
Llinas-Brunet et al., "Peptide-Based Inhibitors of the Hepatitis C Virus Serine Protease", Bioorganic & Medicinal Chemistry Letters, 1998, vol. 8, pp. 1713-1718.
Malcolm et al., "SCH 503034, a Mechanism-Based Inhibitor of Hepatitis C Virus NS3 Protease, Suppresses Polyprotein Maturation and Enhances the Antiviral Activity of Alpha Interferon in Replicon Cells", Antimicrobial Agents and Chemotherapy, 2006, vol. 50, pp. 1013-1020, No. 3.
Martin, et al., "Affinity selection of a camelized VH domain antibody inhibitor of hepatitis C virus NS3 protease", Protein Engineering, 1997, vol. 10, pp. 607-614, No. 5.
Martin et al., "Design of Selective Eglin Inhibitors of HCV NS3 Proteinase", Biochemistry, 1998, vol. 37, pp. 11459-11468.
Muratake et al., "Synthesis of Duocarmycin SA by Way of Methyl 4-(Methoxycarbonyl)oxy-3H-pyrrolo[3,2-f]quinoline-2-carboxylate as a Tricyclic Heteroaromatic Intermediate", Chem. Pharm. Bulletin, 1998, vol. 46, pp. 400-412, No. 3.
Ni et al., "Progress and development of small molecule HCV antivirals", Current Opinion in Drug Discovery & Development, 2004, vol. 7, pp. 446-459, No. 4.
Rawal et al., "Photocyclization of Pyrrole Analogues of Stilbene: an Expedient Approach to Anti-tumour Agent CC-1065", Journal Chem. Soc., Chem. Commun., 1984, pp. 1526-1527.
Sechi et al., "Design and Synthesis of Novel Indole β-Diketo Acid Derivatives as HIV-1 Integrase Inhibitors", J. Med. Chem., 2004, vol. 47, pp. 5298-5310, No. 21.
Silvestri et al., "Synthesis and biological evaluation of 5H-indolo [3,2-b][1,5]benzothiazepine derivatives, designed as conformationally constrained analogues of the human immunodeficiency virus type 1 reverse transcriptase inhibitor L-737,126", Antiviral Chemistry & Chemotherapy, 1998, vol. 9, pp. 139-148.
International Search Report for International Application No. PCT/US2008/083351, mailed Feb. 27, 2009, (3 pages).
Written Opinion for PCT/US2008/083351, filed Nov. 13, 2008 (5 pages).
International Search Report for International Application No. PCT/US2008/010147, mailed May 4, 2009 (3 pages).
Written Opinion for PCT/US2008/010147, filed Aug. 27, 2008 (6 pages).
International Search Report for International Application No. PCT/US2008/083358, mailed Mar. 6, 2009, (2 pages).

3-AMINOSULFONYL SUBSTITUTED INDOLE DERIVATIVES AND METHODS OF USE THEREOF

RELATED APPLICATIONS

This application is the national stage application under 35 U.S.C. 371 of International Patent Application No. PCT/US2008/083358, filed Nov. 13, 2008, which claims priority to U.S. Provisional Application No. 60/988,521, filed Nov. 16, 2007. Each of the aforementioned PCT and priority applications is incorporated by reference in its entirety.

FIELD OF THE INVENTION

The present invention relates to 3-Aminosulfonyl Substituted Indole Derivatives, compositions comprising at least one 3-Aminosulfonyl Substituted Indole Derivative, and methods of using the 3-Aminosulfonyl Substituted Indole Derivatives for treating or preventing a viral infection or a virus-related disorder in a patient.

BACKGROUND OF THE INVENTION

HCV is a (+)-sense single-stranded RNA virus that has been implicated as the major causative agent in non-A, non-B hepatitis (NANBH). NANBH is distinguished from other types of viral-induced liver disease, such as hepatitis A virus (HAV), hepatitis B virus (HBV), hepatitis delta virus (HDV), as well as from other forms of liver disease such as alcoholism and primary biliary cirrhosis.

Hepatitis C virus is a member of the hepacivirus genus in the family Flaviviridae. It is the major causative agent of non-A, non-B viral hepatitis and is the major cause of transfusion-associated hepatitis and accounts for a significant proportion of hepatitis cases worldwide. Although acute HCV infection is often asymptomatic, nearly 80% of cases resolve to chronic hepatitis. About 60% of patients develop liver disease with various clinical outcomes ranging from an asymptomatic carrier state to chronic active hepatitis and liver cirrhosis (occurring in about 20% of patients), which is strongly associated with the development of hepatocellular carcinoma (occurring in about 1-5% of patients). The World Health Organization estimates that 170 million people are chronically infected with HCV, with an estimated 4 million living in the United States.

HCV has been implicated in cirrhosis of the liver and in induction of hepatocellular carcinoma. The prognosis for patients suffering from HCV infection remains poor as HCV infection is more difficult to treat than other forms of hepatitis. Current data indicates a four-year survival rate of below 50% for patients suffering from cirrhosis and a five-year survival rate of below 30% for patients diagnosed with localized resectable hepatocellular carcinoma. Patients diagnosed with localized unresectable hepatocellular carcinoma fare even worse, having a live-year survival rate of less than 1%.

HCV is an enveloped RNA virus containing a single-stranded positive-sense RNA genome approximately 9.5 kb in length. The RNA genome contains a 5'-nontranslated region (5' NTR) of 341 nucleotides, a large open reading frame (ORF) encoding a single polypeptide of 3,010 to 3,040 amino acids, and a 3'-nontranslated region (3'-NTR) of variable length of about 230 nucleotides. HCV is similar in amino acid sequence and genome organization to flaviviruses and pestiviruses, and therefore HCV has been classified as a third genus of the family Flaviviridae.

The 5' NTR, one of the most conserved regions of the viral genome, contains an internal ribosome entry site (IRES) which plays a pivotal role in the initiation of translation of the viral polyprotein. A single long open reading frame encodes a polyprotein, which is co- or post-translationally processed into structural (core, E1, E2 and p7) and nonstructural (NS2, NS3, NS4A, NS4B, NS5A, and NS5B) viral proteins by either cellular or viral proteinases. The 3' NTR consists of three distinct regions: a variable region of about 38 nucleotides following the stop codon of the polyprotein, a polyuridine tract of variable length with interspersed substitutions of cytidines, and 98 nucleotides (nt) at the very 3' end which are highly conserved among various HCV isolates. By analogy to other plus-strand RNA viruses, the 3'-NTR is thought to play an important role in viral RNA synthesis. The order of the genes within the genome is: $NH_2$-C-E1-E2-p7-NS2-NS3-NS4A-NS4B-NS5A-NS5B-COOH.

Processing of the structural proteins core (C), envelope protein 1 and (E1, E2), and the p7 region is mediated by host signal peptidases. In contrast, maturation of the nonstructural (NS) region is accomplished by two viral enzymes. The HCV polyprotein is first cleaved by a host signal peptidase generating the structural proteins C1E1, E1/E2, E2/p7, and p7/NS2. The NS2-3 proteinase, which is a metalloprotease, then cleaves at the NS2/NS3 junction. The NS3/4A proteinase complex (NS3 being a serine protease and NS4A acting as a cofactor of the NS3 protease), is then responsible for processing all the remaining cleavage junctions. RNA helicase and NTPase activities have also been identified in the NS3 protein. One-third of the NS3 protein functions as a protease, and the remaining two-thirds of the molecule acts as the helicase/ATPase that is thought to be involved in HCV replication. NS5A may be phosphorylated and acts as a putative cofactor of NS5B. The fourth viral enzyme, NS5B, is a membrane-associated RNA-dependent RNA polymerase (RdRp) and a key component responsible for replication of the viral RNA genome. NS5B contains the "GDD" sequence motif, which is highly conserved among all RdRps characterized to date.

Replication of HCV is thought to occur in membrane-associated replication complexes. Within these, the genomic plus-strand RNA is transcribed into minus-strand RNA, which in turn can be used as a template for synthesis of progeny genomic plus-strands. At least two viral enzymes appear to be involved in this reaction: the NS3 helicase/NTPase, and the NS5B RNA-dependent RNA polymerase. While the role of NS3 in RNA replication is less clear, NS5B is the key enzyme responsible for synthesis of progeny RNA strands. Using recombinant baculoviruses to express NS5B in insect cells and a synthetic nonviral RNA as a substrate, two enzymatic activities have been identified as being associated with it: a primer-dependent RdRp and a terminal transferase (TNTase) activity. It was subsequently confirmed and further characterized through the use of the HCV RNA genome as a substrate. Other studies have shown that NS5B with a C-terminal 21 amino-acid truncation expressed in *Escherichia coli* is also active for in vitro RNA synthesis. On certain RNA templates, NS5B has been shown to catalyze RNA synthesis via a de novo initiation mechanism, which has been postulated to be the mode of viral replication in vivo. Templates with single-stranded 3' termini, especially those containing a 3'-terminal cytidylate moiety, have been found to direct de novo synthesis efficiently. There has also been evidence for NS5B to utilize di- or tri-nucleotides as short primers to initiate replication.

It is well-established that persistent infection of HCV is related to chronic hepatitis, and as such, inhibition of HCV replication is a viable strategy for the prevention of hepatocellular carcinoma. Present treatment approaches for HCV infection suffer from poor efficacy and unfavorable side-effects and there is currently a strong effort directed to the discovery of HCV replication inhibitors that are useful for the treatment and prevention of HCV related disorders. New approaches currently under investigation include the development of prophylactic and therapeutic vaccines, the identification of interferons with improved pharmacokinetic characteristics, and the discovery of agents designed to inhibit the function of three major viral proteins: protease, helicase and polymerase. In addition, the HCV RNA genome itself, particularly the IRES element, is being actively exploited as an antiviral target using antisense molecules and catalytic ribozymes.

Particular therapies for HCV infection include α-interferon monotherapy and combination therapy comprising α-interferon and ribavirin. These therapies have been shown to be effective in some patients with chronic HCV infection. The use of antisense oligonucleotides for treatment of HCV infection has also been proposed as has the use of free bile acids, such as ursodeoxycholic acid and chenodeoxycholic acid, and conjugated bile acids, such as tauroursodeoxycholic acid. Phosphonoformic acid esters have also been proposed as potentially for the treatment of various viral infections including HCV. Vaccine development, however, has been hampered by the high degree of viral strain heterogeneity and immune evasion and the lack of protection against reinfection, even with the same inoculum.

The development of small-molecule inhibitors directed against specific viral targets has become a major focus of anti-HCV research. The determination of crystal structures for NS3 protease, NS3 RNA helicase, and NS5B polymerase has provided important structural insights that should assist in the rational design of specific inhibitors.

NS5B, the RNA-dependent RNA polymerase, is an important and attractive target for small-molecule inhibitors. Studies with pestiviruses have shown that the small molecule compound VP32947 (3-[((2-dipropylamino)ethyl)thio]-5H-1,2,4-triazino[5,6-b]indole) is a potent inhibitor of pestivirus replication and most likely inhibits the NS5B enzyme since resistant strains are mutated in this gene. Inhibition of RdRp activity by (−)β-L-2',3'-dideoxy-3'-thiacytidine 5'-triphosphate (3TC; lamivudine triphosphate) and phosphonoacetic acid also has been observed.

Despite the intensive effort directed at the treatment and prevention of HCV and related viral infections, there exists a need in the art for non-peptide, small-molecule compounds having desirable or improved physicochemical properties that are useful for inhibiting viruses and treating viral infections and virus-related disorders.

SUMMARY OF THE INVENTION

In one aspect, the present invention provides compounds of formula (I):

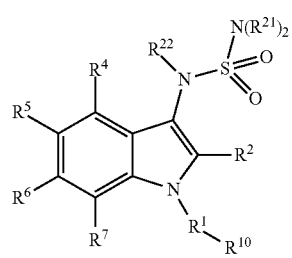

and pharmaceutically acceptable salts, solvates, esters and prodrugs thereof, wherein:

$R^1$ is a bond, $—[C(R^{12})_2]_r—$, $—[C(R^{12})_2]_r—O—[C(R^{12})_2]_q—$, $—[C(R^{12})_2]_r—N(R^9)—[C(R^{12})_2]_q$, $—[C(R^{12})_2]_q—CH=CH—[C(R^{12})_2]_q—$, $—[C(R^{12})_2]_q—C≡C—[C(R^{12})_2]_q—$, or $—[C(R^{12})_2]_q—SO_2—[C(R^{12})_2]_q—$;

$R^2$ is $—[C(R^{12})_2]_q—C(O)N(R^9)SOR^{11}$, $—[C(R^{12})_2]_q—C(O)N(R^9)SO_2R^{11}$, $—[C(R^{12})_2]_q—C(O)N(R^9)SO_2N(R^{11})_2$,

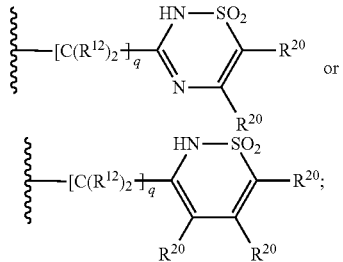

$R^4$, $R^5$, $R^6$ and $R^7$ are each, independently, H, alkyl, alkenyl, alkynyl, aryl, $—[C(R^{12})_2]_q$-cycloalkyl, $—[C(R^{12})_2]_q$-cycloalkenyl, $—[C(R^{12})_2]_q$-heterocycloalkyl, $—[C(R^{12})_2]_q$-heterocycloalkenyl, $—[C(R^{12})_2]_q$-heteroaryl, $—[C(R^{12})_2]_q$-haloalkyl, $—[C(R^{12})_2]_q$-hydroxyalkyl, halo, hydroxy, $—OR^9$, $—CN$, $—[C(R^{12})_2]_q—C(O)R^8$, $—[C(R^{12})_2]_q—C(O)OR^9$, $—[C(R^{12})_2]_q—C(O)N(R^9)_2$, $—[C(R^{12})_2]_q—OR^9$, $—[C(R^{12})_2]_q—N(R^9)_2$, $—[C(R^{12})_2]_q—NHC(O)R^8$, $—[C(R^{12})_2]_q—NR^8C(O)N(R^9)_2$, $—[C(R^{12})_2]_q—NHSO_2R^{11}$, $—[C(R^{12})_2]_q—S(O)_pR^{11}$, $—[C(R^{12})_2]_q—SO_2N(R^9)_2$ or $—SO_2N(R^9)C(O)N(R^9)_2$;

each occurrence of $R^8$ is independently H, alkyl, alkenyl, alkynyl, $—[C(R^{12})_2]_q$-aryl, $—[C(R^{12})_2]_q$-cycloalkyl, $—[C(R^{12})_2]_q$-cycloalkenyl, $—[C(R^{12})_2]_q$-heterocycloalkyl, $—[C(R^{12})_2]_q$-heterocycloalkenyl, $—[C(R^{12})_2]_q$-heteroaryl, haloalkyl or hydroxyalkyl;

each occurrence of $R^9$ is independently H, alkyl, alkenyl, alkynyl, $—[C(R^{12})_2]_q$-aryl, $—[C(R^{12})_2]_q$-cycloalkyl, $—[C(R^{12})_2]_q$-cycloalkenyl, $—[C(R^{12})_2]_q$-heterocycloalkyl, $—[C(R^{12})_2]_q$-heterocycloalkenyl, $—[C(R^{12})_2]_q$-heteroaryl; haloalkyl or hydroxyalkyl;

$R^{10}$ is H, cycloalkyl, cycloalkenyl, heterocycloalkyl, heterocycloalkenyl, aryl, heteroaryl, wherein a cycloalkyl, cycloalkenyl, heterocycloalkyl, heterocycloalkenyl, aryl or heteroaryl group can be optionally and independently substituted with up to 4 substituents, which are each independently selected from H, alkyl, alkenyl, alkynyl, aryl, $—[C(R^{12})_2]_q$-cycloalkyl, $—[C(R^{12})_2]_q$-cycloalkenyl, $—[C(R^{12})_2]_q$-heterocycloalkyl, $—[C(R^{12})_2]_q$-heterocycloalkenyl, $—[C(R^{12})_2]_q$-heteroaryl, $—[C(R^{12})_2]_q$-haloalkyl, $—[C(R^{12})_2]_q$-hydroxyalkyl, halo, hydroxy, $—OR^9$, $—CN$, $—[C(R^{12})_2]_q—C(O)R^8$, $—[C(R^{12})_2]_q—C(O)OR^9$, $—[C(R^{12})_2]_q—C(O)N(R^9)_2$, $—[C(R^{12})_2]_q—OR^9$, $—[C(R^{12})_2]_q—N(R^9)_2$, $—[C(R^{12})_2]_q—NHC(O)R^8$, $—[C(R^{12})_2]_q—NR^8C(O)N(R^9)_2$, $—[C(R^{12})_2]_q—NHSO_2R^{11}$, $—[C(R^{12})_2]_q—S(O)_pR^{11}$, $—[C(R^{12})_2]_q—SO_2N(R^9)_2$ and $—SO_2N(R)C(O)N(R^9)_2$, such that when $R^1$ is a bond, $R^{10}$ is not H;

each occurrence of $R^{11}$ is independently cycloalkyl, cycloalkenyl, heterocycloalkyl, heterocycloalkenyl, heteroaryl, hydroxy or hydroxyalkyl, wherein a cycloalkyl, cycloalkenyl, heterocycloalkyl, heterocycloalkenyl, aryl or heteroaryl group can be optionally and independently substituted with up to 4 substituents, which are each independently selected from —H, alkyl, alkenyl, alkynyl, aryl, —[C(R$^{12}$)$_2$]$_q$-cycloalkyl, —[C(R$^{12}$)$_2$]$_q$-cycloalkenyl, —[C(R$^{12}$)$_2$]$_q$-heterocycloalkyl, —[C(R$^{12}$)$_2$]$_q$-heterocycloalkenyl, —[C(R$^{12}$)$_2$]$_q$-heteroaryl, —[C(R$^{12}$)$_2$]$_q$-haloalkyl, —[C(R$^{12}$)$_2$]$_q$-hydroxyalkyl, halo, hydroxy, —OR$^9$, —CN, —[C(R$^{12}$)$_2$]$_q$—C(O)R$^8$, —[C(R$^{12}$)$_2$]$_q$—C(O)OR$^9$, —[C(R$^{12}$)$_2$]$_q$—C(O)N(R$^9$)$_2$, —[C(R$^{12}$)$_2$]$_q$—OR$^9$, —[C(R$^{12}$)$_2$]$_q$—N(R$^9$)$_2$, —[C(R$^{12}$)$_2$]$_q$—NHC(O)R$^8$, —[C(R$^{12}$)$_2$]$_q$—NR$^8$C(O)N(R$^9$)$_2$, —[C(R$^{12}$)$_2$]$_q$—NHSO$_2$alkyl, —[C(R$^{12}$)$_2$]$_q$—NHSO$_2$cycloalkyl, —[C(R$^{12}$)$_2$]$_q$—NHSO$_2$aryl, —[C(R$^{12}$)$_2$]$_q$—SO$_2$N(R$^9$)$_2$ and —SO$_2$N(R$^9$)C(O)N(R$^9$)$_2$;

each occurrence of R$^{12}$ is independently H, halo, —N(R$^9$)$_2$, —OR$^9$, alkyl, cycloalkyl, cycloalkenyl, heterocycloalkyl or heterocycloalkenyl, wherein a cycloalkyl, cycloalkenyl, heterocycloalkyl or heterocycloalkenyl group can be optionally and independently substituted with up to 4 substituents, which are each independently selected from alkyl, halo, haloalkyl, hydroxyalkyl, hydroxy, —CN, —C(O)alkyl, —C(O)Oalkyl, —C(O)NHalkyl, —C(O)N(alkyl)$_2$, —O-alkyl, —NH$_2$, —NH(alkyl), —N(alkyl)$_2$, —NHC(O)alkyl, —NHSO$_2$alkyl, —SO$_2$alkyl or —SO$_2$NH-alkyl, or two R$^{12}$ groups, together with the carbon atoms to which they are attached, join to form a cycloalkyl, heterocycloalkyl or C=O group;

each occurrence of R$^{20}$ is independently alkyl, aryl, cycloalkyl, heterocycloalkyl or heteroaryl, or both R$^{20}$ groups and the carbon atoms to which they are attached, join to form a cycloalkyl, cycloheteroalkyl, aryl or heteroaryl group wherein a cycloalkyl, cycloheteroalkyl, aryl or heteroaryl group can be substituted with up to 4 groups, which are each independently selected from alkyl, alkenyl, alkynyl, halo, hydroxy, —OR$^9$, —CN, —[C(R$^{12}$)$_2$]$_q$-cycloalkyl, —[C(R$^{12}$)$_2$]$_q$-cycloalkenyl, —[C(R$^{12}$)$_2$]$_q$-heterocycloalkyl, —[C(R$^{12}$)$_2$]$_q$-heterocycloalkenyl, —[C(R$^{12}$)$_2$]$_q$-haloalkyl, —[C(R$^{12}$)$_2$]$_q$-hydroxyalkyl, —[C(R$^{12}$)$_2$]$_q$—C(O)R$^8$, —[C(R$^{12}$)$_2$]$_q$—C(O)OR$^9$, —[C(R$^{12}$)$_2$]$_q$—C(O)N(R$^9$)$_2$, —[C(R$^{12}$)$_2$]$_q$—OR$^9$, —[C(R$^{12}$)$_2$]$_q$—N(R$^9$)$_2$, —[C(R$^{12}$)$_2$]$_q$—NHC(O)R$^8$, —[C(R$^{12}$)$_2$]$_q$—NR$^8$C(O)N(R$^9$)$_2$, —[C(R$^{12}$)$_2$]$_q$—NHSO$_2$R$^{11}$, —[C(R$^{12}$)$_2$]$_q$—S(O)$_p$R$^{11}$, —[C(R$^{12}$)$_2$]$_q$—SO$_2$N(R$^9$)$_2$ and —SO$_2$N(R$^9$)C(O)N(R$^9$)$_2$;

R$^{21}$ is H, alkyl, aryl, cycloalkyl, heterocycloalkyl, heteroaryl or haloalkyl, or R$^{21}$ and R$^{22}$ and the nitrogen atoms to which they are attached, join to form a group having the formula:

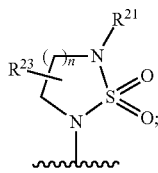

R$^{22}$ is H, alkyl, aryl, cycloalkyl, heterocycloalkyl, heteroaryl or haloalkyl;

R$^{23}$ is an optional substituent selected from alkyl, aryl, —CN, —OH, —O-alkyl, cycloalkyl, halo, heterocycloalkyl, and heteroaryl;

n is an integer ranging from 1 to 3;

each occurrence of p is independently 0, 1 or 2;

each occurrence of q is independently an integer ranging from 0 to 4; and each occurrence of r is independently an integer ranging from 1 to 4.

In another aspect, the present invention provides compounds of formula (II):

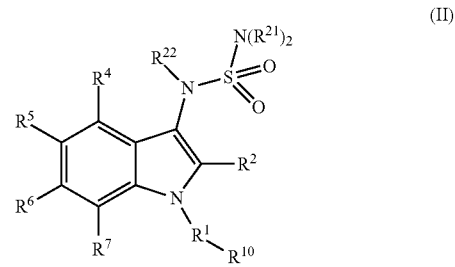

and pharmaceutically acceptable salts, solvates, esters and prodrugs thereof, wherein:

R$^1$ is a bond, —[C(R$^{12}$)$_2$]$_r$—, —[C(R$^{12}$)$_2$]$_r$—O—[C(R$^{12}$)$_2$]$_q$—, —[C(R$^{12}$)$_2$]$_r$—N(R$^9$)—[C(R$^{12}$)$_2$]$_q$—, —[C(R$^{12}$)$_2$]$_q$—CH=CH—[C(R$^{12}$)$_2$]$_q$—, —[C(R$^{12}$)$_2$]$_q$—C≡C—[C(R$^{12}$)$_2$]$_q$—, or —[C(R$^{12}$)$_2$]$_q$—SO$_2$—[C(R$^{12}$)$_2$]$_q$—;

R$^2$ is —C(O)R$^9$, —C(O)OR$^9$, —C(O)OCH$_2$OR$^9$, —C(O)N(R$^9$)$_2$, —[C(R$^{12}$)$_2$]$_q$—C(O)OR$^9$, —[C(R$^{12}$)$_2$]$_q$—C(O)N(R$^9$)$_2$, -alkyl, —[C(R$^{12}$)$_2$]$_q$-aryl, —[C(R$^{12}$)$_2$]$_q$-cycloalkyl, —[C(R$^{12}$)$_2$]$_q$-cycloalkenyl, —[C(R$^{12}$)$_2$]$_q$-heterocycloalkyl, —[C(R$^{12}$)$_2$]$_q$-heteroaryl or —[C(R$^{12}$)$_2$]$_q$-heterocycloalkenyl, wherein an aryl, cycloalkyl, cycloalkenyl, heterocycloalkyl, heterocycloalkenyl or heteroaryl group can be optionally substituted with up to 4 substituents, which are the same or different, and are selected from alkyl, alkenyl, alkynyl, aryl, —[C(R$^{12}$)$_2$]$_q$-cycloalkyl, —[C(R$^{12}$)$_2$]$_q$-cycloalkenyl, —[C(R$^{12}$)$_2$]$_q$-heterocycloalkyl, —[C(R$^{12}$)$_2$]$_q$-heterocycloalkenyl, —[C(R$^{12}$)$_2$]$_q$-heteroaryl, —[C(R$^{12}$)$_2$]$_q$-haloalkyl, —[C(R$^{12}$)$_2$]$_q$-hydroxyalkyl, halo, hydroxy, —OR$^9$, —CN, —[C(R$^{12}$)$_2$]$_q$—C(O)R$^8$, —[C(R$^{12}$)$_2$]$_q$—C(O)OR$^9$, —[C(R$^{12}$)$_2$]$_q$—C(O)N(R$^9$)$_2$, —[C(R$^{12}$)$_2$]$_q$—OR$^9$, —[C(R$^{12}$)$_2$]$_q$—N(R$^9$)$_2$, —[C(R$^{12}$)$_2$]$_q$—NHC(O)R$^8$, —[C(R$^{12}$)$_2$]$_q$—NR$^8$C(O)N(R$^9$)$_2$, —[C(R$^{12}$)$_2$]$_q$—NHSO$_2$R$^{11}$, —[C(R$^{12}$)$_2$]$_q$—S(O)$_p$R$^{11}$, —[C(R$^{12}$)$_2$]$_q$—SO$_2$N(R$^9$)$_2$ and —SO$_2$N(R$^9$)C(O)N(R)$_2$;

each occurrence of R$^8$ is independently H, alkyl, alkenyl, alkynyl, —[C(R$^{12}$)$_2$]$_q$-aryl, —[C(R$^{12}$)$_2$]$_q$-cycloalkyl, —[C(R$^{12}$)$_2$]$_q$-cycloalkenyl, —[C(R$^{12}$)$_2$]$_q$-heterocycloalkyl, —[C(R$^{12}$)$_2$]$_q$-heterocycloalkenyl, —[C(R$^{12}$)$_2$]$_q$-heteroaryl, haloalkyl or hydroxyalkyl;

each occurrence of R$^9$ is independently H, alkyl, alkenyl, alkynyl, —[C(R$^{12}$)$_2$]$_q$-aryl, —[C(R$^{12}$)$_2$]$_q$-cycloalkyl, —[C(R$^{12}$)$_2$]$_q$-cycloalkenyl, —[C(R$^{12}$)$_2$]$_q$-heterocycloalkyl, —[C(R$^{12}$)$_2$]$_q$-heterocycloalkenyl, —[C(R$^{12}$)$_2$]$_q$-heteroaryl, haloalkyl or hydroxyalkyl;

R$^{10}$ is H, cycloalkyl, cycloalkenyl, heterocycloalkyl, heterocycloalkenyl, aryl, heteroaryl, wherein a cycloalkyl, cycloalkenyl, heterocycloalkyl, heterocycloalkenyl, aryl or heteroaryl group can be optionally and independently substituted with up to 4 substituents, which are each independently selected from —H, alkyl, alkenyl, alkynyl, aryl, —[C(R$^{12}$)$_2$]$_q$-cycloalkyl, —[C(R$^{12}$)$_2$]$_q$-cycloalkenyl, —[C(R$^{12}$)$_2$]$_q$-heterocycloalkyl, —[C(R$^{12}$)$_2$]$_q$-heterocycloalkenyl, —[C(R$^{12}$)$_2$]$_q$-heteroaryl, —[C(R$^{12}$)$_2$]$_q$-haloalkyl, —[C(R$^{12}$)$_2$]$_q$-hydroxyalkyl, halo, hydroxy, —OR$^9$, —CN, —[C(R$^{12}$)$_2$]$_q$—C(O)R$^8$, —[C(R$^{12}$)$_2$]$_q$—C(O)OR$^9$, —[C(R$^{12}$)$_2$]$_q$—C(O)N(R$^9$)$_2$, —[C(R$^{12}$)$_2$]$_q$—OR$^9$, —[C(R$^{12}$)$_2$]$_q$—N(R$^9$)$_2$, —[C(R$^{12}$)$_2$]$_q$—NHC(O)R$^8$, —[C(R$^{12}$)$_2$]$_q$—NR$^8$C(O)N(R$^9$)$_2$, —[C(R$^{12}$)$_2$]$_q$—NHSO$_2$R$^{11}$, —[C(R$^{12}$)$_2$]$_q$—S(O)$_p$R$^{11}$, —[C(R$^{12}$)$_2$]$_q$—SO$_2$N(R$^9$)$_2$ and —SO$_2$N(R$^9$)C(O)N(R$^9$)$_2$, such that when R$^1$ is a bond, R$^{10}$ is not H;

each occurrence of $R^{11}$ is independently alkyl, aryl, cycloalkyl, cycloalkenyl, heterocycloalkyl, heterocycloalkenyl, heteroaryl, haloalkyl, hydroxy or hydroxyalkyl, wherein a cycloalkyl, cycloalkenyl, heterocycloalkyl, heterocycloalkenyl, aryl or heteroaryl group can be optionally and independently substituted with up to 4 substituents, which are each independently selected from -H, alkyl, alkenyl, alkynyl, aryl, $—[C(R^{12})_2]_q$-cycloalkyl, $—[C(R^{12})_2]_q$-cycloalkenyl, $—[C(R^{12})_2]_q$-heterocycloalkyl, $—[C(R^{12})_2]_q$-heterocycloalkenyl, $—[C(R^{12})_2]_q$-heteroaryl, $—[C(R^{12})_2]_q$-haloalkyl, $—[C(R^{12})_2]_q$-hydroxyalkyl, halo, hydroxy, $—OR^9$, —CN, $—[C(R^{12})_2]_q$—$C(O)R^8$, $—[C(R^{12})_2]_q$—$C(O)OR^9$, $—[C(R^{12})_2]_q$—$C(O)N(R^9)_2$, $—[C(R^{12})_2]_q$—$OR^9$, $—[C(R^{12})_2]_q$—$N(R^9)_2$, $—[C(R^{12})_2]_q$—$NHC(O)R^8$, $—[C(R^{12})_2]_q$—$NR^8C(O)N(R^9)_2$, $—[C(R^{12})_2]_q$—$NHSO_2$alkyl, $—[C(R^{12})_2]_q$—$NHSO_2$cycloalkyl, $—[C(R^{12})_2]_q$—$NHSO_2$aryl, $—[C(R^{12})_2]_q$—$SO_2N(R^9)_2$ and $—SO_2N(R^9)C(O)N(R^9)_2$;

each occurrence of $R^{12}$ is independently H, halo, $—N(R^9)_2$, $—OR^9$, alkyl, cycloalkyl, cycloalkenyl, heterocycloalkyl or heterocycloalkenyl, wherein a cycloalkyl, cycloalkenyl, heterocycloalkyl car heterocycloalkenyl group can be optionally and independently substituted with up to 4 substituents, which are each independently selected from alkyl, halo, haloalkyl, hydroxyalkyl, hydroxy, —CN, —C(O)alkyl, —C(O)Oalkyl, —C(O)NHalkyl, —C(O)N(alkyl)$_2$, —O-alkyl, —NH$_2$, —NH(alkyl), —N(alkyl)$_2$, —NHC(O)alkyl, —NHSO$_2$alkyl, —SO$_2$alkyl or —SO$_2$NH-alkyl, or two $R^{12}$ groups, together with the carbon atoms to which they are attached, join to form a cycloalkyl, heterocycloalkyl or C=O group;

$R^{21}$ is H, alkyl, aryl, cycloalkyl, heterocycloalkyl, heteroaryl or haloalkyl, or $R^{21}$ and $R^{22}$ and the nitrogen atoms to which they are attached, join to form a group having the formula:

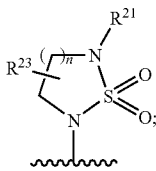

$R^{22}$ is H, alkyl, aryl, cycloalkyl, heterocycloalkyl, heteroaryl or haloalkyl;

$R^{23}$ is an optional substituent selected from alkyl, aryl, —CN, —OH, —O-alkyl, cycloalkyl, halo, heterocycloalkyl, and heteroaryl;

n is an integer ranging from 1 to 3;

each occurrence of p is independently 0, 1 or 2;

each occurrence of q is independently an integer ranging from 0 to 4; and each occurrence of r is independently an integer ranging from 1 to 4.

The compounds of formulas (I) and (II) (the "3-Aminosulfonyl Substituted Indole Derivatives") and pharmaceutically acceptable salts, solvates, esters and prodrugs thereof can be useful for treating or preventing a viral infection or a virus-related disorder in a patient.

Also provided by the invention are methods for treating or preventing a viral infection or a virus-related disorder in a patient, comprising administering to the patient an effective amount of at least one 3-Aminosulfonyl Substituted Indole Derivative or a pharmaceutically acceptable salt, solvate, ester or prodrug thereof.

The present invention further provides pharmaceutical compositions comprising an effective amount of at least one 3-Aminosulfonyl Substituted indole Derivative or a pharmaceutically acceptable salt, solvate, ester or prodrug thereof, and a pharmaceutically acceptable carrier. The compositions can be useful for treating or preventing a viral infection or a virus-related disorder in a patient.

The details of the invention are set forth in the accompanying detailed description below, Although any methods and materials similar to those described herein can be used in the practice or testing of the present invention, illustrative methods and materials are now described. Other features, objects, and advantages of the invention will be apparent from the description and the claims. All patents and publications cited in this specification are incorporated herein by reference.

DETAILED DESCRIPTION OF THE INVENTION

In an embodiment, the present invention provides 3-Aminosulfonyl Substituted Indole Derivatives, pharmaceutical compositions comprising at least one 3-Aminosulfonyl Substituted Indole Derivative, and methods of using the 3-Aminosulfonyl Substituted Indole Derivatives for treating or preventing a viral infection in a patient.

Definitions and Abbreviations

The terms used herein have their ordinary meaning and the meaning of such terms is independent at each occurrence thereof That notwithstanding and except where stated otherwise, the following definitions apply throughout the specification and claims. Chemical names, common names, and chemical structures may be used interchangeably to describe the same structure. If a chemical compound is referred to using both a chemical structure and a chemical name and an ambiguity exists between the structure and the name, the structure predominates. These definitions apply regardless of whether a term is used by itself or in combination with other terms, unless otherwise indicated. Hence, the definition of "alkyl" applies to "alkyl" as well as the "alkyl" portions of "hydroxyalkyl," "haloalkyl," "alkoxy," etc.

As used herein, and throughout this disclosure, the following terms, unless otherwise indicated, shall be understood to have the following meanings:

A "patient" is a human or non-human mammal. In one embodiment, a patient is a human. In another embodiment, a patient is a non-human mammal, including, but not limited to, a monkey, dog, baboon, rhesus, mouse, rat, horse, cat or rabbit. In another embodiment, a patient is a companion animal, including but not limited to a dog, cat, rabbit, horse or ferret. In one embodiment, a patient is a dog. In another embodiment, a patient is a cat.

The term "alkyl" as used herein, refers to an aliphatic hydrocarbon group, wherein one of the aliphatic hydrocarbon group's hydrogen atoms is replaced with a single bond. An alkyl group can be straight or branched and can contain from about 1 to about 20 carbon atoms. In one embodiment, an alkyl group contains from about 1 to about 12 carbon atoms. In another embodiment, an alkyl group contains from about 1 to about 6 carbon atoms. Non-limiting examples of alkyl groups include methyl, ethyl, n-propyl, isopropyl, n-butyl, sec-butyl, isobutyl, tert-butyl, n-pentyl, neopentyl, isopentyl, n-hexyl, isohexyl and neohexyl. An alkyl group may be unsubstituted or optionally substituted by one or more substituents which may be the same or different, each substituent being independently selected from the group consisting of halo, alkenyl, alkynyl, —O-aryl, aryl, heteroaryl, cycloalkyl, cycloalkenyl, cyano, hydroxy, —O-alkyl, —O-haloalkyl, -alkylene-O-alkyl, alkylthio, —NH$_2$, —NH(alkyl), —N(alkyl)$_2$, —NH-aryl, —NH-heteroaryl, —NHC(O)-alkyl, —NHC(O)NH-alkyl, —NHSO$_2$-alkyl, —NHSO$_2$-aryl, —NHSO$_2$-heteroaryl, —NH(cycloalkyl), —OC(O)-alkyl, —OC(O)-aryl, —OC(O)-cycloalkyl, —C(O)alkyl, —C(O)NH$_2$, —C(O)NH-alkyl, —C(O)OH and —C(O)O-alkyl. In one embodiment, an alkyl group is unsubstituted. In another embodiment, an alkyl group is a straight chain alkyl group. In another embodiment, an alkyl group is a branched alkyl group.

The term "alkenyl" as used herein, refers to an aliphatic hydrocarbon group having at least one carbon-carbon double bond, wherein one of the aliphatic hydrocarbon group's hydrogen atoms is replaced with a single bond. An alkenyl group can be straight or branched and can contain from about 2 to about 15 carbon atoms. In one embodiment, an alkenyl group contains from about 2 to about 10 carbon atoms. In another embodiment, an alkenyl group contains from about 2 to about 6 carbon atoms. Non-limiting examples of illustrative alkenyl groups include ethenyl, propenyl, n-butenyl, 3-methylbut-2-enyl, n-pentenyl, octenyl and decenyl. An alkenyl group may be unsubstituted or optionally substituted by one or more substituents which may be the same or different, each substituent being independently selected from the group consisting of halo, alkyl, alkynyl, —O-aryl, aryl, cycloalkyl, cycloalkenyl, cyano, hydroxy, —O-alkyl, —O-haloalkyl, -alkylene-O-alkyl, alkylthio, —NH$_2$, —NH(alkyl), —N(alkyl)$_2$, —NH-aryl, —NH-heteroaryl, —NHC(O)-alkyl, —NHC(O)NH-alkyl, —NHSO$_2$-alkyl, —NHSO$_2$-aryl, —NHSO$_2$-heteroaryl, —NH(cycloalkyl), —OC(O)-alkyl, —OC(O)-aryl, —OC(O)-cycloalkyl, —C(O)alkyl, —C(O)NH$_2$, —C(O)NH-alkyl, —C(O)OH and —C(O)O-alkyl. In one embodiment, an alkenyl group is unsubstituted. In another embodiment, an alkenyl group is a straight chain alkenyl group. In another embodiment, an alkyl group is a branched alkenyl group.

The term "alkynyl" as used herein, refers to an aliphatic hydrocarbon group having at least one carbon-carbon triple bond, wherein one of the aliphatic hydrocarbon group's hydrogen atoms is replaced with a single bond. An alkynyl group can be straight or branched and can contain from about 2 to about 15 carbon atoms. In one embodiment, an alkynyl group contains from about 2 to about 10 carbon atoms. In another embodiment, an alkynyl group contains from about 2 to about 6 carbon atoms. Non-limiting examples of illustrative alkynyl groups include ethynyl, propynyl, 2-butynyl and 3-methylbutynyl. An alkynyl group may be unsubstituted or optionally substituted by one or more substituents which may be the same or different, each substituent being independently selected from the group consisting of halo, alkyl, alkenyl, —O-aryl, aryl, cycloalkyl, cycloalkenyl, cyano, hydroxy, —O-alkyl, —O-haloalkyl, -alkylene-O-alkyl, alkylthio, —NH$_2$, —NH(alkyl), —N(alkyl)$_2$, —NH-aryl, —NH-heteroaryl, —NHC(O)-alkyl, —NHC(O)NH-alkyl, —NHSO$_2$-alkyl, —NHSO$_2$-aryl, —NHSO$_2$-heteroaryl, —NH(cycloalkyl), —OC(O)-alkyl, —OC(O)-aryl, —OC(O)-cycloalkyl, —C(O)alkyl, —C(O)NH$_2$, —C(O)NH-alkyl, —C(O)OH and —C(O)O-alkyl. In one embodiment, an alkynyl group is unsubstituted. In another embodiment, an alkynyl group is a straight chain alkynyl group. In another embodiment, an alkynyl group is a branched alkynyl group.

The term. "alkylene" as used herein, refers to an alkyl group, as defined above, wherein one of the alkyl group's hydrogen atoms is replaced with a bond. Illustrative examples of alkylene include, but are not limited to, —CH$_2$—, —CH$_2$CH$_2$—, —CH$_2$CH$_2$CH$_2$—, —CH$_2$CH$_2$CH$_2$CH$_2$—, —CH(CH$_3$)CH$_2$CH$_2$—, —CH$_2$CH(CH$_3$)CH$_2$— and —CH$_2$CH$_2$CH(CH$_3$)—. In one embodiment, an alkylene group is a straight chain alkylene group. In another embodiment, an alkylene group is a branched alkylene group.

"Aryl" means an aromatic monocyclic or multicyclic ring system having from about 6 to about 14 ring carbon atoms. In one embodiment, an aryl group has from about 6 to about 10 ring carbon atoms. An aryl group can be optionally substituted with one or more "ring system substituents" which may be the same or different, and are as defined herein below. Non-limiting examples of illustrative aryl groups include phenyl and naphthyl. In one embodiment, an aryl group is unsubstituted. In another embodiment, an aryl group is a phenyl group.

The term "cycloalkyl" as used herein, refers to a non-aromatic mono- or multicyclic ring system having from about 3 to about 10 ring carbon atoms. In one embodiment, a cycloalkyl has from about 5 to about 10 ring carbon atoms. In another embodiment, a cycloalkyl has from about 5 to about 7 ring carbon atoms. Non-limiting examples of illustrative monocyclic cycloalkyls include cyclopropyl, cyclopentyl, cyclohexyl, cycloheptyl and the like. Non-limiting examples of illustrative multicyclic cycloalkyls include 1-decalinyl, norbornyl, adamantyl and the like. A cycloalkyl group can be optionally substituted with one or more "ring system substituents" which may be the same or different, and are as defined herein below. In one embodiment, a cycloalkyl group is unsubstituted.

The term "cycloalkenyl" as used herein, refers to a non-aromatic mono- or multicyclic ring system comprising from about 3 to about 10 ring carbon atoms and containing at least one endocyclic double bond. In one embodiment, a cycloalkenyl contains from about 5 to about 10 ring carbon atoms. In another embodiment, a cycloalkenyl contains 5 or 6 ring carbon atoms. Non-limiting examples of illustrative monocyclic cycloalkenyls include cyclopentenyl, cyclohexenyl, cyclohepta-1,3-dienyl, and the like. A cycloalkenyl group can be optionally substituted with one or more "ring system substituents" which may be the same or different, and are as defined herein below. In one embodiment, a cycloalkenyl group is unsubstituted.

The term "halo" as used herein, means —F, —Cl, —Br or —I. In one embodiment, halo refers to —Cl or —F.

The term "haloalkyl" as used herein, refers to an alkyl group as defined above, wherein one or more of the alkyl group's hydrogen atoms has been replaced with a halogen. In one embodiment, a haloalkyl group has from 1 to 6 carbon atoms. In another embodiment, a haloalkyl group is substituted with from 1 to 3 F atoms. Non-limiting examples of illustrative haloalkyl groups include —CH$_2$F, —CHF$_2$, —CF$_3$, —CH$_2$Cl and —CCl$_3$.

The term "hydroxyalkyl" as used herein, refers to an alkyl group as defined above, wherein one or more of the alkyl group's hydrogen atoms has been replaced with an —OH group. In one embodiment, a hydroxyalkyl group has from 1 to 6 carbon atoms. Non-limiting examples of illustrative hydroxyalkyl groups include hydroxymethyl, 2-hydroxyethyl, 3-hydroxypropyl, 4-hydroxybutyl and —CH(OH)CH$_2$CH$_3$.

The term "heteroaryl" as used herein, refers to an aromatic monocyclic or multicyclic ring system comprising about 5 to about 14 ring atoms, wherein from 1 to 4 of the ring atoms is independently O, N or S and the remaining ring atoms are carbon atoms. In one embodiment, a heteroaryl group has 5 to 10 ring atoms. In another embodiment, a heteroaryl group is monocyclic and has 5 or 6 ring atoms. In another embodiment, a heteroaryl group is monocyclic and has 5 or 6 ring atoms and at least one nitrogen ring atom. A heteroaryl group can be optionally substituted by one or more "ring system substituents" which may be the same or different, and are as defined herein below. A heteroaryl group is joined via a ring carbon atom and any nitrogen atom of a heteroaryl can be optionally oxidized to the corresponding N-oxide. The term "heteroaryl" also encompasses a heteroaryl group, as defined above, which has been fused to a benzene ring. Non-limiting examples of illustrative heteroaryls include pyridyl, pyrazinyl, furanyl, thienyl, pyrimidinyl, isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like. The term "heteroaryl" also refers to partially saturated heteroaryl moieties such as, for example, tetrahydroisoquinolyl, tetrahydroquinolyl and the like. In one embodiment, a heteroaryl group is a 6-membered heteroaryl group. In another embodiment, a heteroaryl group is a 5-membered heteroaryl group.

The term "heterocycloalkyl" as used herein, refers to a non-aromatic saturated monocyclic or multicyclic ring system comprising 3 to about 10 ring atoms, wherein from 1 to 4 of the ring atoms are independently O, S or N and the remainder of the ring atoms are carbon atoms. In one embodiment, a heterocycloalkyl group has from about 5 to about 10 ring atoms. In another embodiment, a heterocycloalkyl group has 5 or 6 ring atoms. There are no adjacent oxygen and/or sulfur atoms present in the ring system. Any —NH group in a heterocycloalkyl ring may exist protected such as, for example, as an —N(Boc), —N(CBz), —N(Tos) group and the like; such protected heterocycloalkyl groups are considered part of this invention. A heterocycloalkyl group can be optionally substituted by one or more "ring system substituents" which may be the same or different, and are as defined herein below. The nitrogen or sulfur atom of the heterocyclyl can be optionally oxidized to the corresponding N-oxide, S-oxide or S,S-dioxide. Non-limiting examples of illustrative monocyclic heterocycloalkyl rings include piperidyl, pyrrolidinyl, piperazinyl, morpholinyl, thiomorpholinyl, thiazolidinyl, 1,4-dioxanyl, tetrahydrofuranyl, tetrahydrothiophenyl, lactam, lactone, and the like. A ring carbon atom of a heterocycloalkyl group may be functionalized as a carbonyl group. An illustrative example of such a heterocycloalkyl group is is pyrrolidonyl:

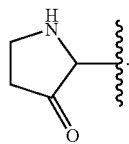

In one embodiment, a heterocycloalkyl group is a 6-membered heterocycloalkyl group. In another embodiment, a heterocycloalkyl group is a 5-membered heterocycloalkyl group.

The term "heterocycloalkenyl" as used herein, refers to a heterocycloalkyl group, as defined above, wherein the heterocycloalkyl group contains from 3 to 10 ring atoms, and at least one endocyclic carbon-carbon or carbon-nitrogen double bond. In one embodiment, a heterocycloalkenyl group has from 5 to 10 ring atoms. In another embodiment, a heterocycloalkenyl group is monocyclic and has 5 or 6 ring atoms. A heterocycloalkenyl group can optionally substituted by one or more ring system substituents, wherein "ring system substituent" is as defined above. The nitrogen or sulfur atom of the heterocycloalkenyl can be optionally oxidized to the corresponding N-oxide, S-oxide or S,S-dioxide. Non-limiting examples of illustrative heterocycloalkenyl groups include 1,2,3,4-tetrahydropyridinyl, 1,2-dihydropyridinyl, 1,4-dihydropyridinyl, 1,2,3,6-tetrahydropyridinyl, 1,4,5,6-tetrahydropyrimidinyl, 2-pyrrolinyl, 3-pyrrolinyl, 2-imidazolinyl, 2-pyrazolinyl, dihydroimidazolyl, dihydrooxazolyl, dihydrooxadiazolyl, pyridonyl (including N-substituted pyridone), dihydrothiazolyl, 3,4-dihydro-2H-pyranyl, dihydrofuranyl, fluorodihydrofuranyl, 7-oxabicyclo[2.2.1]heptenyl, dihydrothiophenyl, dihydrothiopyranyl, and the like. A ring carbon atom of a heterocycloalkenyl group may be functionalized as a carbonyl group. An illustrative example of such a heterocycloalkenyl group is:

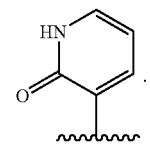 [SMILES: *c1ccc[nH]c1=O]

In one embodiment, a heterocycloalkenyl group is a 6-membered heterocycloalkenyl group. In another embodiment, a heterocycloalkenyl group is a 5-membered heterocycloalkenyl group.

The term "ring system substituent" as used herein, refers to a substituent group attached to an aromatic or non-aromatic ring system which, for example, replaces an available hydrogen on the ring system. Ring substituents may be the same or different, each being independently selected from the group consisting of alkyl, alkenyl, alkynyl, aryl, heteroaryl, aralkyl, alkylaryl, heteroaralkyl, heteroarylalkenyl, heteroarylalkynyl, alkylheteroaryl, hydroxy, hydroxyalkyl, haloalkyl, —O-alkyl, —O-haloalkyl, -alkylene-O-alkyl, —O-aryl, aralkoxy, acyl, halo, nitro, cyano, carboxy, alkoxycarbonyl, aryloxycarbonyl, arylalkoxycarbonyl, alkylsulfonyl, arylsulfonyl, heteroarylsulfonyl, alkylthio, arylthio, heteroarylthio, aralkylthio, heteroaralkylthio, cycloalkyl, heterocyclyl, —OC(O)-alkyl, —OC(O)-aryl, —OC(O)-cycloalkyl, —C(=N—CN)—NH$_2$, —C(=NH)—NH$_2$, —C(=NH)—NH(alkyl), —NY$_1$Y$_2$, -alkylene-NY$_1$Y$_2$, —C(O)NY$_1$Y$_2$ and —SO$_2$NY$_1$Y$_2$, wherein Y$_1$ and Y, can be the same or different and are independently selected from the group consisting of hydrogen, alkyl, aryl, cycloalkyl, and aralkyl. "Ring system substituent" may also mean a single moiety which simultaneously replaces two available hydrogens on the same carbon atom (such as to to form a carbonyl group) or replaces two available hydrogen atoms on two adjacent carbon atoms (one H on each carbon) on a ring system. Examples of such moiety are =O, methylene dioxy, ethylenedioxy, —C(CH$_3$)$_2$— and the like which form moieties such as, for example:

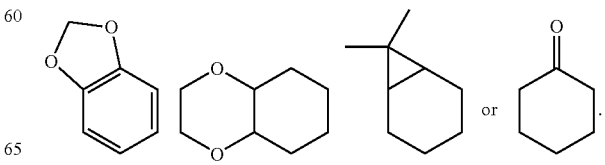

The term in "substituted," as used herein, means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound' or "stable structure" is meant a compound that is sufficiently robust to survive isolation to a useful degree of purity from a reaction mixture, and formulation into an efficacious therapeutic agent.

The term "optionally substituted" as used herein, means optional substitution with the specified groups, radicals or moieties.

The terms "purified", "in purified form" or "in isolated and purified form" as used herein, for a compound refers to the physical state of said compound after being isolated from a synthetic process (e.g. from a reaction mixture), or natural source or combination thereof. Thus, the term "purified", "in purified form" or "in isolated and purified form" for a compound refers to the physical state of said compound after being obtained from a purification process or processes described herein or well known to the skilled artisan (e.g., chromatography, recrystallization and the like), in sufficient purity to be characterizable by standard analytical techniques described herein or well known to the skilled artisan.

It should also be noted that any carbon as well as heteroatom with unsatisfied valences in the text, schemes, examples and Tables herein is assumed to have the sufficient number of hydrogen atoms) to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene at al, *Protective Groups in organic Synthesis* (1991), Wiley, New York.

When any variable (e.g., aryl, heterocycle, $R^{11}$, etc.) occurs more than one time in any constituent or in Formula (I), its definition on each occurrence is independent of its definition at every other occurrence, unless otherwise noted.

Prodrugs and solvates of the compounds of the invention are also contemplated herein. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press. The term "prodrug" as used herein, refers to a compound (e.g., a drug precursor) that is transformed in viva to yield a 3-Aminosulfonyl Substituted Indole Derivative or a pharmaceutically acceptable salt, hydrate or solvate of the compound. The transformation may occur by various mechanisms (e.g., by metabolic or chemical processes), such as, for example, through hydrolysis in blood. A discussion of the use of prodrugs is provided by T. Higuchi and W. Stella, "Pro-drugs as Novel Delivery Systems,"Vol. 14 of the A.C.S. Symposium Series, and in Bioreversible Carriers in Drug Design, ed. Edward B. Roche, American Pharmaceutical Association and Pergamon Press, 1987.

For example, if a 3-Aminosulfonyl Substituted Indole Derivative or a pharmaceutically acceptable salt, hydrate or solvate of the compound contains a carboxylic acid functional group, a prodrug can comprise a ester formed by the replacement of the hydrogen atom of the acid group with a group such as, for example, $(C_1-C_8)$alkyl, $(C_2-C_{12})$alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl) amino)ethyl having from 4 to 10 carbon atoms, 3-phthalidyl, 4-crotonolactonyl, gamma-butyrolacton-4-yl, di-N,N—$(C_1$-$C_2)$alkylamino$(C_2$-$C_3)$alkyl (such as β-dimethylaminoethyl), carbamoyl-$(C_1$-$C_2)$alkyl, N,N-di $(C_1$-$C_2)$alkylcarbamoyl-$(C_1$-$C_2)$alkyl and piperidino-, pyrrolidino- or morpholino $(C_2$-$C_3)$alkyl, and the like.

Similarly, if a 3-Aminosulfonyl Substituted Indole Derivative contains an alcohol functional group, a prodrug can be formed by the replacement of the hydrogen atom of the alcohol group with a group such as, for example, $(C_1$-$C_6)$alkanoyloxymethyl, 1-$((C_1$-$C_6)$alkanoyloxy)ethyl, 1-methyl-1-$((C_1$-$C_6)$alkanoyloxy)ethyl, $(C_1$-$C_6)$alkoxycarbonyloxymethyl, N—$(C_1$-$C_6)$alkoxycarbonylaminomethyl, succinoyl, $(C_1$-$C_6)$alkanoyl, α-amino$(C_1$-$C_4)$alkanyl, arylacyl and α-aminoacyl, or α-aminoacyl-α-aminoacyl, where each α-aminoacyl group is independently selected from the naturally occurring L-amino acids, $P(O)(OH)_2$, —$P(O)(O(C_1$-$C_6)$alkyl)$_2$ or glycosyl (the radical resulting from the removal of a hydroxyl group of the hemiacetal form of a carbohydrate), and the like.

If a 3-Aminosulfonyl Substituted Indole Derivative incorporates an amine functional group, a prodrug can be formed by the replacement of a hydrogen atom in the amine group with a group such as, for example, R-carbonyl, RO-carbonyl, NRR'-carbonyl where R and R' are each independently $(C_1$-$C_{10})$alkyl, $(C_3$-$C_7)$ cycloalkyl, benzyl, or R-carbonyl is a natural α-aminoacyl or natural α-aminoacyl, —C(OH)C(O) $OY^1$ wherein $Y^1$ is H, $(C_1$-$C_6)$alkyl or benzyl, —C($OY^2$)$Y^3$ wherein $Y^2$ is $(C_1$-$C_4)$alkyl and $Y^3$ is $(C_1$-$C_6)$alkyl, carboxy $(C_1$-$C_6)$alkyl, amino$(C_1$-$C_4)$alkyl or mono-N— or di-N,N— $(C_1$-$C_6)$alkylaminoalkyl, —C($Y^4$)$Y^5$ wherein $Y^4$ is H or methyl and $Y^5$ is mono-N— or di-N,N—$(C_1$-$C_6)$alkylamino morpholino, piperidin-1-yl or pyrrolidin-1-yl, and the like.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of illustrative solvates include ethanolates, methanolates, and the like. "Hydrate" is a solvate wherein the solvent molecule is $H_2O$.

One or more compounds of the invention may optionally be converted to a solvate. Preparation of solvates is generally known. Thus, for example, M. Caira et al, *J. Pharmaceutical Sci.*, 93(3), 601-611 (2004) describe the preparation of the solvates of the antifungal fluconazole in ethyl acetate as well as from water. Similar preparations of solvates, hemisolvate, hydrates and the like are described by E. C. van Tonder et al, *AAPS Pharm Sci Tech.*, 5(1), article 12 (2004); and A. L. Bingham et al, *Chem. Commun.*, 603-604 (2001). A typical, non-limiting, process involves dissolving the inventive compound in desired amounts of the desired solvent (organic or water or mixtures thereof) at a higher than ambient temperature, and cooling the solution at a rate sufficient to form crystals which are then isolated by standard methods. Analytical techniques such as, for example I.R. spectroscopy, show the presence of the solvent (or water) in the crystals as a solvate (or hydrate).

The term "effective amount" or "therapeutically effective amount" is meant to describe an amount of compound or a composition of the present invention that is effective to treat or prevent a viral infection or a virus-related disorder.

Metabolic conjugates, such as glucuronides and sulfates which can undergo reversible conversion to the 3-Aminosulfonyl Substituted Indole Derivatives are contemplated in the present invention.

The 3-Aminosulfonyl Substituted Indole Derivatives may form salts, and all such salts are contemplated within the scope of this invention. Reference to a 3-Aminosulfonyl Substituted Indole Derivative herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a 3-Aminosulfonyl Substituted Indole Derivative contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the Formula I may be formed, for example, by reacting a 3-Aminosulfonyl Substituted Indole Derivative with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates,) and the like. Additionally, acids which are generally considered suitable for the formation of pharmaceutically useful salts from basic pharmaceutical compounds are discussed, for example, by P. Stahl at al. Camille G. (eds.) *Handbook of Pharmaceutical Salts. Properties, Selection and Use.* (2002) Zurich: Wiley-VCH; S. Berge at al, *Journal of Pharmaceutical Sciences* (1977) 66(1) 1-19; P. Gould, *International J. of Pharmaceutics* (1986) 33, 201-217; Anderson at al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, choline, and salts with amino acids such as arginine, lysine and the like. Basic nitrogen-containing groups may be quarternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Pharmaceutically acceptable esters of the present compounds include the following groups: (1) carboxylic acid esters obtained by esterification of the hydroxy groups, in which the non-carbonyl moiety of the carboxylic acid portion of the ester grouping is selected from straight or branched chain alkyl (for example, acetyl, n-propyl, t-butyl, or n-butyl), alkoxyalkyl (for example, methoxymethyl), aralkyl (for example, benzyl), aryloxyalkyl (for example, phenoxymethyl), aryl (for example, phenyl optionally substituted with, for example, halogen, $C_{1-4}$alkyl, or $C_{1-4}$alkoxy or amino); (2) sulfonate esters, such as alkyl- or aralkylsulfonyl (for example, methanesulfonyl); (3) amino acid esters (for example, L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di($C_{6-24}$)acyl glycerol.

The 3-Aminosulfonyl Substituted Indole Derivatives may contain asymmetric or chiral centers, and, therefore, exist in different stereoisomeric forms. It is intended that all stereoisomeric forms of the 3-Aminosulfonyl Substituted Indole Derivatives as well as mixtures thereof, including racemic mixtures, form part of the present invention. In addition, the present invention embraces all geometric and positional isomers. For example, if a 3-Aminosulfonyl Substituted indole Derivative incorporates a double bond or a fused ring, both the cis- and trans-forms, as well as mixtures, are embraced within the scope of the invention.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the 3-Aminosulfonyl Substituted Indole Derivatives may be atropisomers (e.g., substituted biaryls) and are considered as part of this invention. Enantiomers can also be separated by use of chiral HPLC column.

The straight line — as a bond generally indicates a mixture of, or either of, the possible isomers, non-limiting example(s) include, containing (R)- and (S)-stereochemistry. For example,

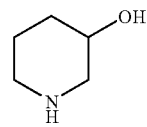

means containing both

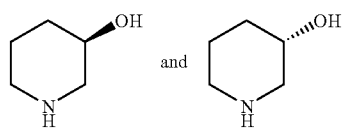 [SMILES: O[C@@H]1CCCNC1 ; "and" ; O[C@H]1CCCNC1]

A dashed line (-----) represents an optional bond.

Lines drawn into the ring systems, such as, for example:

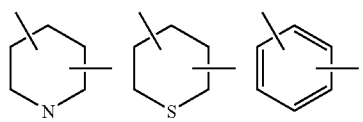

indicate that the indicated line (bond) may be attached to any of the substitutable ring atoms, non limiting examples include carbon, nitrogen and sulfur ring atoms.

As well known in the art, a bond drawn from a particular atom wherein no moiety is depicted at the terminal end of the bond indicates a methyl group bound through that bond to the atom, unless stated otherwise. For example:

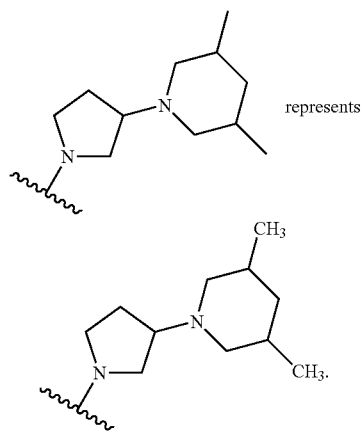

All stereoisomers (for example, geometric isomers, optical isomers and the like) of the present compounds (including those of the salts, solvates, hydrates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). For example, if a 3-Aminosulfonyl Substituted Indole Derivative incorporates a double bond or a fused ring, both the cis- and trans-forms, as well as mixtures, are embraced within the scope of the invention.

Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the *IUPAC* 1974 Recommendations. The use of the terms "salt", "solvate", "ester", "prodrug" and the like, is intended to equally apply to the salt, solvate, ester and prodrug of enantiomers, stereoisomers, rotamers, positional isomers, racemates or prodrugs of the inventive compounds.

The present invention also embraces isotopically-labelled compounds of the present invention which are identical to those recited herein, but for the fact that one or more atoms are replaced by an atom having an atomic mass or mass number different from the atomic mass or mass number usually found in nature. Such compounds are useful as therapeutic, diagnostic or research reagents. Examples of isotopes that can be incorporated into compounds of the invention include isotopes of hydrogen, carbon, nitrogen, oxygen, phosphorus, fluorine and chlorine, such as $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively.

Certain isotopically-labelled 3-Aminosulfonyl Substituted Indole Derivatives (e.g., those labeled with $^3H$ and $^{14}C$) are useful in compound and/or substrate tissue distribution assays. Tritiated (i.e., $^3H$) and carbon-14 (i.e., $^{14}C$) isotopes are particularly preferred for their ease of preparation and detectability. Further, substitution with heavier isotopes such as deuterium (i.e., $^2H$) may afford certain therapeutic advantages resulting from greater metabolic stability (e.g., increased in vivo half-life or reduced dosage requirements) and hence may be preferred in some circumstances. Isotopically labelled 3-Aminosulfonyl Substituted Indole Derivatives can generally be prepared by following procedures analogous to those disclosed in the Schemes and/or in the Examples herein below, by substituting an appropriate isotopically labelled reagent for a non-isotopically labelled reagent.

Polymorphic forms of the 3-Aminosulfonyl Substituted Indole Derivatives, and of the salts, solvates, hydrates, esters and prodrugs of the 3-Aminosulfonyl Substituted Indole Derivatives, are intended to be included in the present invention.

The following abbreviations are used below and have the following meanings: ATP is adenosine-5'-triphosphate; BSA is bovine serum albumin; CDCl$_3$ is deuterated chloroform; CTP is cytidine-5'-triphosphate; DABCO is 1,4-diazabicyclo[2.2,2]octane; dba is dibenzylideneacetone; DME is dimethoxyethane; DMF is N,N-dimethylformamide; DMSO is dimethylsulfoxide; dppf is 1,1'-bis(diphenylphosphino)ferrocene; DTT is 1,4-dithio-threitol; EDCI is 1-(3-dimethylaminopropyl)-3-ethylcarbodiimide; EDTA is ethylenediaminetetraacetic acid; Et$_3$N is triethylamine; EtOAc is ethyl acetate; GTP is guanosine-5'-triphosphate; HPLC is high performance liquid chromatography; MeOH is methanol; TBAF is tetrabutylammonium fluoride; THF is tetrahydrofuran; TLC is thin-layer chromatography; TMS is trimethylsilyl; and UTP is uridine-5'-triphosphate.

The 3-Aminosulfonyl Substituted Indole Derivatives of Formula (I)

The present invention provides 3-Aminosulfonyl Substituted Indole Derivatives having the formula:

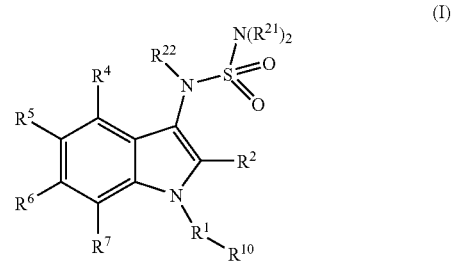

and pharmaceutically acceptable salts, solvates, esters and prodrugs thereof, wherein $R^1$, $R^2$, $R^4$, $R^5$, $R^6$, $R^7$, $R^{10}$, $R^{21}$ and $R^{22}$ are defined above for the compounds of formula (I).

In one embodiment, $R^1$ is bond.
In another embodiment, $R^1$ is —[C(R$^{12}$)$_2$]$_r$—.
In another embodiment, $R^1$ is —[C(R$^{12}$)$_2$]$_r$—O—[C(R$^{12}$)$_2$]$_q$—.

In still another embodiment, $R^1$ is —[C(R$_{12}$)$_2$]$_r$—N(R$^9$)—[C(R$^{12}$)$_2$]$_q$—.

In yet another embodiment, $R^1$ is —[C(R$^{12}$)$_2$]$_q$—CH=CH—[C(R$^{12}$)$_2$]$_q$—.

In another embodiment, $R^1$ is —[C(R$^{12}$)$_2$]$_q$—C≡C—[C(R$^{12}$)$_2$]$_q$—.

In a further embodiment, $R^1$ is —[C(R$^{12}$)$_2$]$_q$—SO$_2$—[C(R$^{12}$)$_2$]$_q$—.

In one embodiment, $R^1$ is —CH$_2$—, —CH$_2$CH$_2$—, —CH(CH$_3$)— or

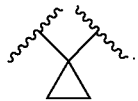 [SMILES: *C1(*)CC1]

In another embodiment, $R^1$ is —CH$_2$—.
In another embodiment, $R^1$ is

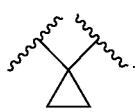 [SMILES: *C1(*)CC1]

In one embodiment, $R^{10}$ is aryl.
In another embodiment, $R^{10}$ is H.
In another embodiment, $R^{10}$ is cycloalkyl.
In another embodiment, $R^{10}$ is cycloalkenyl.
In still another embodiment, $R^{10}$ is heterocycloalkenyl.
In another embodiment, $R^{10}$ is heteroaryl.
In another embodiment, $R^{10}$ is heterocycloalkyl.
In another embodiment, $R^{10}$ is phenyl.
In another embodiment, $R^{10}$ is phenyl, which is substituted with from 1-4 groups independently selected from: halo, —NH$_2$, —NHSO$_2$-alkyl, haloalkyl, methoxy, —O-haloalkyl, —[C(R$^{12}$)$_2$]$_q$—NHC(O)NH-alkyl, alkyl, hydroxy, —CN, —C(O)NH$_2$ or —[C(R$^{12}$)$_2$]$_q$—NH$_2$.
In yet another embodiment, $R^{10}$ is pyridyl.
In a further embodiment, $R^{10}$ is

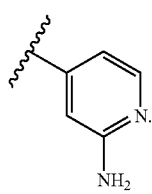 [SMILES: *c1ccnc(N)c1]

In another embodiment, —$R^{10}$ is:

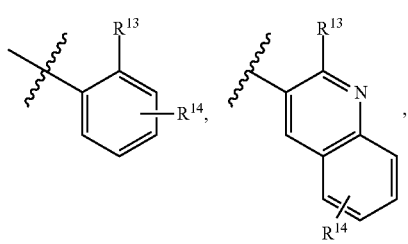

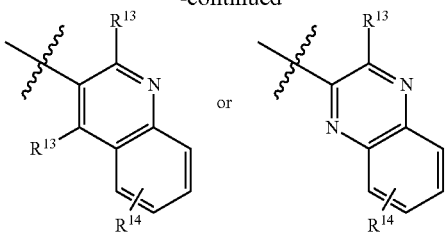

wherein R represents up to 2 optional and additional phenyl substituents, each independently selected from halo, —O-alkyl, alkyl, —CF$_3$, —CN, —NHSO$_2$-alkyl, —NO$_2$, —C(O)NH$_2$, —C(O)OH, —NH$_2$, —SO$_2$-alkyl, —SO$_2$NH-alkyl, —S-alkyl, —SO$_2$NH$_2$, —NHC(O)-alkyl, —C(O)O-alkyl, —C(O)-heterocycloalkyl and heteroaryl.

in another embodiment, $R^{10}$ is

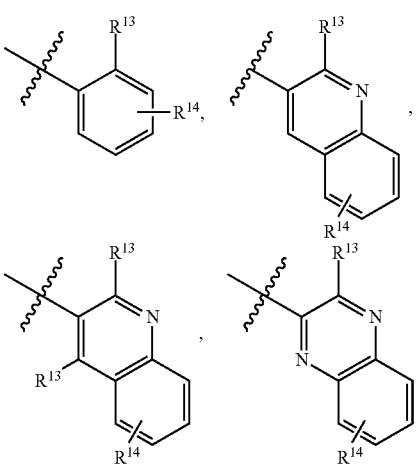

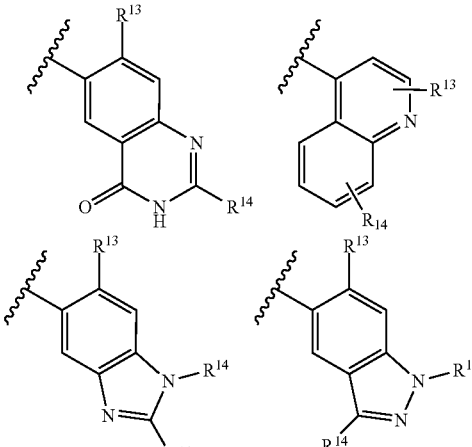

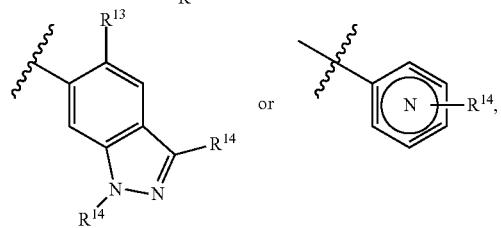

wherein $R^{13}$ is F or Cl and $R^{14}$ represents up to 4 optional and additional substituents, each independently selected from alkyl, cycloalkyl, $CF_3$, —CN, halo, —O-alkyl, —$NHSO_2$-alkyl, —$NO_2$, —$C(O)NH_2$, —C(O)NH-alkyl, —C(O)OH, hydroxy, —$NH_2$, —$SO_2$alkyl, —$SO_2$NHalkyl, —S-alkyl, —$CH_2NH_2$, —$CH_2OH$, —$SO_2NH_2$, —NHC(O)-alkyl, —C(O)O-alkyl, —C(O)-heterocycloalkyl and heteroaryl.

In still another embodiment, $R^1$ is —$CH_2$— or

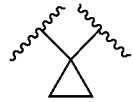 [SMILES: *C1(*)CC1]

and $R^{10}$ is

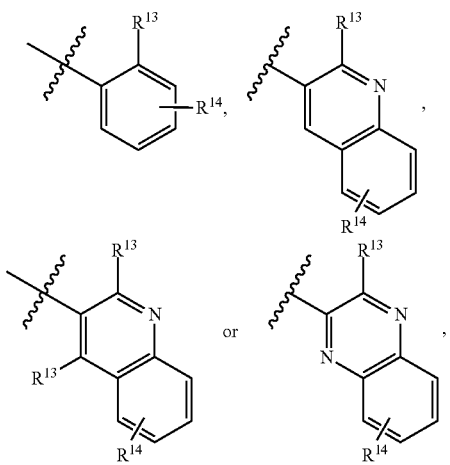

wherein $R^{13}$ is F or Cl and $R^{14}$ represents up to 4 optional and additional substituents, each independently selected from alkyl, cycloalkyl, $CF_3$, —CN, halo, —O-alkyl, —$NHSO_2$-alkyl, —$NO_2$, —$C(O)NH_2$, —C(O)NH-alkyl, —C(O)OH, hydroxy, —$NH_2$, —$SO_2$alkyl, —$SO_2$NHalkyl, —S-alkyl, —$CH_2NH_2$, —$CH_2OH$, —$SO_2NH_2$, —NHC(O)-alkyl, —C(O)O-alkyl, —C(O)-heterocycloalkyl and heteroaryl In one embodiment, —$R^1$-$R^{10}$ is benzyl.

In another embodiment, —$R^1$-$R^{10}$ is benzyl, wherein the phenyl moiety of the benzyl group is substituted with from 1-4 groups independently selected from: halo, —$NH_2$, —$NHSO_2$-alkyl, haloalkyl, methoxy, —O-haloalkyl. —[C($R^{12}$)$_2$]$_q$—NHC(O)NH-alkyl, alkyl, hydroxy, —CN, —C(O)NH$_2$ or —[C($R^{12}$)$_2$]$_q$—NH$_2$.

In still another embodiment, —$R^1$-$R^{10}$ is

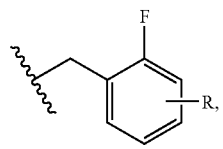

wherein R represents up to 2 optional and additional phenyl substituents, each independently selected from halo, —O-alkyl, alkyl, —$CF_3$, —CN, —$NHSO_2$-alkyl, —$NO_2$, —C(O)NH$_2$, —C(O)OH, —$NH_2$, —$SO_2$-alkyl, $SO_2$NH alkyl, —S-alkyl, —$CH_2NH_2$, —$SO_2NH_2$, —NHC(O)-alkyl, —C(O)O-alkyl, —C(O)-heterocycloalkyl and heteroaryl.

In another embodiment, —$R^1$-$R^{10}$ is

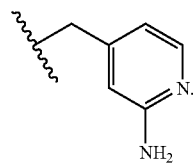 [SMILES: *Cc1ccnc(N)c1]

In still another embodiment, —$R^1$-$R^{10}$ is alkyl.

In yet another embodiment, —$R^1$-$R^{10}$ is —$R^1$-$R^{10}$ is benzyl, wherein the phenyl moiety of the benzyl group is substituted with 1 or 2 fluorine atoms.

In yet another embodiment, —$R^1R^{10}$ is —$R^1$-$R^{10}$ is benzyl, wherein the phenyl moiety of the benzyl group is substituted with 1 or 2 methyl groups.

In yet another embodiment, —$R^1$-$R^{10}$ is —$R^1$-$R^{10}$ is benzyl, wherein the phenyl moiety of the benzyl group is substituted with one fluorine atom and one methyl group.

In another embodiment, —$R^1$-$R^{10}$ is haloalkyl.

In a further embodiment, —$R^1$-$R^{10}$ is —$CH_2$-cycloalkyl.

In one embodiment, $R^2$ is —C(O)NHSO$_2$R or —C(O)NHSO$_2$N($R^9$)$_2$.

In another embodiment, $R^2$ is —[C($R^{12}$)$_2$]$_q$—C(O)N($R^9$)SO$_2$$R^{11}$.

In another embodiment, $R^2$ is —[C($R^{12}$)$_2$]$_q$—C(O)N($R^9$)SOR$^{11}$.

In still another embodiment, $R^2$ is —[C($R^{12}$)$_2$]$_q$—C(O)N($R^9$)SO$_2$N($R^{11}$)$_2$.

In another embodiment, $R^2$ is

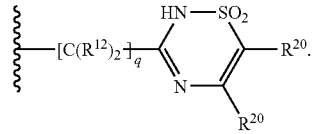

In another embodiment, $R^2$ is

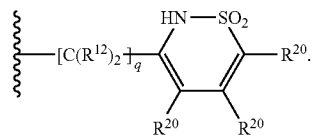

In another embodiment, $R^2$ is —C(O)N($R^9$)SO$_2$$R^{11}$.

In another embodiment, $R^2$ is —C(O)NHSO$_2$$R^{11}$.

In another embodiment, $R^2$ is —C(O)NHSO$_2$$R^{11}$ and $R^{11}$ is —[C($R^{12}$)$_2$]$_q$-alkyl.

In yet another embodiment, $R^2$ is —C(O)NHSO$_2$$R^{11}$ and $R^{11}$ is —[C($R^{12}$)$_2$]$_q$-aryl.

In another embodiment, $R^2$ is —C(O)NHSO$_2$$R^{11}$ and $R^{11}$ is —[C($R^{12}$)$_2$]$_q$-cycloalkyl.

In a further embodiment, $R^2$ is —C(O)NHSO$_2$$R^{11}$ and $R^{11}$ is —[C($R^{12}$)$_2$]$_q$-heterocycloalkyl.

In another embodiment, $R^2$ is —C(O)NHSO$_2$$R^{11}$ and $R^{11}$ is —[C($R^{12}$)$_2$]$_q$-heteroaryl.

In another embodiment, $R^2$ is —C(O)NHSO$_2$$R^{11}$ and $R^{11}$ is —[C($R^{12}$)$_2$]$_q$-haloalkyl.

In still another embodiment, $R^2$ is —C(O)NHSO$_2$$R^{11}$ and $R^{11}$ is —[C($R^{12}$)$_2$]$_q$-hydroxyalkyl.

In still another embodiment, $R^2$ is —C(O)NHSO$_2$$R^{11}$ and $R^{11}$ is alkyl.

In yet another embodiment, $R^2$ is —C(O)NHSO$_2$R$^{11}$ and $R^{11}$ is aryl.

In another embodiment, $R^2$ is —C(O)NHSO$_2$R$^{11}$ and $R^{11}$ is cycloalkyl.

In a further embodiment, $R^2$ is —C(O)NHSO$_2$R$^{11}$ and $R^{11}$ is heterocycloalkyl.

In another embodiment, $R^2$ is —C(O)NHSO$_2$R$^{11}$ and $R^{11}$ is heteroaryl.

In another embodiment, $R^2$ is —C(O)NHSO$_2$R$^{11}$ and $R^{11}$ is haloalkyl.

In still another embodiment, $R^2$ is —C(O)NHSO$_2$R$^{11}$ and $R^{11}$ is hydroxyalkyl.

In another embodiment, $R^2$ is —C(O)NHSO$_2$R$^{11}$ and $R^{11}$ is —[C(R$^{12}$)$_2$]$_q$-phenyl.

In another embodiment, $R^2$ is —C(O)NHSO$_2$R$^{11}$ and $R^{11}$ benzyl.

In another embodiment, $R^2$ is —C(O)NHSO$_2$R$^{11}$ and $R^{11}$ is naphthyl.

In yet another embodiment, $R^2$ is —C(O)NHSO$_2$R$^{11}$ and $R^{11}$ is —NH$_2$ or —N(CH$_3$)$_2$.

In another embodiment, $R^2$ is —C(O)NHSO$_2$CH$_3$.

In another embodiment, $R^2$ is —C(O)NHSO$_2$CH$_2$CH$_3$.

In another embodiment, $R^2$ is —C(O)NHSO$_2$R$^{11}$, and $R^{11}$ is alkyl, aryl, cycloalkyl, haloalkyl, heteroaryl, heterocycloalkyl or hydroxyalkyl.

In one embodiment, $R^2$ is —C(O)NHSO$_2$R$^{11}$ and $R^{11}$ is alkyl, cycloalkyl or aryl.

In one embodiment, $R^2$ is —C(O)NHSO$_2$N(R$^9$)$_2$ and $R^9$ is H, alkyl, aryl, cycloalkyl, heteroaryl or heterocycloalkyl.

In another embodiment, $R^2$ is —C(O)NHSO$_2$N(R$^9$)$_2$ and $R^9$ is H, alkyl or cycloalkyl.

In another embodiment, $R^2$ is —C(O)NHSO$_2$R$^{11}$ and $R^{11}$ is methyl, ethyl, isopropyl, cyclopropyl or phenyl.

In another embodiment, $R^2$ is —C(O)NHSO$_2$N(R$^9$)$_2$ and $R^9$ is H, methyl, ethyl or cyclopropyl.

In still another embodiment, $R^2$ is —C(O)NHSO$_2$R$^{11}$ and $R^{11}$ is cyclopropyl.

In another embodiment, $R^2$ is —C(O)NHSO$_2$N(R$^9$)$_2$ and $R^9$ is H or methyl.

In still another embodiment, $R^2$ is —C(O)NHSO$_2$R$^{11}$ and $R^{11}$ is phenyl, which is optionally substituted with up to 3 groups independently selected from: alkyl, F, Cl, methyl, —NH$_2$, —NO$_2$, methoxy, —SO$_2$NH$_2$, —COOH, —[C(R$^{12}$)$_2$]$_q$—C(O)O-alkyl, hydroxy, —NHSO$_2$-alkyl, —[C(R$^{12}$)$_2$]$_q$—SO$_2$-alkyl, —CF$_3$, —CN, thiazolyl, —C(O)NH-alkyl, —NHSO$_2$-phenyl, —NHSO$_2$-cyclopropyl, —NHSO$_2$-alkyl, —[C(R$^{12}$)$_2$]$_q$—NHC(O)-alkyl, pyrazolyl or —OCH$_2$C(O)NH$_2$.

In yet another embodiment, $R^2$ is —C(O)NHSO$_2$R$^{11}$ and $R^{11}$ is cyclopropyl, cyclobutyl, cyclopentyl or cyclohexyl.

In one embodiment, $R^4$ is H.
In another embodiment, $R^4$ is H or F.
In another embodiment, $R^4$ is F.
In another embodiment, $R^5$ is H.
In another embodiment, $R^6$ is H.
In another embodiment, $R^6$ is H or F.
In another embodiment, $R^6$ is F.
In still another embodiment, $R^7$ is H.
In another embodiment, $R^4$ and $R^7$ are each H.
In yet another embodiment, $R^4$, $R^6$ and $R^7$ are each H.
In another embodiment, $R^4$, $R^5$, $R^6$ and $R^7$ are each H.
In a further embodiment, $R^4$, $R^6$ and $R^7$ are each H and $R^5$ is other than H.
In another embodiment, $R^4$, $R^6$ and $R^7$ are each H and $R^5$ is halo.
In another embodiment, $R^4$, $R^6$ and $R^7$ are each H and $R^5$ is Cl.

In still another embodiment, $R^4$, $R^6$ and $R^7$ are each H and $R^5$ is alkyl.

In another embodiment, $R^4$, $R^6$ and $R^7$ are each H and $R^5$ is halo.

In another embodiment, $R^4$, $R^6$ and $R^7$ are each H and $R^5$ is methyl.

In a further embodiment, $R^4$, $R^6$ and $R^7$ are each H and $R^5$ is Cl.

In another embodiment, $R^4$ and $R^7$ are each H and and $R^5$ and $R^6$ are other than H.

In another embodiment, $R^5$ is other than H.
In still another embodiment, $R^5$ is alkyl.
In yet another embodiment, $R^5$ is halo.
In another embodiment, $R^5$ is Cl.
In still another embodiment, $R^5$ is methyl.
In another embodiment, $R^5$ is ethyl.
In another embodiment, $R^6$ is H.
In another embodiment, $R^6$ is other than H.
In a further embodiment, $R^6$ is alkyl.
In yet another embodiment, $R^6$ is halo.
In still another embodiment, $R^6$ is methyl.
In another embodiment, $R^6$ is F.
In another embodiment, $R^4$ is H or F; $R^5$ is methyl or ethyl; $R^6$ is H or F; and $R^7$ is H.

In one embodiment, $R^{21}$ is haloalkyl.
In another embodiment, $R^{21}$ is H.
In another embodiment, $R^{21}$ is alkyl.
In still another embodiment, $R^{21}$ is aryl.
In another embodiment, $R^{21}$ is cycloalkyl.
In another embodiment, $R^{21}$ is heterocycloalkyl.
In yet another embodiment, $R^{21}$ is heteroaryl.
In another embodiment, $R^{21}$ is haloalkyl.
In further embodiment, $R^{21}$ is —(CH$_2$)$_s$-halo, wherein s is an integer ranging from 1 to 6.
In another embodiment, $R^{21}$ is —(CH$_2$)$_2$-halo.
In still another embodiment, $R^{21}$ is —(CH$_2$)$_3$-halo.
In another embodiment, $R^{21}$ is -alkylene-Cl.
In another embodiment, $R^{21}$ is —(CH$_2$)$_s$—Cl, wherein s is an integer ranging from 1 to 6.
In yet another embodiment, $R^{21}$ is —(CH$_2$)$_2$—Cl.
In another embodiment, $R^{21}$ is —(CH$_2$)$_3$—Cl.
In one embodiment, $R^{22}$ is H.
In another embodiment, $R^{22}$ is alkyl.
In still another embodiment, $R^{22}$ is aryl.
In another embodiment, $R^{22}$ is cycloalkyl.
In another embodiment, $R^{22}$ is heterocycloalkyl.
In yet another embodiment, $R^{22}$ is heteroaryl.
In another embodiment, $R^{22}$ is haloalkyl.
In one embodiment, $R^{22}$ is haloalkyl and $R^{22}$ is H.
In another embodiment, $R^{21}$ is —(CH$_2$)$_s$-halo, wherein s is an integer ranging from 1 to 6, and $R^{22}$ is H.
In another embodiment, $R^{21}$ is —(CH$_2$)$_s$—Cl, wherein s is an integer ranging front 1 to 6, and $R^{22}$ is H.
In one embodiment, $R^{21}$ and $R^{22}$ and the nitrogen atoms to which they are attached, join to form a group having the formula:

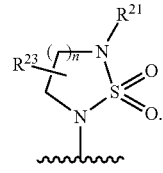

In another embodiment, $R^{21}$ and $R^{22}$ and the nitrogen atoms to which they are attached, join to form a group having the formula:

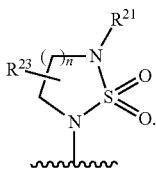

In another embodiment, $R^{21}$ and $R^{22}$ and the nitrogen atoms to which they are attached, join to form a group having the formula:

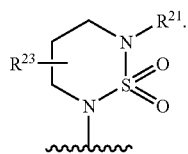

In one embodiment, $R^2$ is —C(O)NHSO$_2$R$^{11}$ or —C(O)NHSO$_2$N(R$^9$)$_2$; $R^{21}$ is H, alkyl, aryl, cycloalkyl, heterocycloalkyl, heteroaryl or haloalkyl; and $R^{22}$ is H.

In one embodiment, $R^2$ is —C(O)NHSOR$^{11}$ or —C(O)NHSO$_2$N(R$^9$)$_2$ $R^{21}$ is haloalkyl; and $R^{22}$ is H.

In one embodiment, $R^2$ is —C(O)NHSO$_2$R$^{11}$ or —C(O)NHSO$_2$N(R$^9$)$_2$; and $R^{21}$ and $R^{22}$ and the nitrogen atoms to which they are attached, join to form a group having the formula:

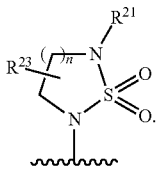

In one embodiment, $R^2$ is —C(O)NHSO$_2$R$^{11}$; $R^{11}$ is alkyl or cycloalkyl; $R^{21}$ is H, alkyl, aryl, cycloalkyl, heterocycloalkyl, heteroaryl or haloalkyl; and $R^{22}$ is H.

In another embodiment, $R^2$ is —C(O)NHSO$_2$R$^{11}$; $R^{11}$ is alkyl or cycloalkyl; $R^{21}$ is haloalkyl; and $R^{22}$ is H.

In another embodiment, $R^2$ is —C(O)NHSO$_2$R$^{11}$; $R^{11}$ is alkyl or cycloalkyl; and $R^{21}$ and $R^{22}$ and the nitrogen atoms to which they are attached, join to form a group having the formula:

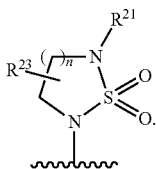

In one embodiment, $R^2$ is —C(O)NHSO$_2$R$^{11}$; $R^{11}$ is alkyl or cycloalkyl; $R^{21}$ is H, alkyl, aryl, cycloalkyl, heterocycloalkyl, heteroaryl or haloalkyl; $R^{22}$ is H; and $R^5$ is other than H.

In another embodiment, $R^2$ is —C(O)NHSO$_2$R$^{11}$; $R^{11}$ is alkyl or cycloalkyl; $R^{21}$ is haloalkyl; $R^{22}$ is H; and $R^5$ is other than H.

In another embodiment, $R^2$ is —C(O)NHSO$_2$R$^{11}$; $R^{11}$ is alkyl or cycloalkyl; $R^{21}$ and $R^{22}$ and the nitrogen atoms to which they are attached, join to form a group having the formula:

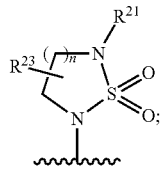

and $R^5$ is other than H.

In one embodiment, $R^1$ is —[C(R$^{12}$)$_2$]$_r$—; $R^2$ is —C(O)NHSO$_2$R$^{11}$ or —C(O)NHSO$_2$N(R$^9$)$_2$; $R^{10}$ is aryl or heteroaryl; $R^{21}$ is H, alkyl, aryl, cycloalkyl, heterocycloalkyl, heteroaryl or haloalkyl; and $R^{22}$ is H.

In another embodiment, $R^1$ is —[C(R$^{12}$)$_2$]$_r$—; $R^2$ is —C(O)NHSO$_2$R$^{11}$ or —C(O)NHSO$_2$N(R$^9$)$_2$; $R^{10}$ is aryl or heteroaryl; $R^{21}$ is haloalkyl; and $R^{22}$ is H.

In another embodiment, $R^1$ is —[C(R$^{12}$)$_2$]$_r$—; $R^2$ is —C(O)NHSO$_2$R$^{11}$ or —C(O)NHSO$_2$N(R$^9$)$_2$; $R^{10}$ is aryl or heteroaryl; and $R^{21}$ and $R^{22}$ and the nitrogen atoms to which they are attached, join to form a group having the formula:

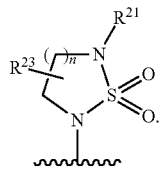

In one embodiment, $R^1$ is —[C(R$^{12}$)$_2$]$_r$—; $R^2$ is —C(O)NHSO$_2$R$^{11}$; $R^{11}$ is alkyl or cycloalkyl; $R^{10}$ is aryl or heteroaryl; $R^{21}$ is H, alkyl, aryl, cycloalkyl, heterocycloalkyl, heteroaryl or haloalkyl; and $R^{22}$ is H.

In another embodiment, $R^1$ is —[C(R$^{12}$)$_2$]$_r$—; $R^2$ is —C(O)NHSO$_2$R$^{11}$; $R^{11}$ is alkyl or cycloalkyl; $R^{10\,1}$ is aryl or heteroaryl; $R^{21}$ is haloalkyl; and $R^{22}$ is H.

In another embodiment, $R^1$ is —[C(R$^{12}$)$_2$]$_r$—; $R^2$ is —C(O)NHSO$_2$R$^{11}$; $R^{11}$ is alkyl or cycloalkyl; $R^{10}$ is aryl or heteroaryl; and $R^{21}$ and $R^{22}$ and the nitrogen atoms to which they are attached, join to form a group having the formula:

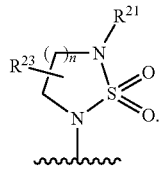

In one embodiment, $R^1$ is —CH$_2$—, —CH$_2$CH$_2$—, —CH(CH$_3$)— or

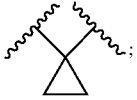

$R^2$ is —C(O)NHSO$_2$R$^{11}$; R$^{11}$ is alkyl or cycloalkyl; R$^{10}$ is aryl or heteroaryl; R$^{21}$ is H, alkyl, aryl, cycloalkyl, heterocycloalkyl, heteroaryl car haloalkyl; and R$^{22}$ is H.

In another embodiment, R$^1$ is —CH$_2$—, —CH$_2$CH$_2$—, —CH(CH$_3$)— or

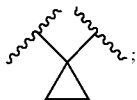 [SMILES: *C1(*)CC1]

$R^2$ is —C(O)NHSO$_2$R$^{11}$; R$^{11}$ is alkyl or cycloalkyl; R$^{10}$ is aryl or heteroaryl; R$^{21}$ is haloalkyl; and R$^{22}$ is H.

In another embodiment, R$^1$ is —CH$_2$—, —CH$_2$CH$_2$—, —CH(CH$_3$)— or

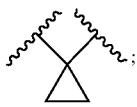

$R^2$ is —C(O)NHSO$_2$R$^{11}$; R$^{11}$ is alkyl or cycloalkyl; R$^{10}$ is aryl or heteroaryl; and R$^{21}$ and R$^{22}$ and the nitrogen atoms to which they are attached, join to form a group having the formula:

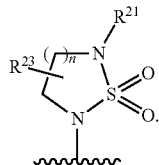

In one embodiment, R$^1$ is —CH$_2$—, —CH$_2$CH$_2$—, —CH(CH$_3$)— or

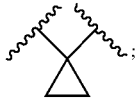 [SMILES: *C1(*)CC1]

$R^2$ is —C(O)NHSO$_2$R$^{11}$; R$^{11}$ is alkyl or cycloalkyl; R$^{10}$ is phenyl, naphthyl, pyridyl, quinolinyl or quinoxalinyl; R$^{21}$ is H, alkyl, aryl, cycloalkyl, heterocycloalkyl, heteroaryl or haloalkyl; and R$^{22}$ is H.

In another embodiment, R$^1$ is —CH$_2$—, —CH$_2$CH$_2$—, —CH(CH$_3$)— or

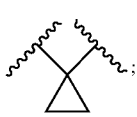 [SMILES: *C1(*)CC1]

$R^2$ is —C(O)NHSO$_2$R$^{11}$; R$^{11}$ is alkyl or cycloalkyl; R$^{10}$ is phenyl, naphthyl, pyridyl, quinolinyl or quinoxalinyl; R$^{21}$ is haloalkyl; and R$^{22}$ is H.

In another embodiment, R$^1$ is —CH$_2$—, —CH$_2$CH$_2$—, —CH(CH$_3$)— or

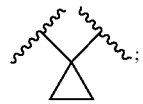

$R^2$ is —C(O)NHSO$_2$R$^{11}$; R$^{11}$ is alkyl or cycloalkyl; R$^{10}$ is phenyl, naphthyl, pyridyl, quinolinyl or quinoxalinyl; and R$^{21}$ and R$^{22}$ and the nitrogen atoms to which they are attached, join to form a group having the formula:

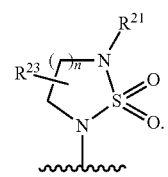

In one embodiment, R$^1$ is —CH$_2$—, —CH$_2$CH$_2$—, —CH(CH$_3$)— or

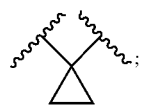

$R^2$ is —C(O)NHSO$_2$R$^{11}$; R$^{11}$ is alkyl or cycloalkyl; R$^{10}$ is:

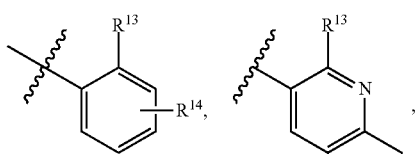

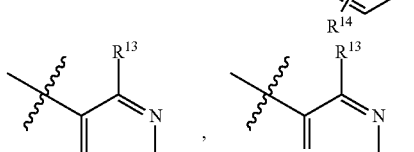

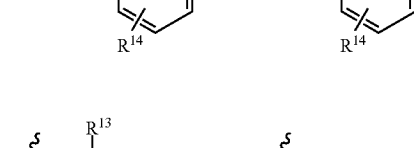

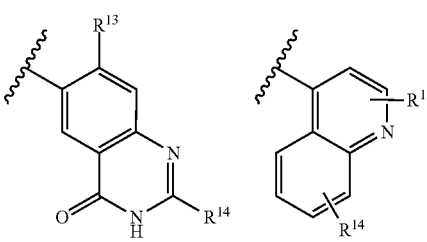

-continued

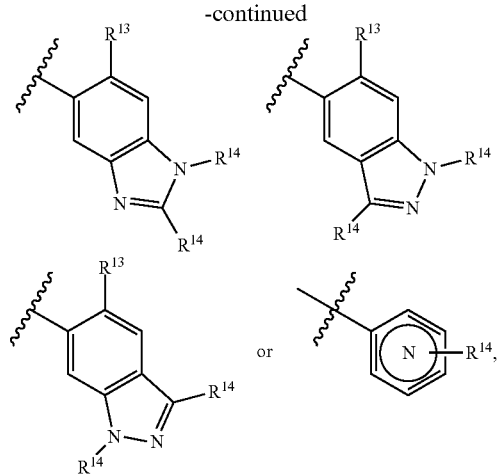

wherein $R^{13}$ is H, F, Br or Cl, and $R^{14}$ represents up to 4 optional and additional substituents, each independently selected from alkyl, cycloalkyl, CF$_3$, —CN, halo, —O-alkyl, —NHSO$_2$-alkyl, —NO$_2$, —C(O)NH$_2$, —C(O)NH-alkyl, —C(O)OH, hydroxy, —NH$_2$, —SO$_2$alkyl, —SO$_2$NHalkyl, —S-alkyl, —CH$_2$NH$_2$, —CH$_2$OH, —SO$_2$NH$_2$, —NHC(O)-alkyl, —C(O)O-alkyl, —C(O)-heterocycloalkyl and heteroaryl; $R^{21}$ is H, alkyl, aryl, cycloalkyl, heterocycloalkyl, heteroaryl or haloalkyl; and $R^{22}$ is H.

In another embodiment, $R^1$ is —CH$_2$—, —CH$_2$CH$_2$—, —CH(CH$_3$)— or

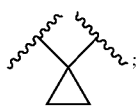;

$R^2$ is —C(O)NHSO$_2$R$^{11}$; $R^{11}$ is alkyl or cycloalkyl; $R^{10}$ is:

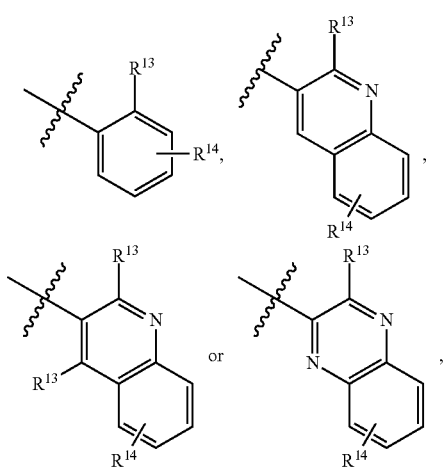

wherein $R^{13}$ is H, F, Br or Cl, and $R^{14}$ represents up to 4 optional and additional substituents, each independently selected from alkyl, cycloalkyl, CF$_3$, —CN, halo, —O-alkyl, —NHSO$_2$-alkyl, —NO$_2$, —C(O)NH$_2$, —C(O)NH-alkyl, —C(O)OH, hydroxy, —NH$_2$, —SO$_2$alkyl, —SO$_2$NHalkyl, —S-alkyl, —CH$_2$NH$_2$, —CH$_2$OH, —SO$_2$NH$_2$, —NHC(O)-alkyl, —C(O)O-alkyl, —C(O)-heterocycloalkyl and heteroaryl; $R^{21}$ is haloalkyl; and $R^{22}$ is H.

In another embodiment, $R^1$ is —CH$_2$—, —CH$_2$CH$_2$—, —CH(CH$_3$)— or

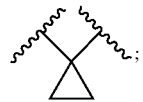;

$R^2$ is —C(O)NHSO$_2$R$^{11}$; $R^{11}$ is alkyl or cycloalkyl; $R^{10}$ is:

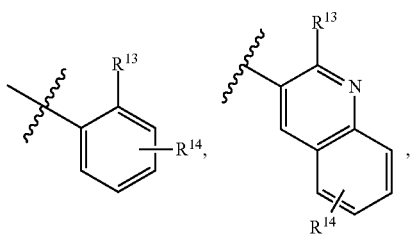

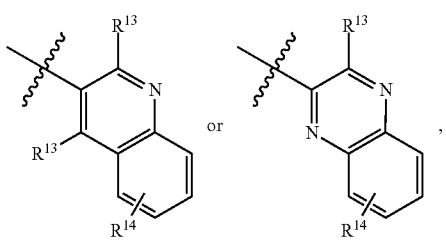

wherein $R^{13}$ is H, F, Br or Cl, and $R^{14}$ represents up to 4 optional and additional substituents, each independently selected from alkyl, cycloalkyl, CF$_3$, —CN, halo, —O-alkyl, —NHSO$_2$-alkyl, —NO$_2$, —C(O)NH$_2$, —C(O)NH-alkyl, —C(O)OH, hydroxy, —NH$_2$, —SO$_2$alkyl, —SO$_2$NHalkyl, —S-alkyl, —CH$_2$NH$_2$, —CH$_2$OH, —SO$_2$NH$_2$, —NHC(O)-alkyl, —C(O)O-alkyl, —C(O)-heterocycloalkyl and heteroaryl; and $R^{21}$ and $R^{22}$ and the nitrogen atoms to which they are attached, join to form a group having the formula:

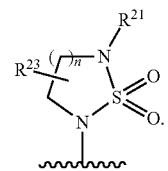

In one embodiment, $R^1$ is —CH$_2$—; $R^2$ is —C(O)NHSO$_2$R$^{11}$; $R^{11}$ is alkyl or cycloalkyl; $R^{10}$ is:

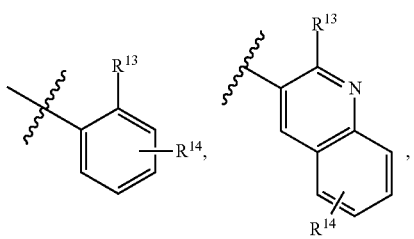

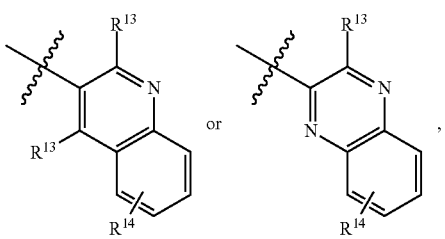 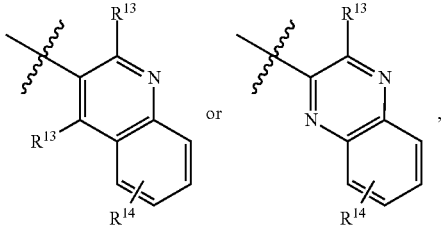

wherein $R^{13}$ is H, F, Br or Cl, and $R^{14}$ represents up to 4 optional and additional substituents, each independently selected from alkyl, cycloalkyl, $CF_3$, —CN, halo, —O-alkyl, —$NHSO_2$-alkyl, —$NO_2$, —$C(O)NH_2$, —C(O)NH-alkyl, —C(O)OH, hydroxy, —$SO_2$alkyl, —$SO_2$NHalkyl, —S-alkyl, —$CH_2NH_2$, —$CH_2OH$, —$SO_2NH_2$, —NHC(O)-alkyl, —C(O)O-alkyl, —C(O)-heterocycloalkyl and heteroaryl; $R^{21}$ is H, alkyl, aryl, cycloalkyl, heterocycloalkyl, heteroaryl or haloalkyl; and $R^{22}$ is H.

In another embodiment, $R^1$ is —$CH_2$—; $R^2$ is —C(O)NHSO$_2R^{11}$; $R^{11}$ is alkyl or cycloalkyl; $R^{10}$ is:

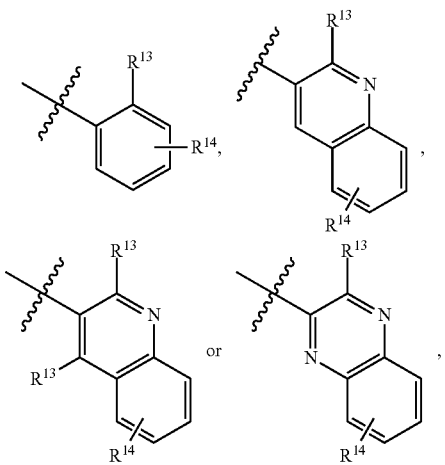

wherein $R^{13}$ is H, F, Br or Cl, and $R^{14}$ represents up to 4 optional and additional substituents, each independently selected from alkyl, cycloalkyl, $CF_3$, —CN, halo, —O-alkyl, —$NHSO_2$-alkyl, —$NO_2$, —$C(O)NH_2$, —C(O)NH-alkyl, —C(O)OH, hydroxy, —$NH_2$, —$SO_2$alkyl, —$SO_2$NHalkyl, —S-alkyl, —$CH_2NH_2$, —$SO_2NH_2$, —NHC(O)-alkyl, —C(O)O-alkyl, —C(O)-heterocycloalkyl and heteroaryl; $R^{21}$ is haloalkyl; and $R^{22}$ is H.

In another embodiment, $R^1$ is —$CH_2$—, $R^2$ is —C(O)NHSO$_2R^{11}$; $R^{11}$ alkyl or cycloalkyl; $R^{10}$ is:

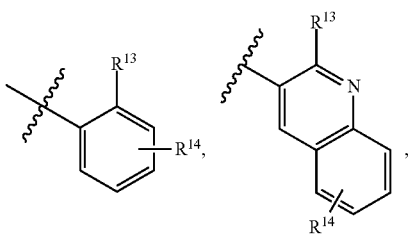

wherein $R^{13}$ is H, Br or Cl, and $R^{14}$ represents up to 4 optional and additional substituents, each independently selected from alkyl, cycloalkyl, $CF_3$, —CN, halo, —O-alkyl, —$NHSO_2$-alkyl, —$NO_2$, —$C(O)NH_2$, —C(O)NH-alkyl, —C(O)OH, hydroxy, —$NH_2$, —$SO_2$alkyl, —$SO_2$NHalkyl, —S-alkyl, —$CH_2NH_2$, —$CH_2OH$, —$SO_2NH_2$, —NHC(O)-alkyl, —C(O)O-alkyl, —C(O)-heterocycloalkyl and heteroaryl; and $R^{21}$ and $R^{22}$ and the nitrogen atoms to which they are attached, join to faith a group having the formula:

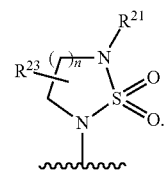

In one embodiment, $R^1$-$R^{10}$ is

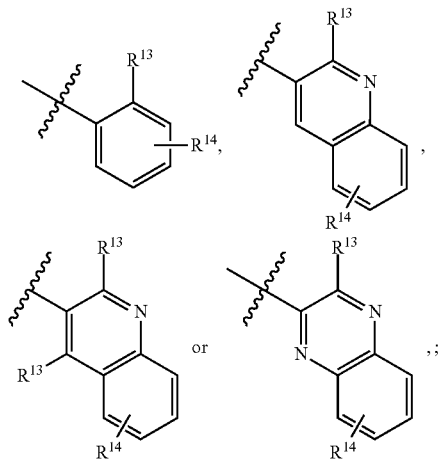

$R^2$ is —C(O)NHSO$_2R^{11}$; $R^{21}$ is H, alkyl, aryl, cycloalkyl, heterocycloalkyl, heteroaryl or haloalkyl; and $R^{22}$ is H.

In another embodiment, $R^1$-$R^{10}$ is

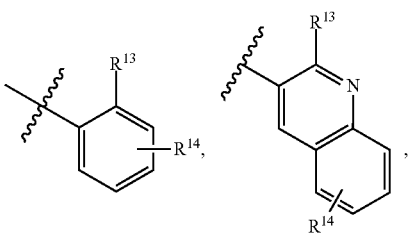

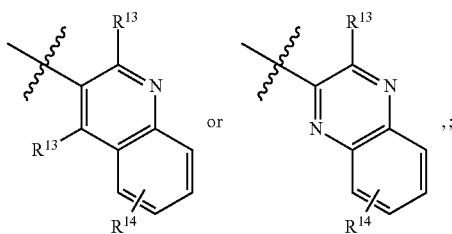

$R^2$ is —C(O)NHSO$_2$R$^{11}$; R$^{21}$ is haloalkyl; and R$^{22}$ is H.

In another embodiment, R$^1$-R$^{10}$ is

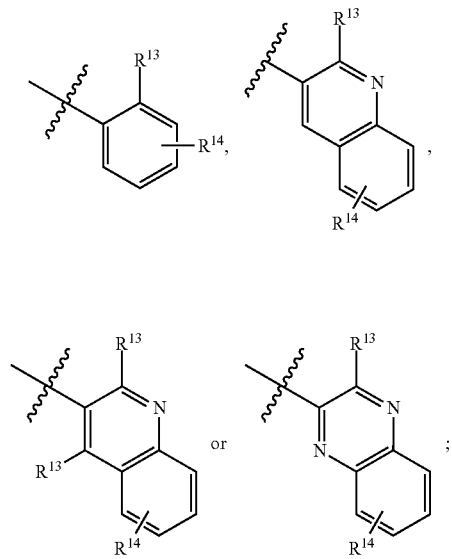

$R^2$ is —C(O)NHSO$_2$R$^{11}$; and R$^{21}$ and R$^{22}$ and the nitrogen atoms to which they are attached, join to form a group having the formula:

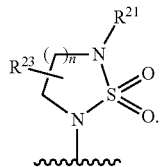

In one embodiment, R$^1$-R$^{10}$ is

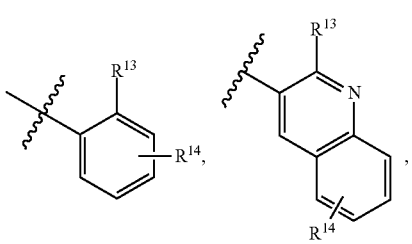

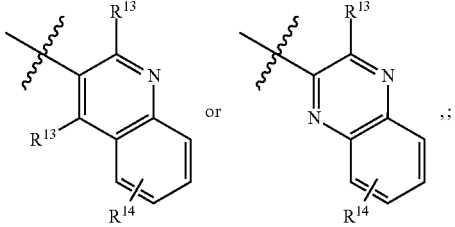

$R^2$ is —C(O)NHSO$_2$R$^{11}$; R$^{11}$ is alkyl; R$^{21}$ is H, alkyl, aryl, cycloalkyl, heterocycloalkyl, heteroaryl or haloalkyl; and R$^{22}$ is H.

In another embodiment, R$^1$-R$^{10}$ is

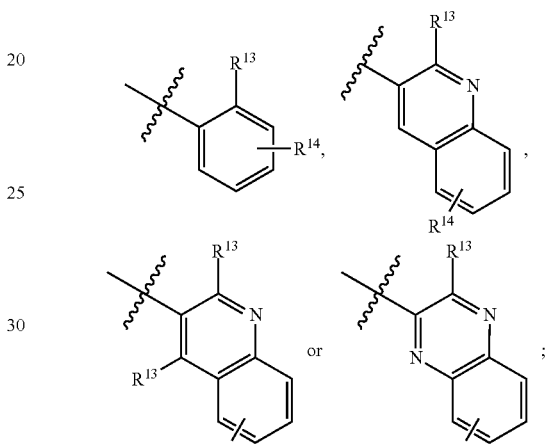

$R^2$ is —C(O)NHSO$_2$R$^{11}$; R$^{11}$ is alkyl; R$^{21}$ is haloalkyl; and R$^{22}$ is H.

In another embodiment, R$^1$-R$^{10}$ is

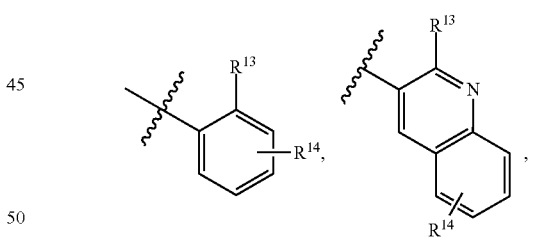

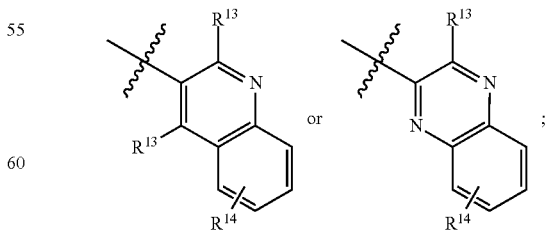

$R^2$ is —C(O)NHSO$_2$R$^{11}$; R$^{11}$ is alkyl; and R$^{21}$ and R$^{22}$ and the nitrogen atoms to which they are attached, join to form a group having the formula:

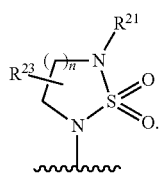

In one embodiment, $R^1$-$R^{10}$ is is benzyl, wherein the phenyl moiety of the benzyl group is optionally substituted with from 1-4 groups independently selected from: halo, —$NH_2$, —$NHSO_2$-alkyl, haloalkyl, methoxy, —O-haloalkyl, —[C($R^{12}$)$_2$]$_q$—NHC(O)NH-alkyl, alkyl, hydroxy, —CN, —C(O)$NH_2$ or —[C($R^{12}$)$_2$]$_q$—$NH_2$; $R^2$ is —C(O)$NHSO_2R^{11}$; $R^{11}$ is alkyl; $R^{21}$ is H, alkyl, aryl, cycloalkyl, heterocycloalkyl, heteroaryl or haloalkyl; and $R^{22}$ is H.

In another embodiment, $R^1$-$R^{10}$ is is benzyl, wherein the phenyl moiety of the benzyl group is optionally substituted with from 1-4 groups independently selected from: halo, —$NH_2$, —$NHSO_2$-alkyl, haloalkyl, methoxy, —O-haloalkyl, —[C($R^{12}$)$_2$]$_q$—NHC(O)NH-alkyl, alkyl, hydroxy, —CN, —C(O)$NH_2$ or —[C($R^{12}$)$_2$]$_q$—$NH_2$; $R^2$ is —C(O)$NHSO_2R^{11}$; $R^{11}$ is alkyl; $R^{21}$ is haloalkyl; and $R^{22}$ is H.

In another embodiment, $R^1$-$R^{10}$ is is benzyl, wherein the phenyl moiety of the benzyl group is optionally substituted with from 1-4 groups independently selected from: halo, —$NH_2$, —$NHSO_2$-alkyl, haloalkyl, methoxy, —O-haloalkyl, —[C($R^{12}$)$_2$]$_q$—NHC(O)NH-alkyl, alkyl, hydroxy, —CN, —C(O)$NH_2$ or —[C($R^{12}$)$_2$]$_q$—$NH_2$; $R^2$ is —C(O)$NHSO_2R^{11}$; $R^{11}$ is alkyl; and $R^{21}$ and $R^{22}$ and the nitrogen atoms to which they are attached, join to form a group having the formula:

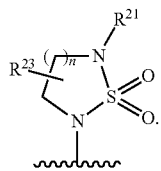

In one embodiment, $R^1$-$R^{10}$ is

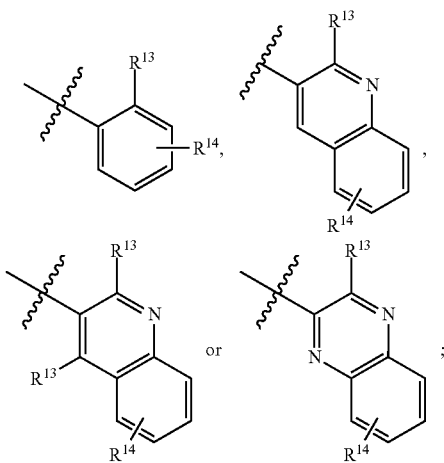

$R^2$ is —C(O)$NHSO_2R^{11}$; $R^4$, $R^5$, $R^6$ and $R^7$ are each independently selected from H, alkyl, —O-alkyl or halo; $R^{11}$ is alkyl; $R^{21}$ is H, alkyl, aryl, cycloalkyl, heterocycloalkyl, heteroaryl or haloalkyl; and $R^{22}$ is H.

In another embodiment, $R^1$-$R^{10}$ is

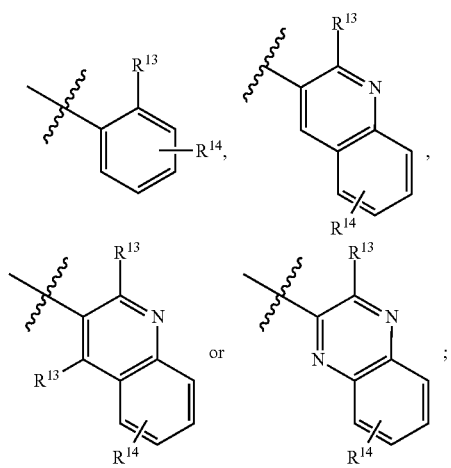

$R^2$ is —C(O)$NHSO_2R^{11}$; $R^4$, $R^5$, $R^6$ and $R^7$ are each independently selected from H, alkyl, —O-alkyl or halo; $R^{11}$ is alkyl; $R^{21}$ is haloalkyl; and $R^{22}$ is H.

In another embodiment, $R^1$-$R^{10}$ is

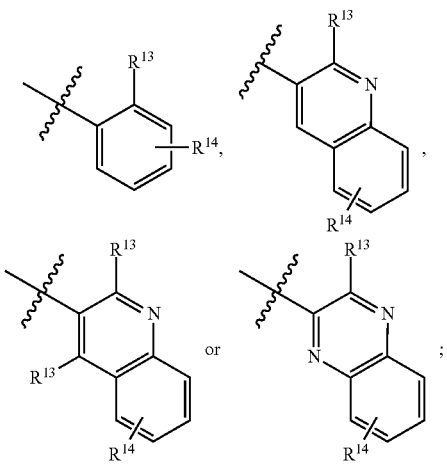

$R^2$ is —C(O)$NHSO_2R^{11}$; $R^4$, $R^5$, $R^6$ and $R^7$ are each independently selected from H, alkyl, —O-alkyl or halo; $R^{11}$ is alkyl; and $R^{21}$ and $R^{22}$ and the nitrogen atoms to which they are attached, join to form a group having the formula:

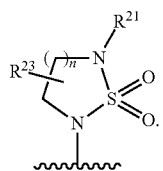

In one embodiment, $R^1$-$R^{10}$ is is benzyl, wherein the phenyl moiety of the benzyl group is optionally substituted with from 1-4 groups independently selected from: halo, —$NH_2$, —$NHSO_2$-alkyl, haloalkyl, methoxy, —O-haloalkyl, —[C($R^{12}$)$_2$]$_q$—NHC(O)NH-alkyl, alkyl, hydroxy, —CN, —C(O)$NH_2$ or —[C($R^{12}$)$_2$]$_q$—$NH_2$; $R^2$ is —C(O)$NHSO_2R^{11}$; $R^4$, $R^5$, $R^6$ and $R^7$ are each independently selected from H, alkyl, —O-alkyl or halo:, $R^{11}$ is alkyl; $R^{21}$ is H, alkyl, aryl, cycloalkyl, heterocycloalkyl, heteroaryl or haloalkyl; and $R^{22}$ is H.

In another embodiment, $R^1$-$R^{10}$ is is benzyl, wherein the phenyl moiety of the benzyl group is optionally substituted with from 1-4 groups independently selected from: halo, —$NH_2$, —$NHSO_2$-alkyl, haloalkyl, methoxy, —O-haloalkyl, —$[C(R^{12})_2]_q$—NHC(O)NH-alkyl, alkyl, hydroxy, —CN, —C(O)$NH_2$ or —$[C(R^{12})_2]_q NH_2$; $R^2$ is —C(O)NHSO$_2R^{11}$; $R^4$, $R^5$, $R^6$ and $R^7$ are each independently selected from H, alkyl, —O-alkyl or halo; $R^{11}$ is alkyl; $R^{21}$ is haloalkyl; and $R^{22}$ is H.

In another embodiment, $R^1$-$R^{10}$ is is benzyl, wherein the phenyl moiety of the benzyl group is optionally substituted with from 1-4 groups independently selected from: halo, —$NH_2$, —$NHSO_2$-alkyl, haloalkyl, methoxy, —O-haloalkyl, —$[C(R^{12})_2]_q$—NHC(O)NH-alkyl, alkyl, hydroxy, —CN, —C(O)$NH_2$ or —$[C(R^{12})_2]_q NH_2$; $R^2$ is —C(O)NHSO$_2R^{11}$; $R^4$, $R^5$, $R^6$ and $R^7$ are each independently selected from H, alkyl, —O-alkyl or halo; $R^{11}$ is alkyl; and $R^{21}$ and $R^{22}$ and the nitrogen atoms to which they are attached, join to form a group having the formula:

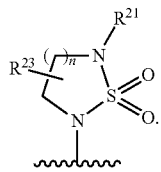

In one embodiment, $R^1$-$R^{10}$ is

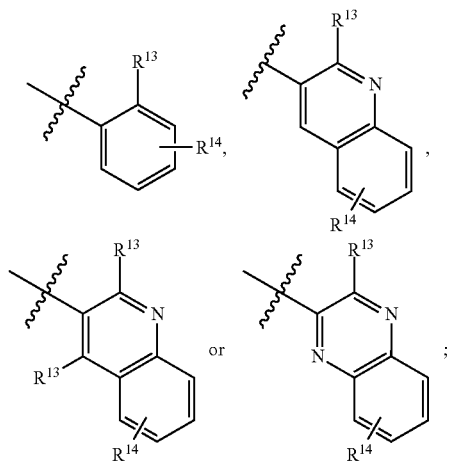

$R^2$ is —C(O)NHSO$_2R^{11}$; $R^4$, $R^6$ and $R^7$ are each H; $R^5$ is H, alkyl, —O-alkyl or halo; $R^{11}$ is alkyl; $R^{21}$ is H, alkyl, aryl, cycloalkyl, heterocycloalkyl, heteroaryl or haloalkyl; and $R^{22}$ is H.

In another embodiment, $R^1$-$R^{10}$ is

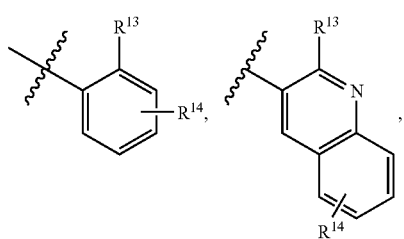

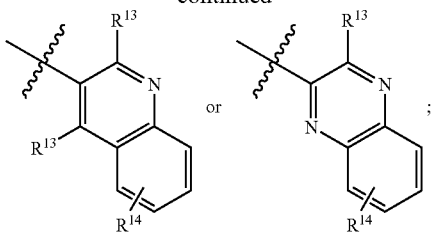

$R^2$ is —C(O)NHSO$_2R^{11}$; $R^4$, $R^6$ and $R^7$ are each H: $R^5$ is alkyl, —O-alkyl or halo; $R^{11}$ is alkyl; $R^{21}$ is haloalkyl; and $R^{22}$ is H.

In another embodiment, $R^1$-$R^{10}$ is

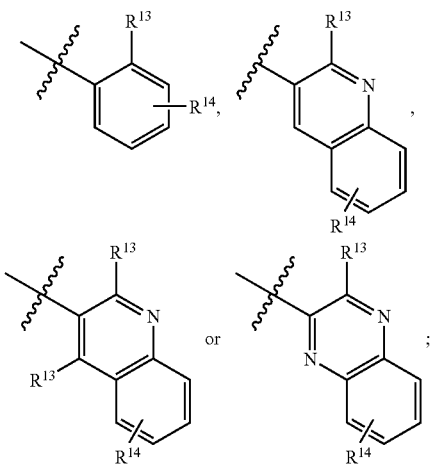

$R^2$ is —C(O)NHSO$_2R^{11}$; $R^4$, $R^6$ and $R^7$ are each H; $R^5$ is H, alkyl, —O-alkyl or halo; $R^{11}$ is alkyl; and $R^{21}$ and $R^{22}$ and the nitrogen atoms to which they are attached, join to form a group having the formula:

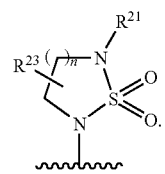

In one embodiment, $R^1$-$R^{10}$ is is benzyl, wherein the phenyl moiety of the benzyl group is optionally substituted with from 1-4 groups independently selected from: halo, —$NH_2$, —$NHSO_2$-alkyl, haloalkyl, methoxy, —O-haloalkyl, —$[C(R^{12})_2]_q$—NHC(O)NH-alkyl, alkyl, hydroxy, —CN, —C(O)$NH_2$ or —$[C(R^{12})_2]_q$—$NH_2$; $R^2$ is —C(O)NHSO$_2R^{11}$; $R^4$, $R^6$ and $R^7$ are each H; $R^5$ is H, alkyl, —O-alkyl or halo; $R^{11}$ is alkyl; $R^{21}$ is H, alkyl, aryl, cycloalkyl, heterocycloalkyl, heteroaryl or haloalkyl; and $R^{22}$ is H.

In another embodiment, $R^1$-$R^{10}$ is is benzyl, wherein the phenyl moiety of the benzyl group is optionally substituted with from 1-4 groups independently selected from: halo, —$NH_2$, —$NHSO_2$-alkyl, haloalkyl, methoxy, —O-haloalkyl, —$[C(R^{12})_2]_q$—NHC(O)NH-alkyl, alkyl, hydroxy, —CN, —C(O)$NH_2$ or —$[C(R^{12})_2]_q$—$NH_2$; $R^2$ is —C(O)NHSO$_2R^{11}$; $R^4$, $R^6$ and $R^7$ are each H; $R^5$ is H, alkyl, —O-alkyl or halo; $R^{11}$ is alkyl; $R^{21}$ is haloalkyl; and $R^{22}$ is H.

In another embodiment, $R^1$-$R^{10}$ is is benzyl, wherein the phenyl moiety of the benzyl group is optionally substituted with from 1-4 groups independently selected from: halo, —$NH_2$, —$NHSO_2$-alkyl, haloalkyl, methoxy, —O-haloalkyl, —$[C(R^{12})_2]_q$—NHC(O)NH-alkyl, alkyl, hydroxy, —CN, —C(O)$NH_2$ or —$[C(R^{12})_2]_q$—$NH_2$; $R^2$ is —C(O)$NHSO_2R^{11}$; $R^4$, $R^6$ and $R^7$ are each H; $R^5$ is H, alkyl, —O-alkyl or halo; $R^{11}$ is alkyl; and $R^{21}$ and $R^{22}$ and the nitrogen atoms to which they are attached, join to form a group having the formula:

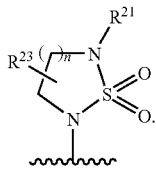

In one embodiment, $R^{21}$ and $R^{22}$ and the nitrogen atoms to which each are attached, join to form group having the formula:

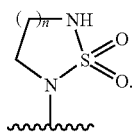

In another embodiment, $R^{21}$ and $R^{22}$ and the nitrogen atoms to which each are attached, join to form a group having the formula:

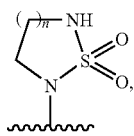

wherein n is 1.

In another embodiment, $R^{21}$ and $R^{22}$ and the nitrogen atoms to which each are attached, join to form a group having the formula:

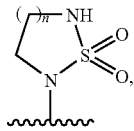

wherein n is 2.

In one embodiment, for the compounds of formula (I), $R^1$, $R^2$, $R^4$, $R^5$, $R^6$, $R^7$, $R^{10}$, $R^{21}$ and $R^{22}$ are selected independently of each other.

In another embodiment, a compound of formula (I) is in purified form.

The 3-Aminosulfonyl Substituted Indole Derivatives of Formula (II)

The present invention also provides 3-Aminosulfonyl Substituted Indole Derivatives having the formula:

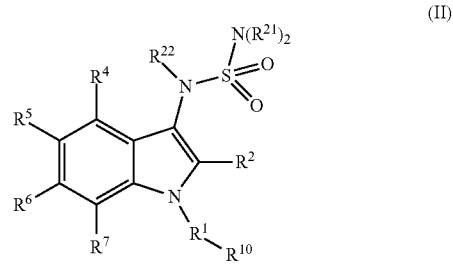

and pharmaceutically acceptable salts, solvates, esters and prodrugs thereof, wherein $R^1$, $R^2$, $R^4$, $R^5$, $R^6$, $R^7$, $R^{10}$, $R^{21}$ and $R^{22}$ are defined above for the compounds of formula (II).

In one embodiment, $R^1$ is bond.
In another embodiment, $R^1$ is —$[C(R^{12})_2]_r$—.
In another embodiment, $R^1$ is —$[C(R^{12})_2]_r$—O—$[C(R^{12})_2]_q$—.
In still another embodiment, $R^1$ is —$[C(R^{12})_2]_r$—$N(R^9)$—$[C(R^{12})_2]_q$—.
In yet another embodiment, $R^1$ is —$[C(R^{12})_2]_q$—CH=CH—$[C(R^{12})_2]_q$—.
In another embodiment, $R^1$ is —$[C(R^{12})_2]_q$—C≡C—$[C(R^{12})_2]_q$—.
In a further embodiment, $R^1$ is —$[C(R^{12})_2]_q$—$SO_2$—$[C(R^{12})_2]_q$—.
In one embodiment, $R^1$ is —$CH_2$—, —$CH_2CH_2$—, —CH($CH_3$)— or

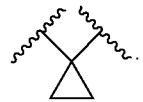 [SMILES: *C1(*)CC1]

In another embodiment, $R^1$ is —$CH_2$—.
In another embodiment, $R^1$ is

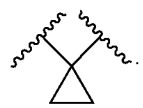 [SMILES: *C1(*)CC1]

In one embodiment, $R^{10}$ is aryl.
In another embodiment, $R^{10}$ is H.
In another embodiment, $R^{10}$ is cycloalkyl.
In another embodiment, $R^{10}$ is cycloalkenyl.
In still another embodiment, $R^{10}$ is heterocycloalkenyl,
In another embodiment, $R^{10}$ is heteroaryl.
In another embodiment, $R^{10}$ is heterocycloalkyl.
In another embodiment, $R^{10}$ is phenyl.
In another embodiment, $R^{10}$ is phenyl, which is substituted with from 1-4 groups independently selected from: halo, —$NH_2$, —$NHSO_2$-alkyl, haloalkyl, methoxy; —O-haloalkyl, —$[C(R^{12})_2]_q$—NHC(O)NH-alkyl, alkyl, hydroxy, —CN, —C(O)$NH_2$ or —$[C(R^{12})_2]_q$—$NH_2$.
In yet another embodiment, $R^{10}$ is pyridyl, In a further embodiment, $R^{10}$ is

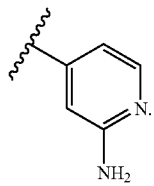 [SMILES: *c1ccnc(N)c1]

In another embodiment, —$R^{10}$ is:

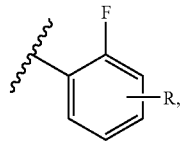

wherein R represents up to 2 optional and additional phenyl substituents, each independently selected from halo, —O-alkyl, alkyl, —$CF_3$, —CN, —$NHSO_2$-alkyl, —$NO_2$, —C(O)$NH_2$, —C(O)OH, —$NH_2$, —$SO_2$-alkyl, —$SO_2$NH-alkyl, —S-alkyl, —$CH_2NH_2$, —$SO_2NH_2$, —NHC(O)-alkyl, —C(O)O-alkyl, —C(O)-heterocycloalkyl and heteroaryl.

In another embodiment, $R^{10}$ is

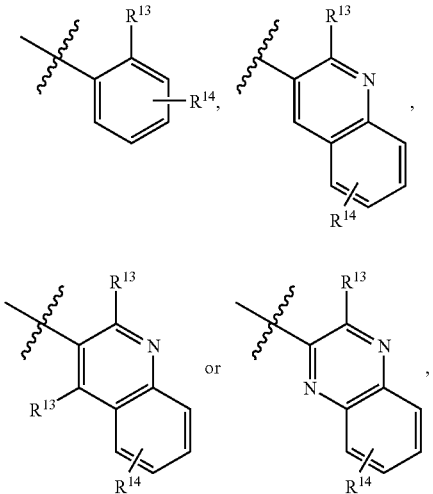

wherein $R^{13}$ is F or Cl and $R^{14}$ represents up to 4 optional and additional substituents, each independently selected from alkyl, cycloalkyl, $CF_3$, —CN, halo, —O-alkyl, —$NHSO_2$-alkyl, —$NO_2$, —C(O)$NH_2$, —C(O)NH-alkyl, —C(O)OH, hydroxy, —$NH_2$, —$SO_2$alkyl, —$SO_2$NHalkyl, —S-alkyl, —$CH_2NH_2$, —$CH_2OH$, —$SO_2NH_2$, —NHC(O)-alkyl, —C(O)O-alkyl, —C(O)-heterocycloalkyl and heteroaryl.

In still another embodiment, $R^1$ is —$CH_2$— or

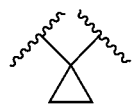

and $R^{10}$ is

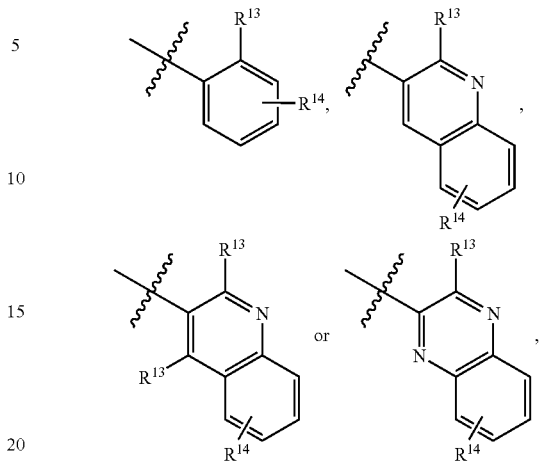

wherein $R^{13}$ is F or Cl and $R^{14}$ represents up to 4 optional and additional substituents, each independently selected from alkyl, cycloalkyl, $CF_3$, —CN, halo, —O-alkyl, —$NHSO_2$-alkyl, —$NO_2$, —C(O)$NH_2$, —C(O)NH-alkyl, —C(O)OH, hydroxy, —$NH_2$, —$SO_2$alkyl, $SO_2$NHalkyl, —S-alkyl, —$CH_2NH_2$, —$CH_2OH$, —$SO_2NH_2$, —NHC(O)-alkyl, —C(O)O-alkyl, —C(O)-heterocycloalkyl and heteroaryl.

In one embodiment, —$R^1$-$R^{10}$ is benzyl.

In another embodiment, —$R^1$-$R^{10}$ is benzyl, wherein the phenyl moiety of the benzyl group is substituted with from 1-4 groups independently selected from: halo, —$NH_2$, —$NHSO_2$-alkyl, haloalkyl, methoxy, —O-haloalkyl, —[C($R^{12}$)$_2$]$_q$—NHC(O)NH-alkyl, alkyl, hydroxy, —CN, —C(O)$NH_2$ or —[C($R^{12}$)$_2$]$_q$—$NH_2$.

In still another embodiment —$R^1$-$R^{10}$ is

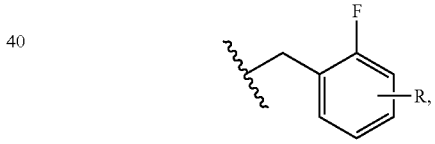

wherein R represents up to 2 optional and additional phenyl substituents, each independently selected from halo, —O-alkyl, alkyl, —$CF_3$, —CN, —$NHSO_2$-alkyl, —$NO_2$, —C(O)$NH_2$, —C(O)OH, —$NH_2$, —$SO_2$-alkyl, —$SO_2$NH-alkyl, —S-alkyl, —$CH_2NH_2$, —SO2$NH_2$, —NHC(O)-alkyl, —C(O)O-alkyl, —C(O)-heterocycloalkyl and heteroaryl.

In another embodiment, —$R^1$-$R^{10}$ is

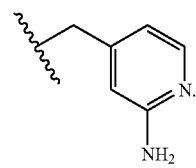 [SMILES: *Cc1ccnc(N)c1]

In still another embodiment, —$R^1$-$R^{10}$ is alkyl.

In yet another embodiment, —$R^1$-$R^{10}$ is —$R^1$-$R^{10}$ is benzyl, wherein the phenyl moiety of the benzyl group is substituted with 1 or 2 fluorine atoms.

In yet another embodiment, —$R^1$-$R^{10}$ is —$R^1$-$R^{10}$ is benzyl, wherein the phenyl moiety of the benzyl group is substituted with 1 or 2 methyl groups.

In yet another embodiment, —R$^1$-R$^{10}$ is —R$^1$-R$^{10}$ is benzyl, wherein the phenyl moiety of the benzyl group is substituted with one fluorine atom and one methyl group.

In another embodiment, —R$^1$-R$^{10}$ is haloalkyl.

In a further embodiment, —R$^1$-R$^{10}$ is —CH$_2$-cycloalkyl.

In one embodiment, R$^2$ is —C(O)R$^9$.

In another embodiment, R$^2$ is —C(O)OR$^9$.

In another embodiment, R$^2$ is —C(O)OCH$_2$OR$^9$.

In still another embodiment, R$^2$ is —C(O)N(R$^9$)$_2$.

In yet another embodiment, R$^2$ is —[C(R$^{12}$)$_2$]$_q$—C(O)OR$^9$.

In another embodiment, R$^2$ is —[C(R$^{12}$)$_2$]$_q$—C(O)N(R$^9$)$_2$.

In a further embodiment, R$^2$ is -alkyl.

In another embodiment, R$^2$ is —[C(R$^{12}$)$_2$]$_q$-aryl.

In another embodiment, R$^2$ is —[C(R$^{12}$)$_2$]$_q$-cycloalkyl.

In still another embodiment, R$^2$ is —[C(R$^{12}$)$_2$]$_q$-cycloalkenyl.

In still another embodiment, R$^2$ is —[C(R$^{12}$)$_2$]$_q$-heterocycloalkyl.

In yet another embodiment, R$^2$ is —[C(R$^{12}$)$_2$]$_q$-heteroaryl.

In another embodiment, R$^2$ is —[C(R$^{12}$)$_2$]$_q$-heterocycloalkenyl.

In a further embodiment, R$^2$ is —C(O)OR$^9$ or —C(O)OCH$_2$OR$^9$.

In another embodiment, R$^2$ is —C(O)OR$^9$ or —C(O)N(R$^9$)$_2$.

In another embodiment, R$^2$ is —C(O)OH, —C(O)NH$_2$, —C(O)O-alkyl, —C(O)O-cycloalkyl, —C(O)NH-alkyl or —C(O)NH-cycloalkyl.

In another embodiment, R$^2$ is —C(O)OH.

In another embodiment, R$^2$ is —C(O)NHR$^9$.

In another embodiment, R$^2$ is —C(O)NH$_2$.

In still another embodiment, R$^2$ is —C(O)R$^9$, —C(O)OR$^9$, —C(O)OCH$_2$OR$^9$, —C(O)N(R$^9$)$_2$, —[C(R$^{12}$)$_2$]$_q$—C(O)OR$^9$, —[C(R$^{12}$)$_2$]$_q$—C(O)N(R$^9$)$_2$ or —[C(R$^{12}$)$_2$]$_q$-heteroaryl wherein a heteroaryl group can be optionally substituted with up to 4 substituents, which are the same or different, and are selected from alkyl, alkenyl, alkynyl, aryl, —[C(R$^{12}$)$_2$]$_q$-cycloalkyl, —[C(R$^{12}$)$_2$]$_q$-cycloalkenyl, —[C(R$^{12}$)$_2$]$_q$-heterocycloalkyl, —[C(R$^{12}$)$_2$]$_q$-heterocycloalkenyl, —[C(R$^{12}$)$_2$]$_q$-heteroaryl, —[C(R$^{12}$)$_2$]$_q$-haloalkyl, —[C(R$^{12}$)$_2$]$_q$-hydroxyalkyl, halo, hydroxy, —OR$^9$, —CN, —[C(R$^{12}$)$_2$]$_q$C(O)R$^8$, —[C(R$^{12}$)$_2$]$_q$—C(O)OR$^9$, —[C(R$^{12}$)$_2$]$_q$—C(O)N(R$^9$)$_2$, —[C(R$^{12}$)$_2$]$_q$—OR$^9$, —[C(R$^{12}$)$_2$]$_q$—N(R$^9$)$_2$, —[C(R$^{12}$)$_2$]$_q$—NHC(O)R$^8$, —[C(R$^{12}$)$_2$]$_q$—NR$^8$C(O)N(R$^9$)$_2$, —[C(R$^{12}$)$_2$]$_q$—NHSO$_2$R$^{11}$, —[C(R$^{12}$)$_2$]$_q$—S(O)$_p$R$^{11}$, —[C(R$^{12}$)$_2$]$_q$—SO$_2$N(R$^9$)$_2$ and —SO$_2$N(R$^9$)C(O)N(R$^9$)$_2$.

In one embodiment, R$^4$ is H.

In another embodiment, R$^4$ is H or F.

In another embodiment, R$^4$ is F.

In another embodiment, R$^5$ is H.

In another embodiment, R$^6$ is H.

In another embodiment, R$^6$ is H or F.

In another embodiment, R$^6$ is F.

In still another embodiment, R$^7$ is H.

In another embodiment, R$^4$ and R$^7$ are each H.

In yet another embodiment, R$^4$, R$^6$ and R$^7$ are each H.

In another embodiment, R$^4$, R$^5$, R$^6$ and R$^7$ are each H.

In a further embodiment, R$^4$, R$^6$ and R$^7$ are each H and R$^5$ is other than H.

In another embodiment, R$^4$, R$^6$ and R$^7$ are each H and R$^5$ is halo.

In another embodiment, R$^4$, R$^6$ and R$^7$ are each H and R$^5$ is Cl.

In still another embodiment, R$^4$, R$^6$ and R$^7$ are each H and R$^5$ is alkyl.

In another embodiment, R$^4$, R$^6$ and R$^7$ are each H and R$^5$ is halo.

In another embodiment, R$^4$, R$^6$ and R$^7$ are each H and R$^5$ is methyl.

In a further embodiment, R$^4$, R$^6$ and R$^7$ are each H and R$^5$ is Cl.

In another embodiment, R$^4$ and R$^7$ are each H and and R$^5$ and R$^6$ are other than H.

In another embodiment, R$^5$ is other than H.

In still another embodiment, R$^5$ is alkyl.

In yet another embodiment, R$^5$ is halo.

In another embodiment, R$^5$ is Cl.

In still another embodiment, R$^5$ is methyl.

In another embodiment, R$^5$ is ethyl.

In another embodiment, R$^6$ is H.

In another embodiment, R$^6$ is other than H.

In a further embodiment, R$^6$ is alkyl.

In yet another embodiment, R$^6$ is halo.

In still another embodiment, R$^6$ is methyl.

In another embodiment, R$^6$ is F.

In one embodiment, R$^4$ is H or F; R$^5$ is methyl or ethyl; R$^6$ is H or F; and R$^7$ is H.

In one embodiment, R$^{21}$ is haloalkyl.

In another embodiment, R$^{21}$ is H.

In another embodiment, R$^{21}$ is alkyl.

In still another embodiment, R$^{21}$ is aryl.

In another embodiment, R$^{21}$ is cycloalkyl.

In another embodiment, R$^{21}$ is heterocycloalkyl.

In yet another embodiment, R$^{21}$ is heteroaryl.

In another embodiment, R$^{21}$ is haloalkyl.

In further embodiment, R$^{21}$ is —(CH$_2$)$_s$-halo, wherein s is an integer ranging from 1 to 6.

In another embodiment, R$^{21}$ is —(CH$_2$)$_2$-halo.

In still another embodiment, R$^{21}$ is —(CH$_2$)$_3$-halo.

In another embodiment, R$^{21}$ is -alkylene-Cl.

In another embodiment, R$^{21}$ is —(CH$_2$)$_s$-Cl, wherein s is an integer ranging from 1 to 6.

In yet another embodiment, R$^{21}$ is —(CH$_2$)$_2$—Cl.

In another embodiment, R$^{21}$ is —(CH$_2$)$_3$—Cl.

In one embodiment, R$^{22}$ is H.

In another embodiment, R$^{22}$ is alkyl.

In still another embodiment, R$^{22}$ is aryl.

In another embodiment, R$^{22}$ is cycloalkyl.

In another embodiment, R$^{22}$ is heterocycloalkyl.

In yet another embodiment, R$^{22}$ is heteroaryl.

In another embodiment, R$^{22}$ is haloalkyl.

In one embodiment, R$^{21}$ is haloalkyl and R$^{22}$ is H.

In another embodiment, R$^{21}$ is —(CH$_2$)$_s$-halo, wherein s is an integer ranging from 1 to 6, and R$^{22}$ is H.

In another embodiment, R$^{21}$ is —(CH$_2$)$_s$—Cl, wherein s is an integer ranging from 1 to 6, and R$^{22}$ is H.

In one embodiment, R$^{21}$ and R$^{22}$ and the nitrogen atoms to which they are attached, join to form a group having the formula:

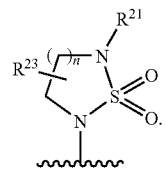

In another embodiment, R$^{21}$ and R$^{22}$ and the nitrogen atoms to which they are attached, join to form a group having the formula:

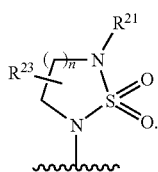

In another embodiment, $R^{21}$ and $R^{22}$ and the nitrogen atoms to which they are attached, join to form a group having the formula:

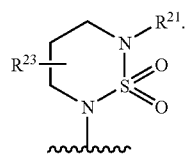

In one embodiment, $R^2$ is —C(O)OR$^9$ or —C(O)N(R$^9$)$_2$; $R^{21}$ is H, alkyl, aryl, cycloalkyl, heterocycloalkyl, heteroaryl or haloalkyl; and $R^{22}$ is H.

In one embodiment, $R^2$ is —C(O)OR$^9$ or —C(O)N(R$^9$)$_2$; $R^{21}$ is haloalkyl; and $R^{22}$ is H.

In one embodiment, $R^2$ is —C(O)OR$^9$ or —C(O)N(R$^9$)$_2$; and $R^{21}$ and $R^{22}$ and the nitrogen atoms to which they are attached, join to form a group having the formula:

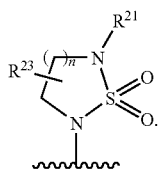

In one embodiment, $R^2$ is —C(O)OR$^9$ or —C(O)N(R$^9$)$_2$; each occurrence of $R^9$ is independently H or alkyl; $R^{21}$ is H, alkyl, aryl, cycloalkyl, heterocycloalkyl, heteroaryl or haloalkyl; and $R^{22}$ is H.

In another embodiment, $R^2$ is —C(O)OR$^9$ or —C(O)N(R$^9$)$_2$; each occurrence of $R^9$ is independently H or alkyl; $R^{21}$ is haloalkyl; and $R^{22}$ is H.

In another embodiment, $R^2$ is —C(O)OR$^9$ or —C(O)N(R$^9$)$_2$; each occurrence of $R^9$ is independently H or alkyl; and $R^{21}$ and $R^{22}$ and the nitrogen atoms to which they are attached, join to form a group having the formula:

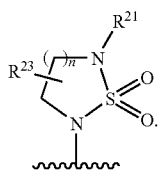

In one embodiment, $R^2$ is —C(O)OR$^9$ or —C(O)N(R$^9$)$_2$; each occurrence of $R^9$ is independently H or alkyl; $R^{21}$ is H, alkyl, aryl, cycloalkyl, heterocycloalkyl, heteroaryl or haloalkyl; $R^{22}$ is H; and $R^5$ is other than H.

In another embodiment, $R^2$ is —C(O)OR$^9$ or —C(O)N(R$^9$)$_2$; each occurrence of $R^9$ is independently H or alkyl; $R^{21}$ is haloalkyl; $R^{22}$ is H; and $R^5$ is other than H.

In another embodiment, $R^2$ is —C(O)OR$^9$ or —C(O)N(R$^9$)$_2$; each occurrence of $R^9$ is independently H or alkyl; $R^{21}$ and $R^{22}$ and the nitrogen atoms to which they are attached, join to form a group having the formula:

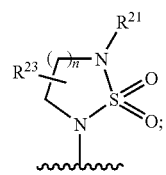

and $R^5$ is other than H.

In one embodiment, $R^1$ is —[C(R$^{12}$)$_2$]$_r$—; $R^2$ is —C(O)OR$^9$ or —C(O)N(R$^9$)$_2$; $R^{10}$ is aryl or heteroaryl; $R^{21}$ is H, alkyl, aryl, cycloalkyl, heterocycloalkyl, heteroaryl or haloalkyl; and $R^{22}$ is H.

In another embodiment, $R^1$ is —[C(R$^{12}$)$_2$]$_r$—; $R^2$ is —C(O)OR$^9$ or —C(O)N(R$^9$)$_2$; $R^{10}$ is aryl or heteroaryl; $R^{21}$ is haloalkyl; and $R^{22}$ is H.

In another embodiment, $R^1$ is —[C(R$^{12}$)$_2$]$_r$—; $R^2$ is —C(O)OR$^9$ or —C(O)N(R$^9$)$_2$; $R^{10}$ is aryl or heteroaryl; and $R^{21}$ and $R^{22}$ and the nitrogen atoms to which they are attached, join to foam a group having the formula:

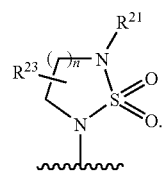

In one embodiment, $R^1$ is —[C(R$^{12}$)$_2$]$_r$—; $R^2$ is —C(O)OR$^9$ or —C(O)N(R$^9$)$_2$; $R^{10}$ is phenyl, naphthyl, pyridyl, quinolinyl or quinoxalinyl; $R^{21}$ is H, alkyl, aryl, cycloalkyl, heterocycloalkyl, heteroaryl or haloalkyl; and $R^{22}$ is H.

In another embodiment, $R^1$ is —[C(R$^{12}$)$_2$]$_r$—; $R^2$ is —C(O)OR$^9$ or —C(O)N(R$^9$)$_2$; $R^{10}$ is phenyl, naphthyl, pyridyl, quinolinyl or quinoxalinyl; $R^{21}$ is haloalkyl; and $R^{22}$ is H.

In another embodiment, $R^1$ is —[C(R$^{12}$)$_2$]$_r$—; $R^2$ is —C(O)OR$^9$ or —C(O)N(R$^9$)$_2$; $R^{10}$ is phenyl, naphthyl, pyridyl, quinolinyl or quinoxalinyl; and $R^{21}$ and $R^{22}$ and the nitrogen atoms to which they are attached, join to form a group having the formula:

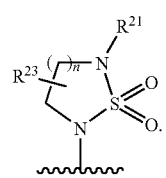

In one embodiment, R¹ is —[C(R¹²)₂]$_r$—; R² is —C(O)OR⁹ or —C(O)N(R⁹)₂; R¹⁰ is:

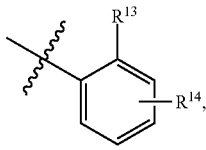 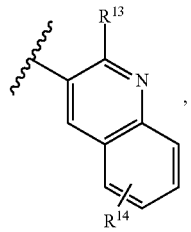

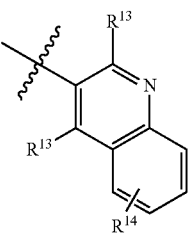 or 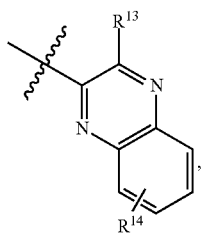, wherein R¹³ is H, F, Br or Cl, and R¹⁴ represents up to 4 optional and additional substituents, each independently selected from alkyl, cycloalkyl, CF₃, —CN, halo, —O-alkyl, —NHSO₂-alkyl, —NO₂, —C(O)NH₂, —C(O)NH-alkyl, —C(O)OH, hydroxy, —NH₂, —SO₂alkyl, —SO₂NHalkyl, —S-alkyl, —CH₂NH₂, —CH₂OH, —SO₂NH₂, —NHC(O)-alkyl, —C(O)O-alkyl, —C(O)-heterocycloalkyl and heteroaryl; R²¹ is H, alkyl, aryl, cycloalkyl, heterocycloalkyl, heteroaryl or haloalkyl; and R²² is H.

In another embodiment, R¹ is —[C(R¹²)₂]$_r$—; R² is —C(O)OR⁹ or —C(O)N(R⁹)₂; R¹⁰ is:

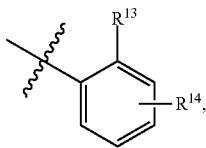 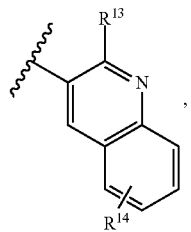

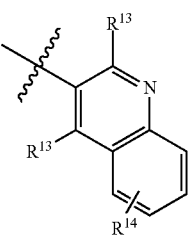 or 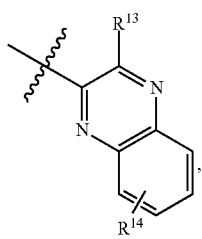, wherein R¹³ is H, F, Br or Cl, and R¹⁴ represents up to 4 optional and additional substituents, each independently selected from alkyl, cycloalkyl, CF₃, —CN, halo, —O-alkyl, —NHSO₂-alkyl, —NO₂, —C(O)NH₂, —C(O)NH-alkyl, —C(O)OH, hydroxy, —NH₂, —SO₂alkyl, —SO₂NHalkyl, —S-alkyl, —CH₂NH₂, —CH₂OH, —SO₂NH₂, —NHC(O)-alkyl, —C(O)O-alkyl, —C(O)-heterocycloalkyl and heteroaryl; R²¹ is haloalkyl; and R²² is H.

In another embodiment, R¹ is —[C(R¹²)₂]$_r$—; R² is —C(O)OR⁹ or —C(O)N(R⁹)₂; R¹⁰ is:

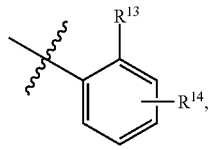 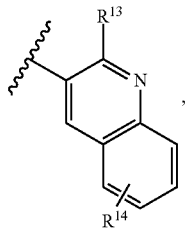

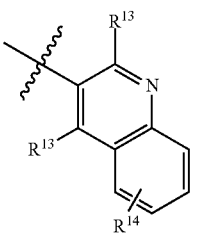 or 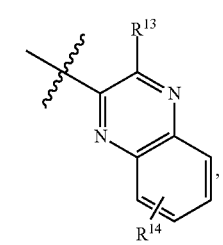, wherein R¹³ is H, F, Br or Cl, and R¹⁴ represents up to 4 optional and additional substituents, each independently selected from alkyl, cycloalkyl, CF₃, —CN, halo, —O-alkyl, —NHSO₂-alkyl, —NO₂, —C(O)NH₂, —C(O)NH-alkyl, —C(O)OH, hydroxy, —NH₂, —SO₂alkyl, —SO₂NHalkyl, —S-alkyl, —CH₂NH₂, —CH₂OH, —SO₂NH₂, —NHC(O)-alkyl, —C(O)O-alkyl, —C(O)-heterocycloalkyl and heteroaryl; and R²¹ and R²² and the nitrogen atoms to which they are attached, join to form a group having the formula:

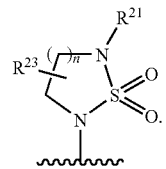

In one embodiment, R¹ is —CH₂—, —CH₂CH₂—, —CH(CH₃)— or

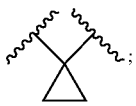 [SMILES: *C1(*)CC1];

R² is —C(O)OR⁹ or —C(O)N(R⁹)₂; R¹⁰ is aryl or heteroaryl; R²¹ is H, alkyl, aryl, cycloalkyl, heterocycloalkyl, heteroaryl or haloalkyl; and R²² is H.

In another embodiment, R¹ is —CH₂—, —CH₂CH₂—, —CH(CH₃)— or

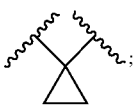;

R² is —C(O)OR⁹ or —C(O)N(R⁹)₂; R¹⁰ is aryl or heteroaryl; R²¹ is haloalkyl; and R²² is H.

In another embodiment, R$^1$ is —CH$_2$—, —CH$_2$CH$_2$—, —CH(CH$_3$)— or

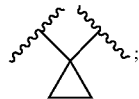 [SMILES: *C1(*)CC1];

R$^2$ is —C(O)OR$^9$ or —C(O)N(R$^9$)$_2$; R$^{10}$ is aryl or heteroaryl; and R$^{21}$ and R$^{22}$ and the nitrogen atoms to which they are attached, join to form a group having the formula;

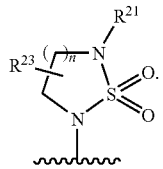

In one embodiment, R$^1$ is —CH$_2$—, —CH$_2$CH$_2$—, —CH(CH$_3$)— or

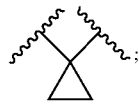 [SMILES: *C1(*)CC1];

R$^2$ is —C(O)OR$^9$ or —C(O)N(R$^9$)$_2$; R$^{10}$ is phenyl, naphthyl, pyridyl, quinolinyl or quinoxalinyl; R$^{21}$ is H, alkyl, aryl, cycloalkyl, heterocycloalkyl, heteroaryl or haloalkyl; and R$^{22}$ is H.

In another embodiment, R$^1$ is —CH$_2$—, —CH$_2$CH$_2$—, —CH(CH$_3$)— or

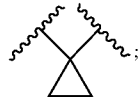 [SMILES: *C1(*)CC1];

R$^2$ is —C(O)OR$^9$ or —C(O)N(R)$_2$; R$^{10}$ is phenyl, naphthyl, pyridyl, quinolinyl or quinoxalinyl; R$^{21}$ is haloalkyl; and R$^{22}$ is H.

In another embodiment, R$^1$ is —CH$_2$—, —CH$_2$CH$_2$—, —CH(CH$_3$)— or

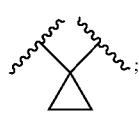 [SMILES: *C1(*)CC1];

R$^2$ is —C(O)OR$^9$ or —C(O)N(R$^9$)$_2$; R$^{10}$ is phenyl, naphthyl, pyridyl, quinolinyl or quinoxalinyl; and R$^{21}$ and R$^{22}$ and the nitrogen atoms to which they are attached, join to form a group having the formula:

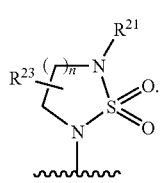

In one embodiment, R$^1$ is —CH$_2$—, —CH$_2$CH$_2$—, —CH(CH$_3$)— or

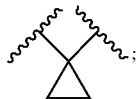;

R$^2$ is —C(O)OR$^9$ or —C(O)N(R$^9$)$_2$; R$^{10}$ is:

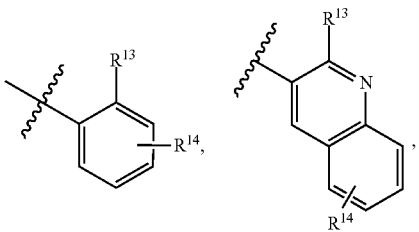

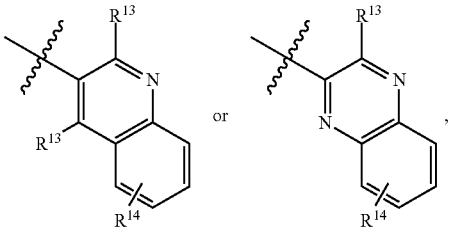

wherein R$^{13}$ is H, F, Br or Cl, and R$^{14}$ represents up to 4 optional and additional substituents, each independently selected from alkyl, cycloalkyl, CF$_3$, —CN, halo, —O-alkyl, —NHSO$_2$-alkyl, —NO$_2$, —C(O)NH$_2$, —C(O)NH-alkyl, —C(O)OH, hydroxy, —NH$_2$, —SO$_2$alkyl, —SO$_2$NHalkyl, —S-alkyl, —CH$_2$NH$_2$, —CH$_2$OH, —SO$_2$NH$_2$, —NHC(O)-alkyl, —C(O)O-alkyl, —C(O)-heterocycloalkyl and heteroaryl; R$^{21}$ is H, alkyl, aryl, cycloalkyl, heterocycloalkyl, heteroaryl or haloalkyl; and R$^{22}$ is H.

In another embodiment, R$^1$ is —CH$_2$—, —CH$_2$CH$_2$—, —CH(CH$_3$)— or

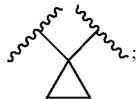;

R$^2$ is —C(O)OR$^9$ or —C(O)N(R$^9$)$_2$; R$^{10}$ is:

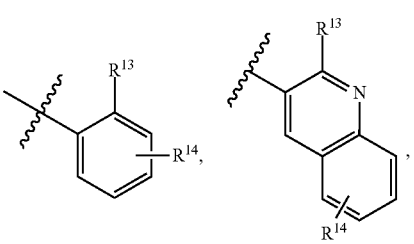

-continued

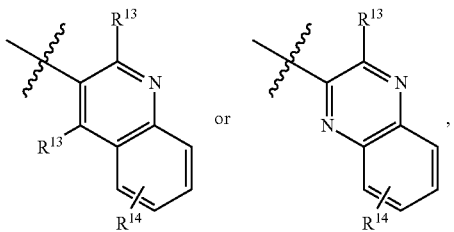

wherein $R^{13}$ is H, F, Br or Cl, and $R^{14}$ represents up to 4 optional and additional substituents, each independently selected from alkyl, cycloalkyl, $CF_3$, —CN, halo, —O-alkyl, —$NHSO_2$-alkyl, —$NO_2$, —$C(O)NH_2$, —C(O)NH-alkyl, —C(O)OH, hydroxy, —$NH_2$, —$SO_2$alkyl, —$SO_2$NHalkyl, —S-alkyl, —$CH_2NH_2$, —$CH_2OH$, —$SO_2NH_2$, —NHC(O)-alkyl, —C(O)O-alkyl, —C(O)-heterocycloalkyl and heteroaryl; $R^{21}$ is haloalkyl; and $R^{22}$ is H.

In another embodiment, $R^1$ is —$CH_2$—, —$CH_2CH_2$—, —$CH(CH_3)$— or

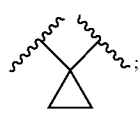 [SMILES: *C1(*)CC1]

$R^2$ is —$C(O)OR^9$ or —$C(O)N(R^9)_2$; $R^{10}$ is:

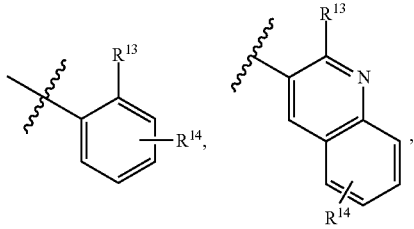

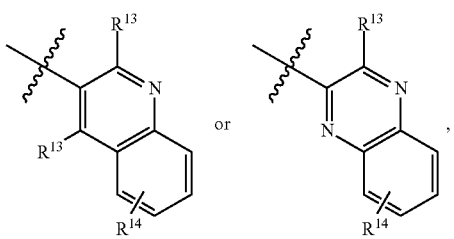

wherein $R^{13}$ is H, F, Br or Cl, and $R^{14}$ represents up to 4 optional and additional substituents, each independently selected from alkyl, cycloalkyl, $CF_3$, —CN, halo, —O-alkyl, —$NHSO_2$-alkyl, —$NO_2$, —$C(O)NH_2$, —C(O)NH-alkyl, —C(O)OH, hydroxy, —$NH_2$, —$SO_2$alkyl, —$SO_2$NHalkyl, —S-alkyl, —$CH_2NH_2$, —$CH_2OH$, —$SO_2NH_2$, —NHC(O)-alkyl, —C(O)O-alkyl, —C(O)-heterocycloalkyl and heteroaryl; and $R^{21}$ and $R^{22}$ and the nitrogen atoms to which they are attached, join to form a group having the formula:

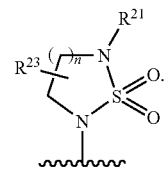

In one embodiment, $R^1$ is —$CH_2$—; $R^2$ is —$C(O)OR^9$ or —$C(O)N(R^9)_2$; $R^{10}$ is aryl or heteroaryl; $R^{21}$ is H, alkyl, aryl, cycloalkyl, heterocycloalkyl, heteroaryl or haloalkyl; and $R^{22}$ is H.

In another embodiment, $R^1$ is —$CH_2$—; $R^2$ is —$C(O)OR^9$ or —$C(O)N(R^9)_2$; $R^{11}$ is alkyl or cycloalkyl; $R^{10}$ is aryl or heteroaryl; $R^{21}$ is haloalkyl; and $R^{22}$ is H.

In another embodiment, $R^1$ is —$CH_2$—; $R^2$ is —$C(O)OR^9$ or —$C(O)N(R^9)_2$; $R^{11}$ is alkyl or cycloalkyl; $R^{10}$ is aryl or heteroaryl; and $R^{21}$ and $R^{22}$ and the nitrogen atoms to which they are attached, join to form a group having the formula:

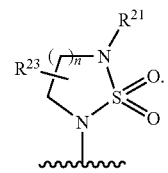

In one embodiment, $R^1$ is —$CH_2$—; $R^2$ is —$C(O)OR^9$ or —$C(O)N(R^9)_2$; $R^{10}$ is phenyl, naphthyl, pyridyl, quinolinyl or quinoxalinyl; $R^{21}$ is H, alkyl, aryl, cycloalkyl, heterocycloalkyl, heteroaryl or haloalkyl; and $R^{22}$ is H.

In another embodiment, $R^1$ is —$CH_2$—; $R^2$ is —$C(O)OR^9$ or —$C(O)N(R^9)_2$; $R^{10}$ is phenyl, naphthyl, pyridyl, quinolinyl or quinoxalinyl; $R^{21}$ is haloalkyl; and $R^{22}$ is H.

In another embodiment. $R^1$ is —$CH_2$—; $R^2$ is —$C(O)OR^9$ or —$C(O)N(R^9)_2$; $R^{10}$ is phenyl, naphthyl, pyridyl, quinolinyl or quinoxalinyl; and $R^{21}$ and $R^{22}$ and the nitrogen atoms to which they are attached, join to form a group having the formula:

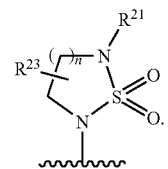

In one embodiment $R^1$ is —$CH_2$—; $R^2$ is —$C(O)OR^9$ or —$C(O)N(R^9)_2$; $R^{10}$ is:

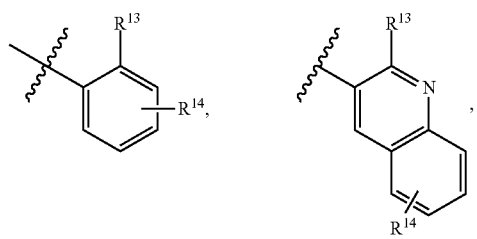

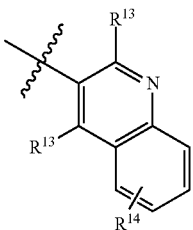 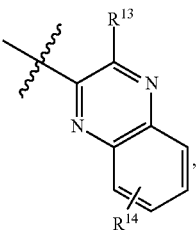 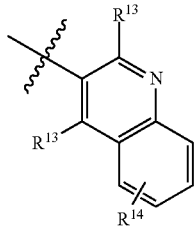 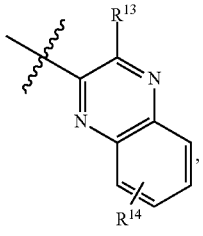

wherein $R^{13}$ is H, F, Br or Cl, and $R^{14}$ represents up to 4 optional and additional substituents, each independently selected from alkyl, cycloalkyl, $CF_3$, —CN, halo, —O-alkyl, —$NHSO_2$-alkyl, —$NO_2$, —C(O)$NH_2$, —C(O)NH-alkyl, —C(O)OH, hydroxy, —$NH_2$, —$SO_2$alkyl, —$SO_2$NHalkyl, —S-alkyl, —$CH_2NH_2$, —$CH_2$OH, —$SO_2NH_2$, —NHC(O)-alkyl, —C(O)O-alkyl, —C(O)-heterocycloalkyl and heteroaryl; $R^{21}$ is H, alkyl, aryl, cycloalkyl, heterocycloalkyl, heteroaryl or haloalkyl; and $R^{22}$ is H.

In another embodiment, $R^1$ is —$CH_2$—; $R^2$ is —C(O)$OR^9$ or —C(O)N($R^9$)$_2$; $R^{10}$ is:

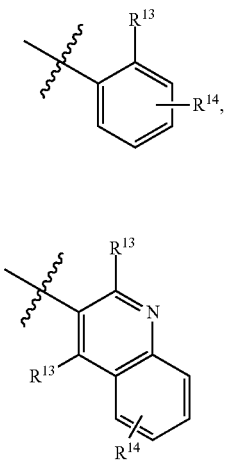 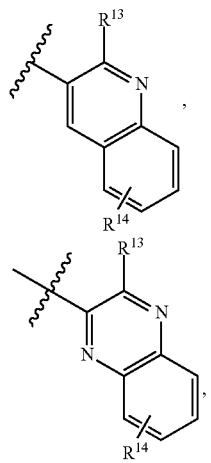

wherein $R^{13}$ is H, F, Br or Cl, and $R^{14}$ represents up to 4 optional and additional substituents, each independently selected from alkyl, cycloalkyl, $CF_3$, —CN, halo, —O-alkyl, —$NHSO_2$-alkyl, —$NO_2$, —C(O)$NH_2$, —C(O)NH-alkyl, —C(O)OH, hydroxy, —$NH_2$, —$SO_2$alkyl, —$SO_2$NHalkyl, —S-alkyl, —$CH_2NH_2$, —$CH_2$OH, —$SO_2NH_2$, —NHC(O)-alkyl, —C(O)O-alkyl, —C(O)-heterocycloalkyl and heteroaryl; $R^{21}$ is haloalkyl; and $R^{22}$ is H.

In another embodiment, $R^1$ is —$CH_2$—; $R^2$ is —C(O)$OR^9$ or —C(O)N($R^9$)$_2$; $R^{10}$ is:

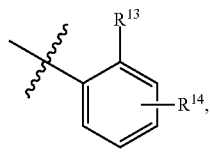 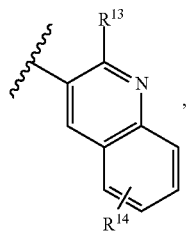

wherein $R^{13}$ is H, F, Br or Cl, and $R^{14}$ represents up to 4 optional and additional substituents, each independently selected from alkyl, cycloalkyl, —CN, halo, —O-alkyl, —$NHSO_2$-alkyl, —$NO_2$, —C(O)$NH_2$, —C(O)NH-alkyl, —C(O)OH, hydroxy, —$NH_2$, —$SO_2$alkyl, —$SO_2$NHalkyl, —S-alkyl, —$CH_2NH_2$, —$CH_2$OH, —$SO_2NH_2$, —NHC(O)-alkyl, —C(O)O-alkyl, —C(O)-heterocycloalkyl and heteroaryl; and $R^{21}$ and $R^{22}$ and the nitrogen atoms to which they are attached, join to form a group having the formula:

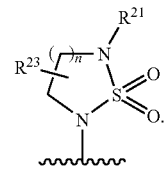

In one embodiment, $R^1$ is —$CH_2$; $R^2$ is —C(O)$OR^9$ or —C(O)N($R^9$)$_2$; each occurrence of $R^9$ is independently H or alkyl; $R^{10}$ is aryl or heteroaryl; $R^{21}$ is H, alkyl, aryl, cycloalkyl, heterocycloalkyl, heteroaryl or haloalkyl; and $R^{22}$ is H.

In another embodiment, $R^1$ is —$CH_2$—; $R^2$ is —C(O)$OR^9$ or —C(O)N($R^9$)$_2$; each occurrence of $R^9$ is independently H or alkyl; $R^{11}$ is alkyl or cycloalkyl; $R^{10}$ is aryl or heteroaryl; $R^{21}$ is haloalkyl; and $R^{22}$ is H.

In another embodiment, $R^1$ is —$CH_2$—; $R^2$ is —C(O)$OR^9$ or —C(O)N($R^9$)$_2$; each occurrence of $R^9$ is independently H or alkyl; $R^{11}$ is alkyl or cycloalkyl; $R^{10}$ is aryl or heteroaryl; and $R^{21}$ and $R^{22}$ and the nitrogen atoms to which they are attached, join to form a group having the formula:

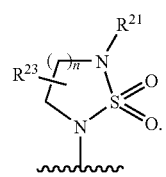

In one embodiment, $R^1$ is —$CH_2$—; $R^2$ is —C(O)$OR^9$ or —C(O)N($R^9$)$_2$; each occurrence of $R^9$ is independently H or alkyl; $R^{10}$ is phenyl, naphthyl, pyridyl, quinolinyl or quinoxalinyl; $R^{21}$ is H, alkyl, aryl, cycloalkyl, heterocycloalkyl, heteroaryl or haloalkyl; and $R^{22}$ is H.

In another embodiment, $R^1$ is —$CH_2$—; $R^2$ is —C(O)$OR^9$ or —C(O)N($R^9$)$_2$; each occurrence of $R^9$ is independently H or alkyl; $R^{10}$ is phenyl, naphthyl, pyridyl, quinolinyl or quinoxalinyl; $R^{21}$ is haloalkyl; and $R^{22}$ is H.

In another embodiment, is —$CH_2$—; $R^2$ is —C(O)$OR^9$ or —C(O)N($R^9$)$_2$; each occurrence of $R^9$ is independently H or alkyl; $R^{10}$ is phenyl, naphthyl, pyridyl, quinolinyl or quinoxalinyl; and $R^{21}$ and $R^{22}$ and the nitrogen atoms to which they are attached, join to form a group having the formula:

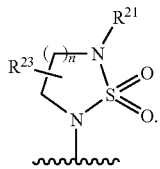

In one embodiment, $R^1$ is —$CH_2$—; $R^2$ is —$C(O)OR^9$ or —$C(O)N(R^9)_2$; each occurrence of $R^9$ is independently H or alkyl; $R^{10}$ is:

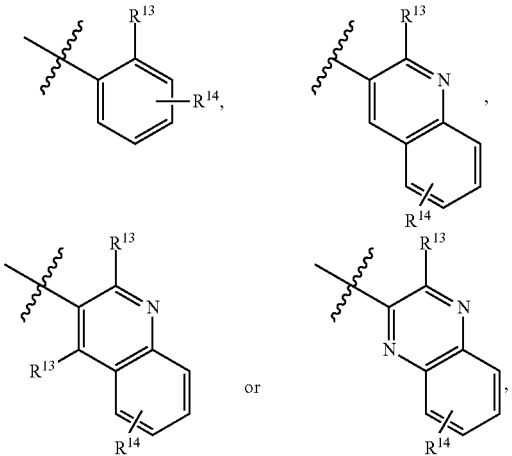

wherein $R^{13}$ is H, F, Br or Cl, and $R^{14}$ represents up to 4 optional and additional substituents, each independently selected from alkyl, cycloalkyl, $CF_3$, —CN, halo, —O-alkyl, —$NHSO_2$-alkyl, —$NO_2$, —$C(O)NH_2$, —$C(O)NH$-alkyl, —$C(O)OH$, hydroxy, —$NH_2$, —$SO_2$alkyl, —$SO_2NH$alkyl, —S-alkyl, —$CH_2NH_2$, —$CH_2OH$, —$SO_2NH_2$, —NHC(O)-alkyl, —C(O)O-alkyl, —C(O)-heterocycloalkyl and heteroaryl; $R^{21}$ is H, alkyl, aryl, cycloalkyl, heterocycloalkyl, heteroaryl or haloalkyl; and $R^{22}$ is H.

In another embodiment, $R^1$ is —$CH_2$—; $R^2$ is —$C(O)OR^9$ or —$C(O)N(R^9)_2$; each occurrence of $R^9$ is independently H or alkyl: $R^{10}$ is:

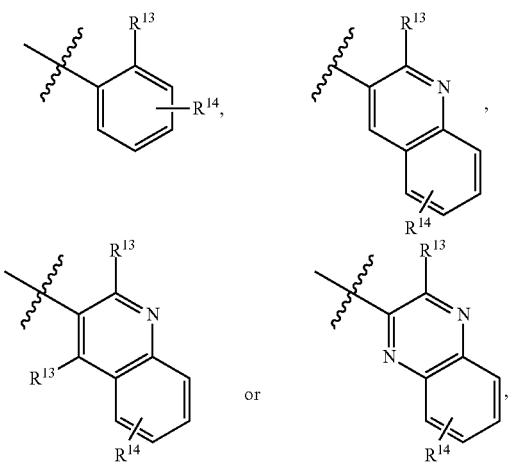

wherein $R^{13}$ is H, F, Br or Cl, and $R^{14}$ represents up to 4 optional and additional substituents, each independently selected from alkyl, cycloalkyl, $CF_3$, —CN, halo, —O-alkyl, —$NHSO_2$-alkyl, —$NO_2$, —$C(O)NH_2$, —$C(O)NH$-alkyl, —$C(O)OH$, hydroxy, —$NH_2$, —$SO_2$alkyl, —$SO_2NH$alkyl, —S-alkyl, —$CH_2NH_2$, —$CH_2OH$, —$SO_2NH_2$, —NHC(O)-alkyl, —C(O)O-alkyl, —C(O)-heterocycloalkyl and heteroaryl; $R^{21}$ is haloalkyl; and $R^{22}$ is H.

In another embodiment, $R^1$ is —$CH_2$—; $R^2$ is —$C(O)OR^9$ or —$C(O)N(R^9)_7$; each occurrence of $R^9$ is independently H or alkyl; $R^{10}$ is:

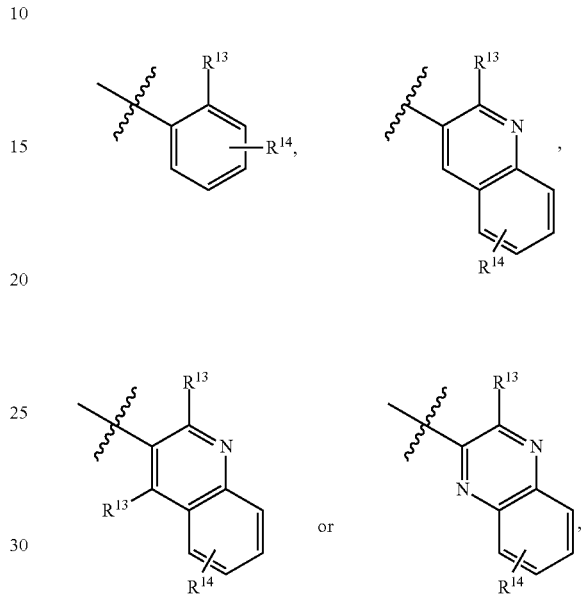

wherein $R^{13}$ is H, F, Sr or Cl, and $R^{14}$ represents up to 4 optional and additional substituents, each independently selected from alkyl, cycloalkyl, $CF_3$, —CN, halo, —O-alkyl, —$NHSO_2$-alkyl, —$NO_2$, —$C(O)NH_2$, —$C(O)NH$-alkyl, —$C(O)OH$, hydroxy, —$NH_2$, —$SO_2$alkyl, —$SO_2NH$alkyl, —S-alkyl, —$CH_2NH_2$, —$CH_2OH$, —$SO_2NH_2$, —NHC(O)-alkyl, —C(O)O-alkyl, —C(O)-heterocycloalkyl and heteroaryl; and $R^{21}$ and $R^{22}$ and the nitrogen atoms to which they are attached, join to form a group having the formula:

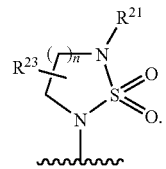

In one embodiment, $R^1$ is —$CH_2$, and $R^{10}$ is

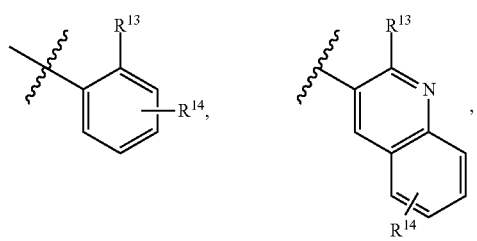

-continued

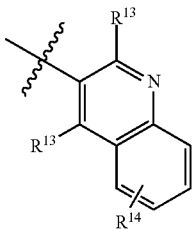 or 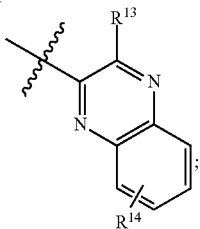 ;

$R^2$ is —C(O)OR$^9$ or —C(O)N(R$^9$)$_2$; $R^{21}$ is H, alkyl, aryl, cycloalkyl, heterocycloalkyl, heteroaryl or haloalkyl; and $R^{22}$ is H.

In another embodiment, $R^1$ is —CH$_2$— and $R^{10}$ is

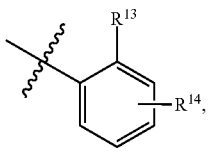 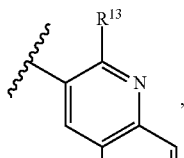 ,

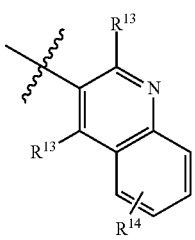 or 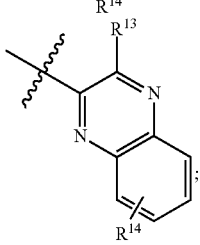 ;

$R^2$ is —C(O)OR$^9$ or —C(O)N(R$^9$)$_2$; $R^{21}$ is haloalkyl; and $R^{22}$ is H.

In another embodiment, $R^1$ is —CH$_2$— and $R^{10}$ is

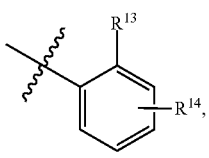 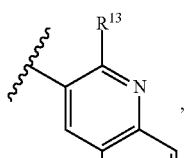 ,

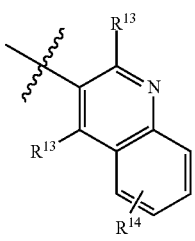 or 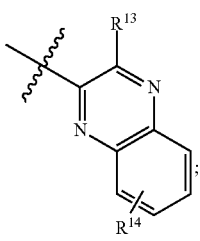 ;

$R^2$ is —C(O)OR$^9$ or —C(O)N(R$^9$)$_2$; and $R^{21}$ and $R^{22}$ and the nitrogen atoms to which they are attached, join to form a group having the formula:

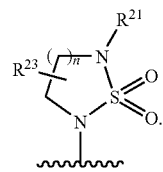

In one embodiment, $R^1$ is —CH$_2$— and $R^{10}$ is

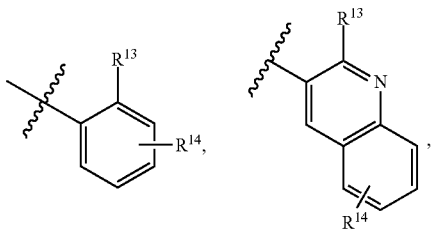,

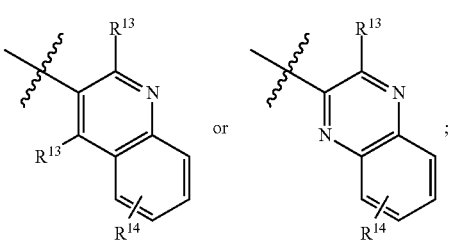 or 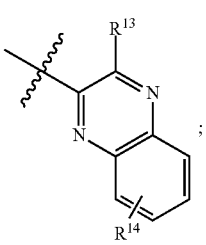 ;

$R^2$ is —C(O)OR$^9$ or —C(O)N(R$^9$)$_2$; each occurrence of $R^9$ is independently H or alkyl; $R^{21}$ is H, alkyl, aryl, cycloalkyl, heterocycloalkyl, heteroaryl or haloalkyl; and $R^{22}$ is H.

In another embodiment, $R^1$ is —CH$_2$— and $R^{10}$ is

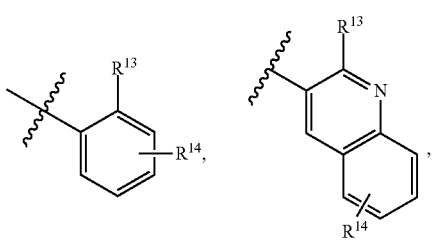,

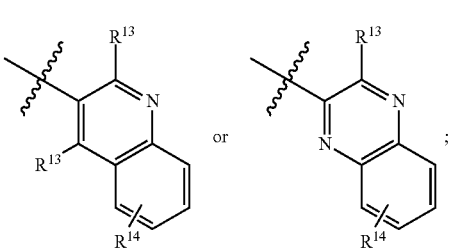 or 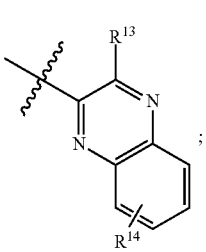 ;

$R^2$ —C(O)OR$^9$ or —C(O)N(R$^9$)$_2$; each occurrence of $R^9$ is independently H or alkyl; $R^{21}$ is haloalkyl; and $R^{22}$ is H.

In another embodiment, $R^1$ is —CH$_2$— and $R^{10}$ is

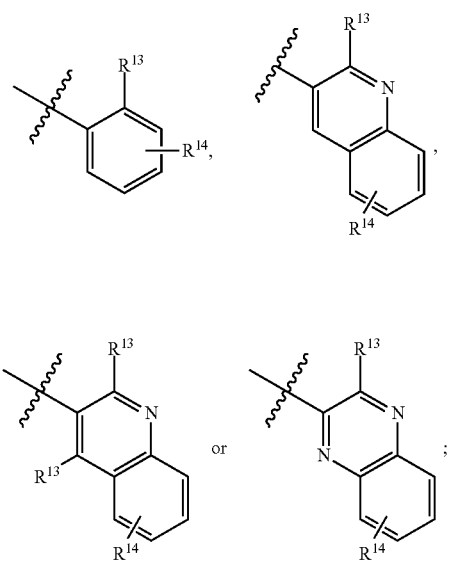

$R^2$ is —C(O)OR$^9$ or —C(O)N(R$^9$)$_2$; each occurrence of R$^9$ is independently H or alkyl; and $R^{21}$ and $R^{22}$ and the nitrogen atoms to which they are attached, join to form a group having the formula:

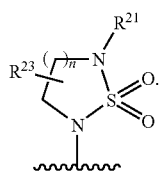

In one embodiment, $R^1$ is —CH$_2$— and $R^{10}$ is

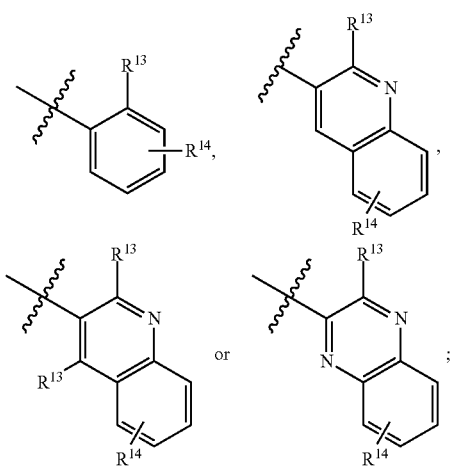

$R^2$ is —C(O)OH; $R^{21}$ is H, alkyl, aryl, cycloalkyl, heterocycloalkyl, heteroaryl or haloalkyl; and $R^{22}$ is H.

In another embodiment, $R^1$ is —CH$_2$— and $R^{10}$ is

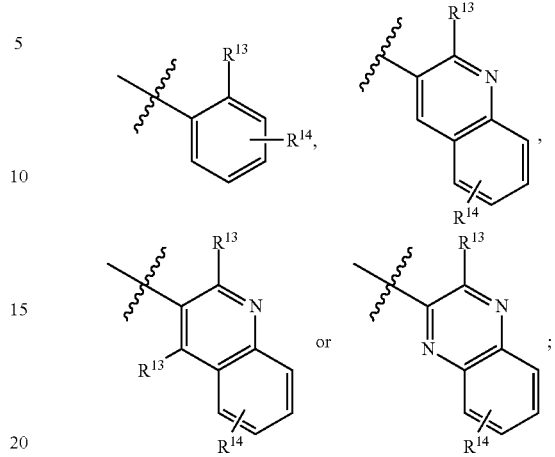

$R^2$ is —C(O)OH; $R^{21}$ is haloalkyl; and $R^{22}$ is H.

In another embodiment, $R^1$ is —CH$_2$— and $R^{10}$ is

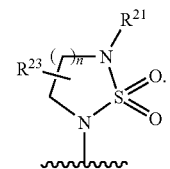

$R^2$ is —C(O)OH; and $R^{21}$ and $R^{22}$ and the nitrogen atoms to which they are attached, join to form a group having the formula:

In one embodiment, $R^1$-$R^{10}$ is benzyl, wherein the phenyl moiety of the benzyl group is optionally substituted with from 1-4 groups independently selected from: halo, —NH$_2$, —NHSO$_2$-alkyl, haloalkyl, methoxy, —O-haloalkyl, —[C(R$^{12}$)$_2$]$_q$—NHC(O)NH-alkyl, alkyl, hydroxy, —CN, —C(O)NH$_2$ or —[C(R$^{12}$)$_2$]$_q$—NH$_2$; $R^2$ is —C(O)OR$^9$ or —C(O)N(R$^9$)$_2$; $R^{21}$ is H, alkyl, aryl, cycloalkyl, heterocycloalkyl, heteroaryl or haloalkyl; and $R^{22}$ is H.

In another embodiment, $R^1$-$R^{10}$ is benzyl, wherein the phenyl moiety of the benzyl group is optionally substituted with from 1-4 groups independently selected from: halo, —NH$_2$, —NHSO$_2$-alkyl, haloalkyl, methoxy, —O-haloalkyl, —[C(R$^{12}$)$_2$]$_q$—NHC(O)NH-alkyl, alkyl, hydroxy, —CN, —C(O)NH$_2$ or —[C(R$^{12}$)$_2$]$_q$—NH$_2$; R$^2$ is —C(O)OR$^9$ or —C(O)N(R$^9$)$_2$; R$^{21}$ is haloalkyl; and R$^{22}$ is H.

In another embodiment, R$^1$-R$^{10}$ is benzyl, wherein the phenyl moiety of the benzyl group is optionally substituted with from 1-4 groups independently selected from: halo, —NH$_2$, —NHSO$_2$-alkyl, haloalkyl, methoxy, —O-haloalkyl, —[C(R$^{12}$)$_2$]$_q$—NHC(O)NH-alkyl, alkyl, hydroxy, —CN, —C(O)NH$_2$ or —[C(R$^{12}$)$_2$]$_q$—NH$_2$; R$^2$ is —C(O)OR$^9$ or —C(O)N(R$^9$)$_2$; and R$^{21}$ and R$^{22}$ and the nitrogen atoms to which they are attached, join to form a group having the formula:

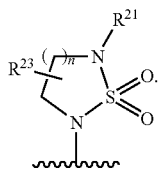

In one embodiment, R$^1$ is —CH$_2$— and R$^{10}$ is

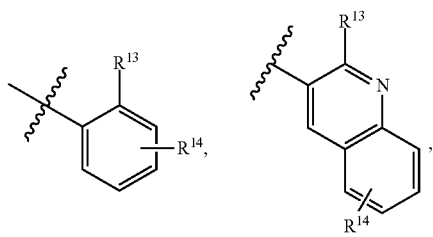

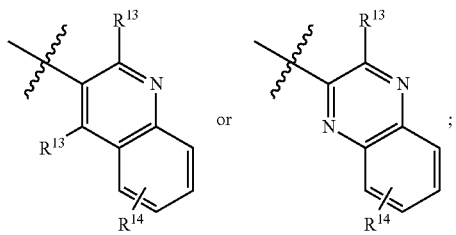

R$^2$ is —C(O)OR$^9$ or —C(O)N(R)$_2$; R$^4$, R$^5$, R$^6$ and R$^7$ are each independently selected from H, alkyl, —O-alkyl or halo; R$^{21}$ is H, alkyl, aryl, cycloalkyl, heterocycloalkyl, heteroaryl or haloalkyl; and R$^{22}$ is H.

In another embodiment, R$^1$ is —CH$_2$— and R$^{10}$ is

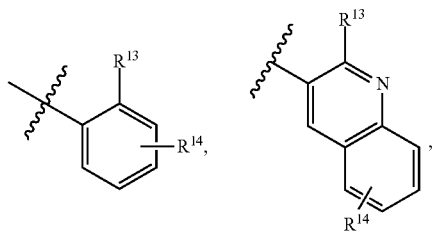

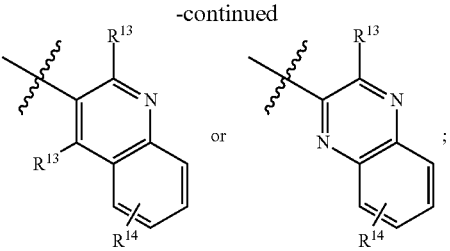

R$^2$ is —C(O)OR$^9$ or —C(O)N(R$^9$)$_2$; R$^4$, R$^5$, R$^6$ and R$^7$ are each independently selected from H, alkyl, —O-alkyl or halo; R$^{21}$ is haloalkyl; and R$^{22}$ is H.

In another embodiment, R$^1$ is —CH$_2$— and R$^{10}$ is

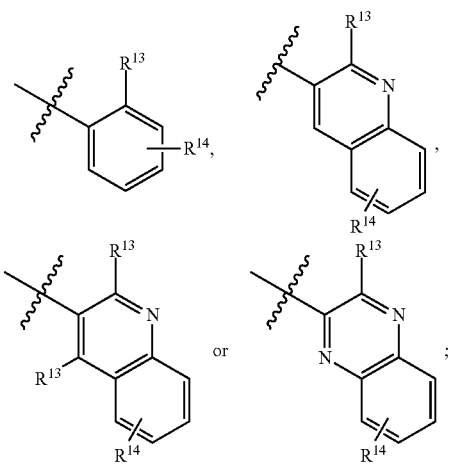

R$^2$ is —C(O)OR$^9$ or —C(O)N(R$^9$)$_2$; R$^4$, R$^5$, R$^6$ and R$^7$ are each independently selected from H, alkyl, —O-alkyl or halo; and R$^{21}$ and R$^{22}$ and the nitrogen atoms to which they are attached, join to folio a group having the formula:

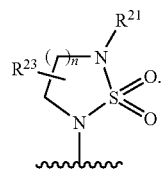

In one embodiment, R$^1$-R$^{10}$ is benzyl, wherein the phenyl moiety of the benzyl group is optionally substituted with from 1-4 groups independently selected from: halo, —NH$_2$, —NHSO$_2$-alkyl, haloalkyl, methoxy, —O-haloalkyl, —[C(R$^{12}$)$_2$]$_q$—NHC(O)NH-alkyl, alkyl, hydroxy, —CN, —C(O)NH$_2$ or —[C(R$^{12}$)$_2$]$_q$—NH$_2$; R$^2$ is —C(O)OR$^9$ or —C(O)N(R$^9$)$_2$; R$^4$, R$^5$, R$^6$ and R$^7$ are each independently selected from H, alkyl, —O-alkyl or halo; R$^{21}$ is H, alkyl, aryl, cycloalkyl, heterocycloalkyl, heteroaryl or haloalkyl; and R$^{22}$ is H.

In another embodiment, R$^1$-R$^{10}$ is benzyl, wherein the phenyl moiety of the benzyl group is optionally substituted with from 1-4 groups independently selected from: halo, —NH$_2$, —NHSO$_2$-alkyl, haloalkyl, methoxy, —O-haloalkyl, —[C(R$^{12}$)$_2$]$_q$—NHC(O)NH-alkyl, alkyl, hydroxy, —CN, —C(O)NH$_2$ or —[C(R$^{12}$)$_2$]$_q$—NH$_2$; R$^2$ is —C(O)OR$^9$ or —C(O)N(R$^9$)$_2$; R$^4$, R$^5$, R$^6$ and R$^7$ are each independently selected from H, alkyl, —O-alkyl or halo; R$^{21}$ is haloalkyl; and R$^{22}$ is H.

In another embodiment, $R^1$-$R^{10}$ is benzyl, wherein the phenyl moiety of the benzyl group is optionally substituted with from 1-4 groups independently selected from: halo, —NH$_2$, —NHSO$_2$-alkyl, haloalkyl, methoxy, —O-haloalkyl, —[C(R$^{12}$)$_2$]$_q$—NHC(O)NH-alkyl, alkyl, hydroxy, —CN, —C(O)NH$_2$ or —[C(R$^{12}$)$_2$]$_q$—NH$_2$; $R^2$ is —C(O)OR$^9$ or —C(O)N(R$^9$)$_2$; $R^4$, $R^5$, $R^6$ and $R^7$ are each independently selected from H, alkyl, —O-alkyl or halo; and $R^{21}$ and $R^{22}$ and the nitrogen atoms to which they are attached, join to faun a group having the formula:

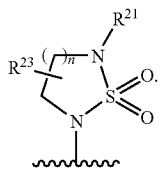

In one embodiment, $R^1$ is —CH$_2$— and $R^{10}$ is

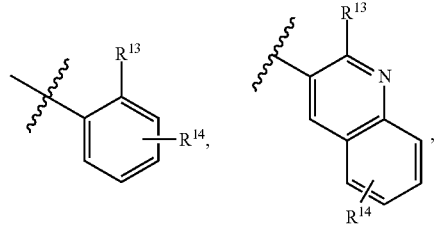

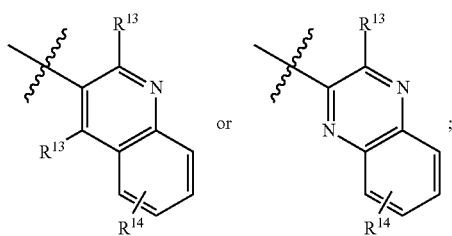

$R^2$ is —C(O)OR$^9$ or —C(O)N(R$^9$)$_2$; $R^4$, $R^6$ and $R^7$ are each H; $R^5$ is H, alkyl, —O-alkyl or halo; $R^{21}$ is H, alkyl, aryl, cycloalkyl, heterocycloalkyl, heteroaryl or haloalkyl; and $R^{22}$ is H.

In another embodiment, $R^1$ is —CH$_2$— and $R^{10}$ is

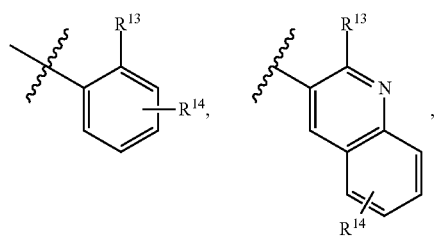

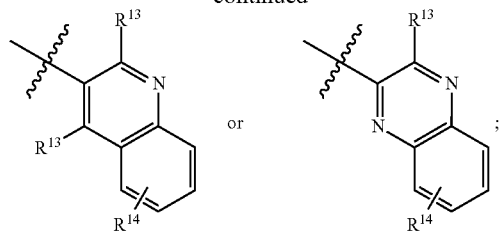

$R^4$, $R^6$ and $R^7$ are each H; $R^5$ is H, alkyl, —O-alkyl or halo; $R^{21}$ is haloalkyl; and $R^{22}$ is H.

In another embodiment, $R^1$ is —CH$_2$— and $R^{10}$ is

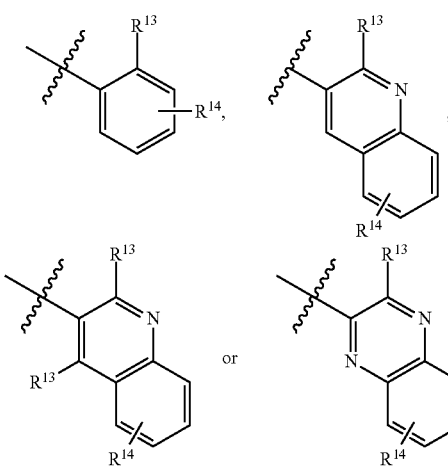

$R^2$ is —C(O)OR$^9$ or —C(O)N(R$^9$)$_2$; $R^4$, $R^6$ and $R^7$ are each H; $R^5$ is H, alkyl, —O-alkyl or halo; and $R^{21}$ and $R^{22}$ and the nitrogen atoms to which they are attached, join to form a group having the formula:

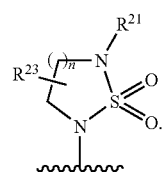

In one embodiment, $R^1$-$R^{10}$ is benzyl, wherein the phenyl moiety of the benzyl group is optionally substituted with from 1-4 goups independently selected from: halo, —NH$_2$, —NHSO$_2$-alkyl, haloalkyl, methoxy, —O-haloalkyl, —[C(R$^{12}$)$_2$]$_q$—NHC(O)NH-alkyl, alkyl, hydroxy, —CN, —C(O)NH$_2$ or —[C(R$^{12}$)$_2$]$_q$—NH$_2$; $R^2$ is —C(O)OR$^9$ or —C(O)N(R$^9$)$_2$; $R^4$, $R^6$ and $R^7$ are each H; $R^5$ is H, alkyl, —O-alkyl or halo; $R^{21}$ is H, alkyl, aryl, cycloalkyl, heterocycloalkyl, heteroaryl or haloalkyl; and $R^{22}$ is H.

In another embodiment, $R^1$-$R^{10}$ is benzyl, wherein the phenyl moiety of the benzyl group is optionally substituted with from 1-4 groups independently selected from: halo, —NH$_2$, —NHSO$_2$-alkyl, haloalkyl, methoxy, —O-haloalkyl, —[C(R$^{12}$)$_2$]$_q$—NHC(O)NH-alkyl, alkyl, hydroxy, —CN, —C(O)NH$_2$ or —[C(R$^{12}$)$_2$]$_q$—NH$_2$; $R^2$ is —C(O)OR$^9$ or —C(O)N(R$^9$)$_2$; $R^4$, $R^6$ and $R^7$ are each H; $R^5$ is H, alkyl, —O-alkyl or halo; $R^{21}$ is haloalkyl; and $R^{22}$ is H.

In another embodiment, $R^1$-$R^{10}$ is benzyl, wherein the phenyl moiety of the benzyl group is optionally substituted with from 1-4 groups independently selected from: halo, —NH$_2$, —NHSO$_2$-alkyl, haloalkyl, methoxy, —O-haloalkyl, —[C(R$^{12}$)$_2$]$_q$—NHC(O)NH-alkyl, alkyl, hydroxy, —CN, —C(O)NH$_2$ or —[C(R$^{12}$)$_2$]$_q$—NH$_2$; R$^2$ is —C(O)OR$^9$ or —C(O)N(R$^9$)$_2$; R$^4$, R$^6$ and R$^7$ are each H; R$^5$ is H, alkyl, —O-alkyl or halo; and R$^{21}$ and R$^{22}$ and the nitrogen atoms to which they are attached, join to form a group having the formula:

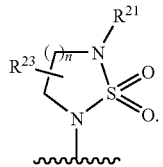

In one embodiment, R$^{21}$ and R$^{22}$ and the nitrogen atoms to which each are attached, join to form a group having the formula:

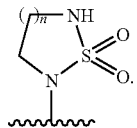

In another embodiment, R$^{21}$ and R$^{22}$ and the nitrogen atoms to which each are attached, join to fowl a group having the formula:

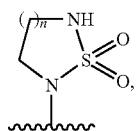

wherein n is 1.

In another embodiment, R$^{21}$ and R$^{22}$ and the nitrogen atoms to which each are attached, join to form a group having the formula:

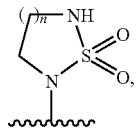

wherein n is 2.

In one embodiment, for the compounds of formula (II), R$^1$, R$^2$, R$^4$, R$^5$, R$^6$, R$^7$, R$^{10}$, R$^{21}$ and R$^{22}$ are selected independently of each other.

In another embodiment, a compound of formula (II) is in purified form.

Non-limiting illustrative examples of the 3-Aminosulfonyl Substituted Indole. Derivatives of formulas (I) and (II) are set forth in the table below.

| Compound number | Structure | MS (M + H) |
|---|---|---|
| 1 | 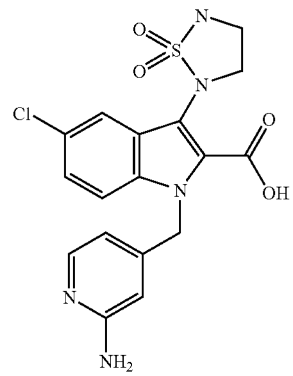 [SMILES: Nc1cc(Cn2c(C(=O)O)c(N3CCNS3(=O)=O)c3cc(Cl)ccc32)ccn1] | 421 |
| 2 | 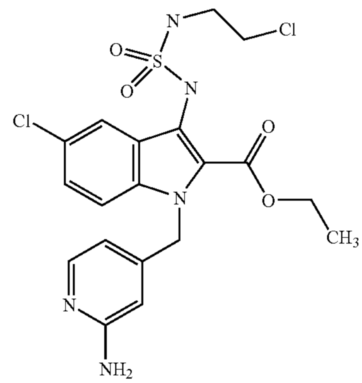 [SMILES: CCOC(=O)c1c(NS(=O)(=O)NCCCl)c2cc(Cl)ccc2n1Cc1ccnc(N)c1] | 486 |
| 3 | 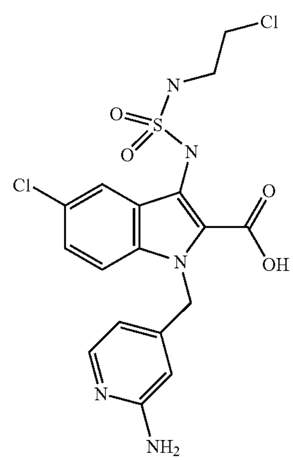 [SMILES: Nc1cc(Cn2c(C(=O)O)c(NS(=O)(=O)NCCCl)c3cc(Cl)ccc32)ccn1] | 458.3 |
| 4 | 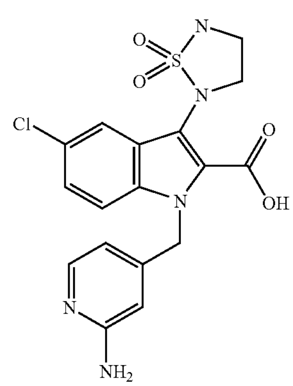 [SMILES: Nc1cc(Cn2c(C(=O)O)c(N3CCNS3(=O)=O)c3cc(Cl)ccc32)ccn1] | 421.2 |

-continued

| Compound number | Structure | MS (M + H) |
|---|---|---|
| 5 | 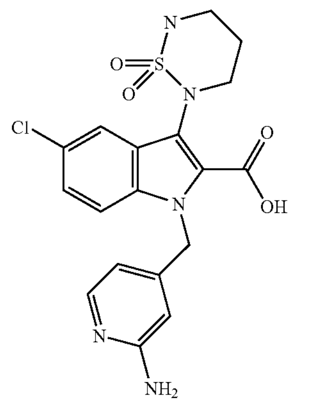 [SMILES: Nc1cc(Cn2c(C(=O)O)c(N3CCCNS3(=O)=O)c3cc(Cl)ccc32)ccn1] | 436.2 |
| 6 | | 513.1 | and pharmaceutically acceptable salts, solvates, esters and prodrugs thereof.

Methods For Making the 3-Aminosulfonyl Substituted Indole Derivatives

Methods useful for making the 3-Aminosulfonyl Substituted Indole Derivatives are set forth in the Examples below and generalized in Schemes 1-7. Practical methodologies for the synthesis of indoles has been reviewed by G. R. Humphrey and J. T. Kuethe in Chemical Reviews 106, 2875-2911, 2006.

Scheme 1 shows a method for preparing compounds of formula iv, which are useful intermediates for making of the 3-Aminosulfonyl Substituted Indole Derivatives.

Scheme 1

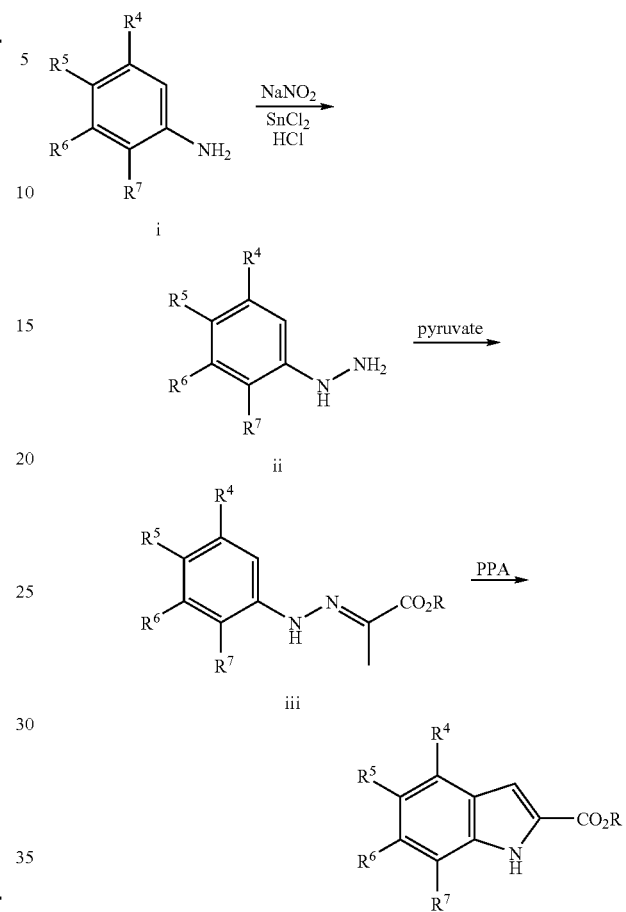

wherein $R^4$-$R^7$ are defined above for the compounds of formulas (I) and (II) and R is ethyl.

An aniline compound of formula i can be converted to an indole compound of formula iv using various indole syntheses that are well-known to those skilled in the art of organic synthesis, including but not limited to, a Fischer indole synthesis through intermediates of type ii and iii, the method set forth in Nazare et al., *Angew. Chem*, 116:4626-4629 (2004), Scheme 2 shows an alternative method useful for making the intermediate compounds of formula iv.

Scheme 2

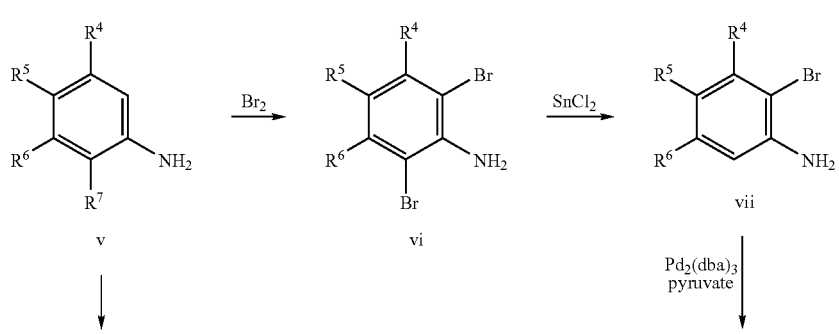

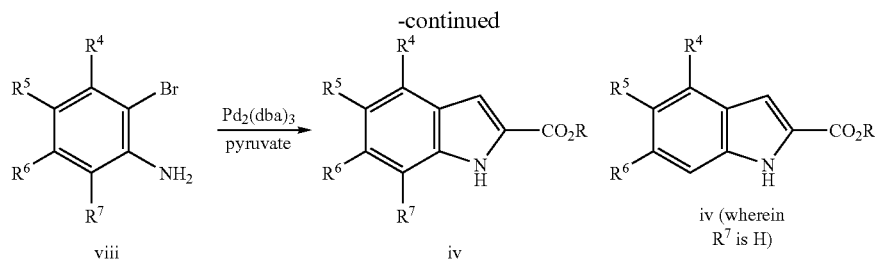

wherein $R^4$-$R^7$ are defined above for the compounds of formulas (I) and (II) and R is ethyl.

A benzene derivative of formula v, wherein $R^7$ is H, can be di-brominated to give compound vi. Selective de-bromination provides the corresponding monobromo analog vii, which under palladium catalyzed cyclization conditions provides the desired intermediate iv, wherein $R^7$ is H. Alternatively a compound of formula v, wherein $R^7$ is other than H, can be monobrominated to give compound viii. Compound viii can then undergo under palladium catalyzed cyclization conditions provides the desired intermediate iv, wherein R' is other than H.

Scheme 3 shows a method useful for making the compounds of formula x, which are useful intermediates for making the 3-Aminosulfonyl Substituted Indole Derivatives of formula (I), wherein $R^2$ is —C(O)N($R^9$)SO$_2$$R^{11}$.

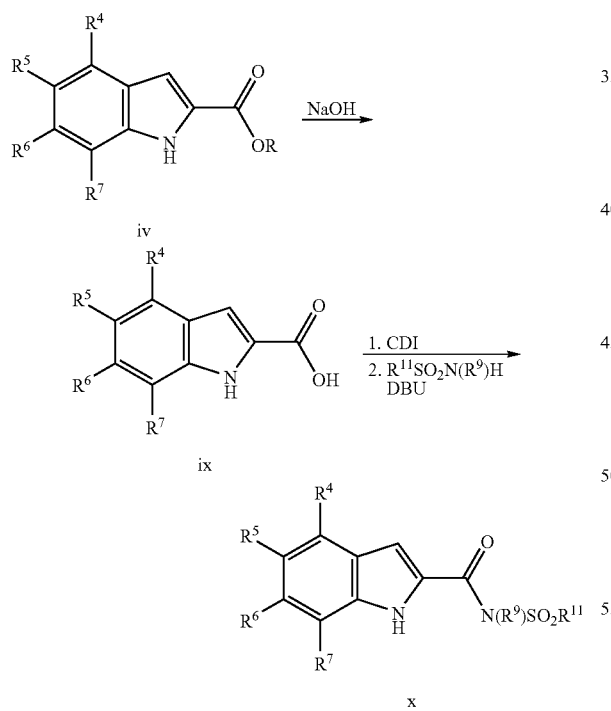

wherein $R^1$, $R^4$-$R^7$, $R^9$ and $R^{11}$ are defined above for the 3-Aminosulfonyl Substituted Indole Derivatives of formula (I).

2-carboxy indole compounds of formula iv can be converted to their corresponding 2-COOH analogs of formula ix upon saponification with a hydroxide base, such as sodium hydroxide. The compounds of formula ix can then be coupled with a compound of formula $R^{11}$SO$_2$NH($R^9$) in the presence of carbonyldiimidazole (CDI) and 1,8-diazabicyclo[5.4.0]undec-7-ene (DBU) to provide the acyl sulfonamido compounds of formula x.

Scheme 4 shows a method useful for making the compounds of formula xii, which are useful intermediates for making the 3-Aminosulfonyl Substituted Indole Derivatives of formula (I), wherein $R^2$ is:

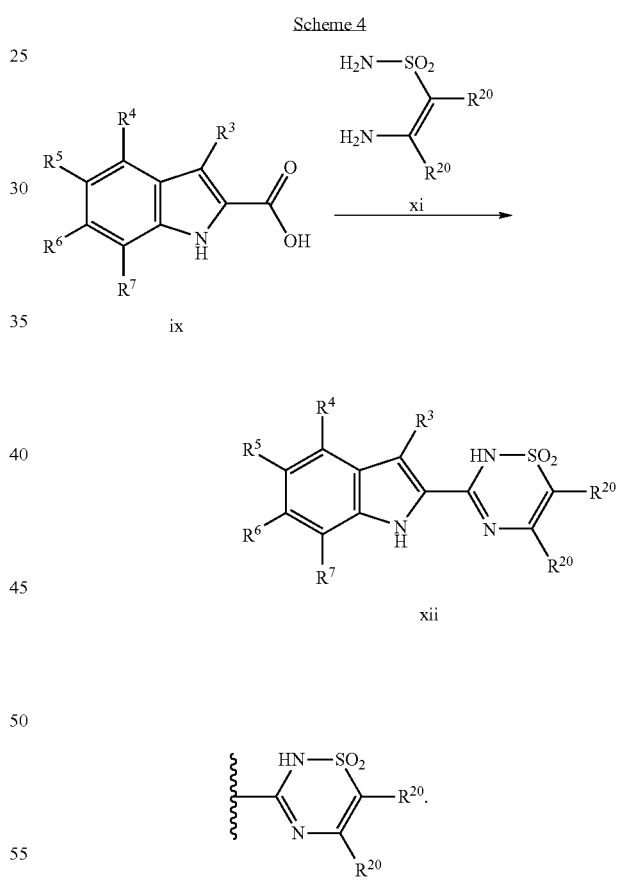

wherein $R^1$, $R^4$-$R^7$ and $R^{20}$ are defined above for the 3-Aminosulfonyl Substituted Indole Derivatives of formula (I).

2-carboxylic acid indole compounds of formula ix can be reacted with a 2-amino sulfonamide of formula xi to provide the compounds of formula xii.

Scheme 5 shows a method useful for making the compounds of formula xii, which are useful intermediates for making the 3-Aminosulfonyl Substituted Indole Derivatives of formula (II), wherein $R^2$ is —C(O)N($R^9$)$_2$.

Scheme 5

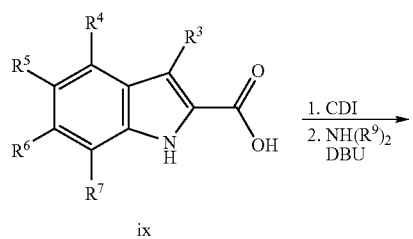

ix

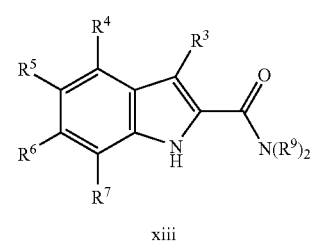

xiii wherein $R^1$, $R^3$, $R^4$-$R^7$, $R^9$ and $R^{10}$ are defined above for the compounds of formula (I).

A 2-carboxy indole compound of formula G can be coupled with an amine of formula $NH(R^9)_2$ in the presence of carbonyldiimidazole (CDI) and 1,8-diazabicyclo[5.4.0]undec-7-ene (DBU) to provide the compounds of formula J, which correspond to the 3-Aminosulfonyl Substituted Indole Derivatives of formula (II), wherein $R^2$ is —$C(O)N(R^9)_2$.

Scheme 6 shows a method useful for making the 3-Aminosulfonyl Substituted Indole Derivatives.

wherein $R^1$, $R^2$, $R^4$-$R^7$, $R^{10}$, $R^{21}$ and $R^{22}$ are defined above for the compounds of formulas (I) and (II) and LG is a leaving group, such as Cl, Br, I, —O-mesyl, —O-tosyl or —O-triflyl.

An indole compound of formula xiv, with group $R^2$ intact and optionally protected, can be nitrated using nitric acid to provide the 3-nitro indole compounds of formula xv. The compounds of formula xv can then be reacted with a compound of formula $R^{22}$-LG in the presence of a non-nucleophilic base, such as cesium carbonate, to install the —$R^1$-$R^{10}$ group and provide the compounds of formula xvi. The nitro group of the compounds of formula xvi can be reduced using iron to provide the 3-amino indole compounds of formula xvii. The compounds of formula xvii can be optionally derivatized to install group $R^{22}$ at this stage by reacting the compounds of formula xvii with a compound of formula $R^{22}$-LG in the presence of a non-nucleophilic base to provide the compounds of formula xviii, wherein $R^{22}$ is other than H. A compound of formula xvii or xviii can then be reacted with a compound of formula xix to provide the compounds of formula xx, which correspond to the 3-Aminosulfonyl Substituted Indole Derivatives wherein $R^{21}$ and $R^{22}$ do not join to form a heterocyclic ring.

Scheme 7 shows a method useful for making the 3-Aminosulfonyl Substituted Indole Derivatives, $R^{21}$ and $R^{22}$ and the nitrogen atoms to which they are attached, join to form a group having the formula:

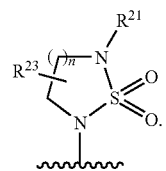

Scheme 6

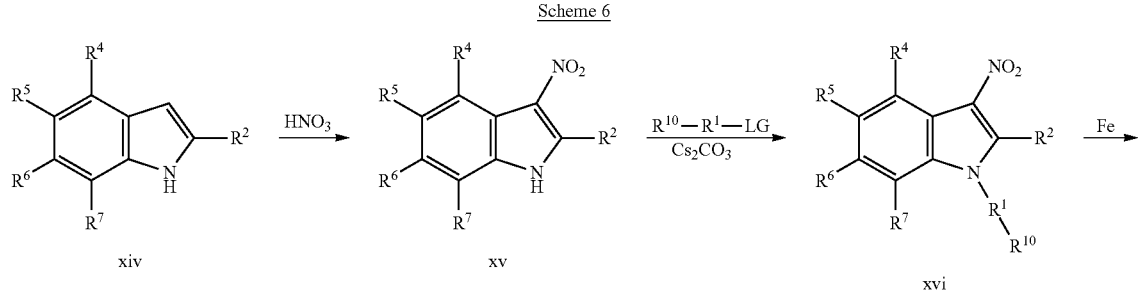

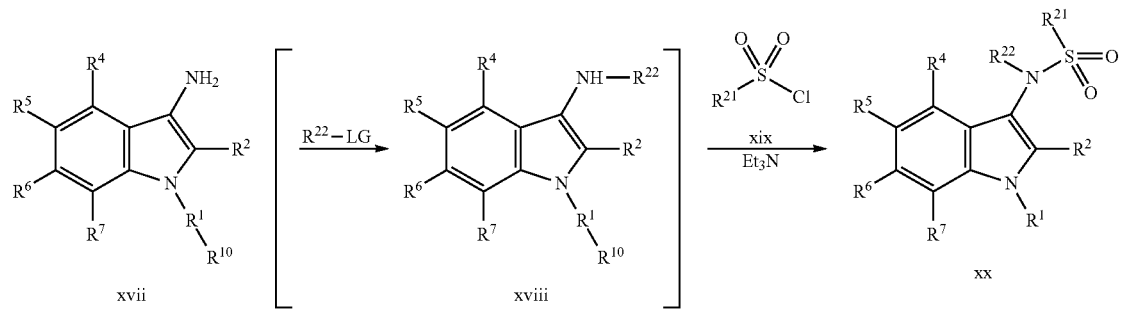

Scheme 7

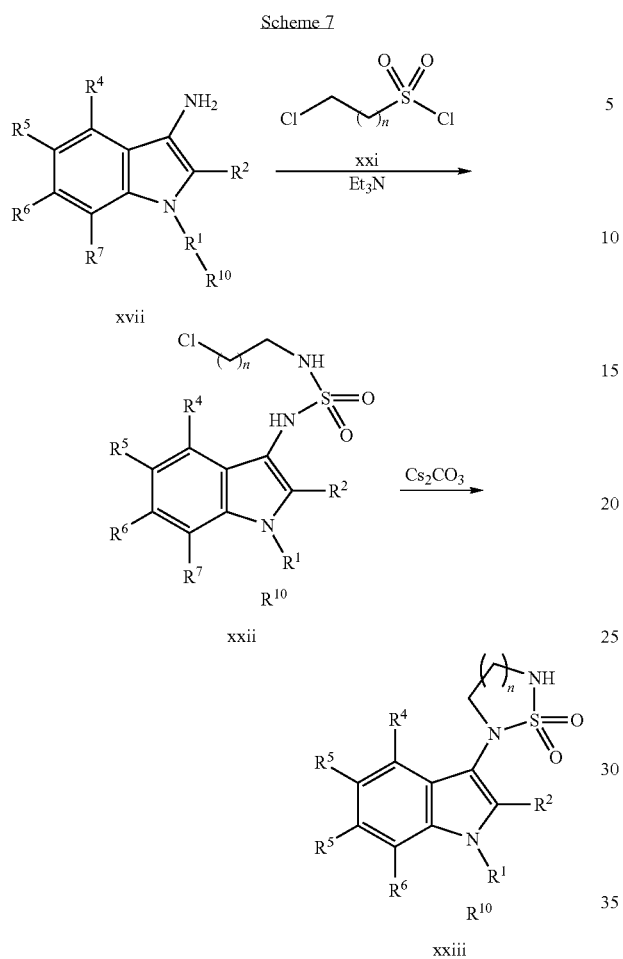

wherein $R^1$, $R^2$, $R^4$-$R^7$ and $R^{10}$ are defined above for the compounds of formulas (I) and (II) and n is 1-3.

The compounds of formula xvii can be reacting with a compound of formula xxi in the presence of a non-nucleophilic base, such as triethylamine, to provide the compounds of formula xxii. The compounds of formula xxii can then be cyclized upon treatment with a base such as cesium carbonate, to provide the compounds of formula xxiii, which correspond to the 3-Aminosulfonyl Substituted Indole Derivatives wherein $R^{21}$ and $R^{22}$, and the nitrogen atoms to which they are attached, join to form a heterocyclic ring.

The starting material and reagents depicted in Schemes 1-7 are either available from commercial suppliers such as Sigma-Aldrich (St. Louis, Mo.) and Acros Organics Co. (Fair Lawn, N.J.), or can be prepared using methods well-known to those of skill in the art of organic synthesis.

One skilled in the art will recognize that the synthesis of 3-Aminosulfonyl Substituted Indole Derivatives may require the need for the protection of certain functional groups (i.e., derivatization for the purpose of chemical compatibility with a particular reaction condition). Suitable protecting groups for the various functional groups of the 3-Aminosulfonyl Substituted Indole Derivatives and methods for their installation and removal may be found in Greene et al., *Protective Groups in Organic Synthesis*, Wiley-Interscience, New York, (1999).

One skilled in the art will recognize that one route will be optimal depending on the choice of appendage substituents. Additionally, one skilled in the art will recognize that in some cases the order of steps has to be controlled to avoid functional group incompatibilities. One skilled in the art will recognize that a more convergent route (i.e. non-linear or preassembly of certain portions of the molecule) is a more efficient method of assembly of the target compounds. Methods suitable for the preparation of 3-Aminosulfonyl Substituted Indole Derivatives are set forth above in Schemes 1-7.

The starting materials and the intermediates prepared using the methods set forth in Schemes 1-7 may be isolated and purified if desired using conventional techniques, including but not limited to filtration, distillation, crystallization, chromatography and the like. Such materials can be characterized using conventional means, including physical constants and spectral data.

EXAMPLES

General Methods

Solvents, reagents, and intermediates that are commercially available were used as received. Reagents and intermediates that are not commercially available were prepared in the manner as described below. $^1$H NMR spectra were obtained on a Broker Avarice 500 (500 MHz) and are reported as ppm down field from $Me_4Si$ with number of protons, multiplicities, and coupling constants in Hertz indicated parenthetically. Where LC/MS data are presented, analyses was performed using an Applied Biosystems API-100 mass spectrometer and Shimadzu SCL-10A LC column: Altech platinum C18, 3 micron, 33 mm×7 mm ID; gradient flow: 0 minute—10% $CH_3CN$, 5 minutes—95% $CH_3CN$, 5-7 minutes—95% $CH_3CN$, 7 minutes—stop. The retention time and observed parent ion are given. Flash column chromatography was performed using pre-packed normal phase silica from Biotage, Inc. or bulk silica from Fisher Scientific.

Example 1

Preparation of Compound 6

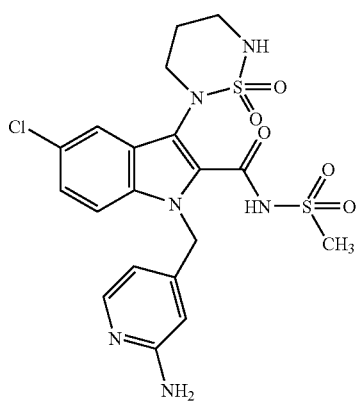

Step 1: Synthesis of Compound A2:

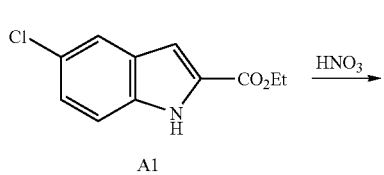

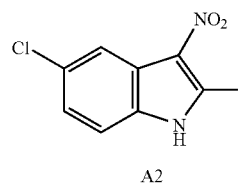

A2

To acetic anhydride (200 mL, cooled to 0° C. in an ice bath) was added fuming nitric acid (30 mL) dropwise. To the resulting cooled solution was added compound A1 (5.00 g, 22.4 mmol) and the resulting mixture was allowed to stir at 0° C. for 2.5 hours. The reaction mixture was then poured into a mixture of ice (860 g) and sodium bicarbonate (50 g) and the resulting suspension was extracted with ethyl acetate (3×1 L). The separated organic layers were combined, washed with brine, dried over magnesium sulfate, filtered and concentrated in vacuo. The residue obtained was purified using flash column chromatography on silica gel (5-100% EtOAc/Hexanes) to provide compound A2 (L50 g, 25% yield).

Step 2: Synthe of Comnound A4:

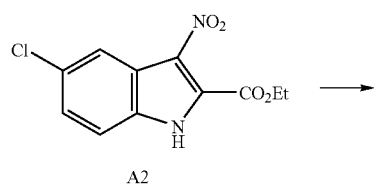

A2

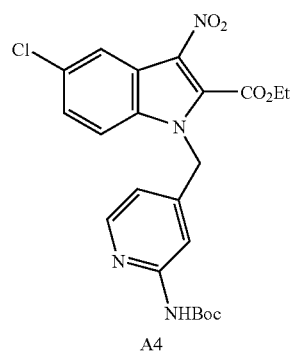

A4

To a solution of compound A4 (1.0 g, 3.7 mmol) in DMF (50 mL) was added (4-bromomethyl-pyridin-2-yl)-carbamic acid tert-butyl ester (1.3 g, 4.5 mmol), followed by cesium carbonate (3.0 g, 9.3 mmol). The resulting reaction was allowed to stir at room temperature for 5 hours, then ethyl acetate (100 mL) and water (100 mL) were added to the reaction mixture, and the layers were separated. The aqueous layer was further extracted with ethyl acetate (100 mL) and the combined organic layers were washed sequentially with water (2=200 mL) and brine (200 mL), dried over magnesium sulfate, filtered and concentrated in vacuo. The residue obtained was purified using flash column chromatography on silica gel (5-50% EtOAc/Hexanes) to provide compound A4 (0.68 g, 38% yield). M.S. found for $C_{12}H_{23}ClN_4O_6$: 475.3 $(M+H)^+$; 375.2 $(M-Boc+H)^+$.

Step 3: Synthesis of Compound A5:

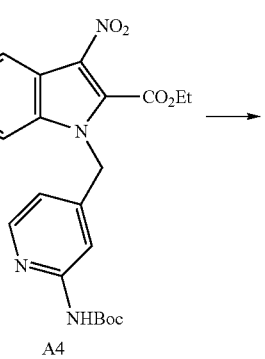

A4

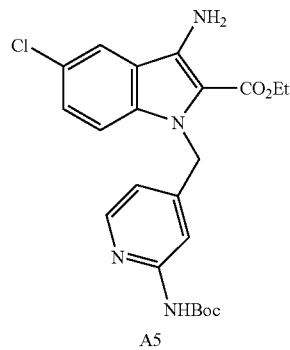

A5

To a solution of compound A4 (0.55 g, 1.16 mmol) in absolute ethanol (60 mL) at room temperature was added calcium chloride (60 mg, 0.52 mmol), water (10 mL) and iron powder (600 mg, 10.4 mmol). The resulting reaction was heated to reflux and allowed to stir at this temperature for 4 hours. The mixture was filtered through a celite pad and pad was rinsed with warm ethanol (100 mL). The filtrate was concentrated in vacuo to provide compound A5, which was used without further purification.

Step 4: Synthesis of Compound A6

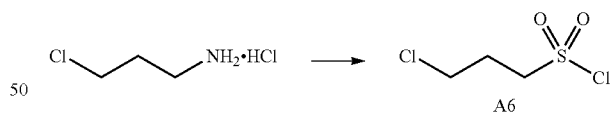

A6

To a stirred solution of 3-chloro-1-aminopropane hydrochloride (5.00 g, 38.5 mmol) in anhydrous acetonitrile (100 mL) at room temperature was added sulfuryl chloride (18.7 mL, 0.231 mol). The resulting reaction was heated to reflux and allowed to stir at this temperature for 18 hours. The reaction mixture was cooled to room temperature, concentrated in vacuo and the resulting residue was diluted with diethyl ether (200 mL). The resulting precipitate was filtered through a celite pad, the celite pad was washed with additional diethyl ether (100 mL) and the combined organic solutions were concentrated in vacuo. The residue obtained was dissolved in 100 mL anhydrous diethyl ether to make up a 0.326 M solution of compound A6 which was stored in a freezer and used without further purification.

Step 5: Synthesis of Compound A7:

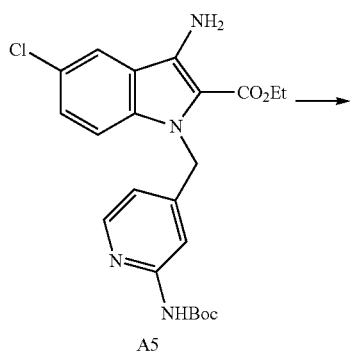

A solution of compound A5 (100 mg, 0.225 mmol) was dissolved in tetrahydrofuran (10 mL) at room temperature and the resulting solution was placed under nitrogen atmosphere. Triethylamine (0.060 mL, 0.45 mmol) was added to the reaction flask and the resulting reaction was cooled to −78° C. A solution of compound A6 (1.38 mL, 0.326 M, 0.450 mmol) was then added dropwise and after addition was complete, the reaction mixture was allowed to warm to room temperature then allowed to stir for an additional 4 hours. The reaction mixture was then concentrated in vacuo, the residue obtained was diluted with ethyl acetate (50 mL) and to the resulting solution was added saturated aqueous sodium carbonate solution (50 mL). After separation of layers, the aqueous layer was extracted with ethyl acetate (2×30 mL). The combined organic layers were dried over magnesium sulfate, filtered and concentrated in vacuo. The residue obtained was purified using flash column chromatography on silica gel (5-60% EtOAc/Hexanes) to provide compound A7 (110 mg, 82% yield). M.S. found for $C_{25}H_{31}Cl_2N_5O_6S$: 600.3 $(M+H)^+$.

Step 6: Synthesis of Compound A8:

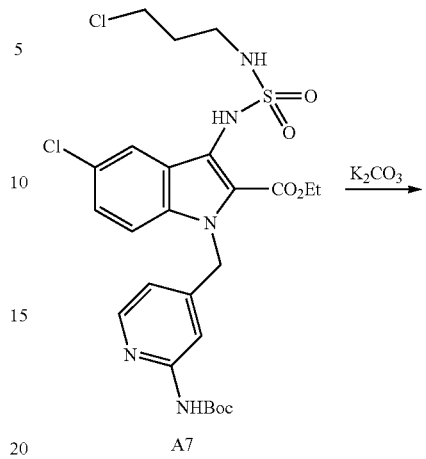

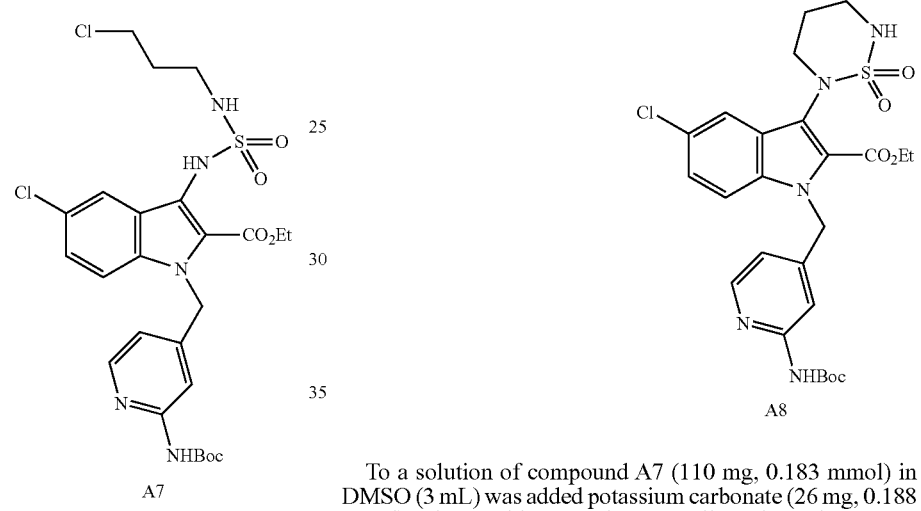

To a solution of compound A7 (110 mg, 0.183 mmol) in DMSO (3 mL) was added potassium carbonate (26 mg, 0.188 mmol). The resulting reaction was allowed to stir at mom temperature for 1.5 hours, then the reaction mixture was diluted with ethyl acetate (100 mL). The resulting solution was washed with water (3×80 mL) and the organic layer was dried over magnesium sulfate, filtered and concentrated in vacuo. The residue obtained was purified using flash column chromatography on silica gel (10-80% EtOAc/Hexanes) to provide compound A8 (90 mg, 87% yield). M.S. found for $C_{25}H_{30}ClN_5O_6S$: 564.3 $(M+H)^+$.

Step 7: Synthesis of Compound A9:

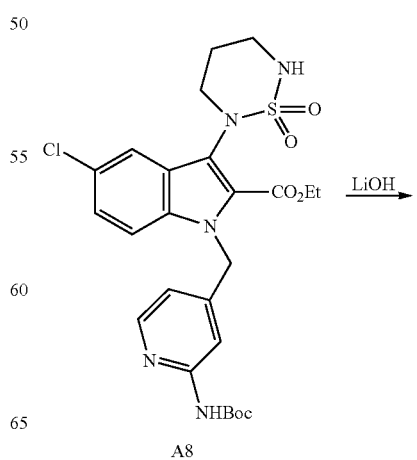

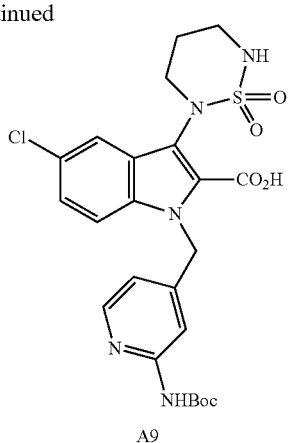

A9

To a solution of compound AS (90 mg, 0.160 mmol) in THF (2.0 mL) was added a solution of lithium hydroxide (9 mg, 0.21 mmol) in water (1.0 mL). The resulting reaction was stirred at room temperature for 3 hours, then acidified via addition of aqueous HCl (1 N, 0.7 mL). The resulting acidic solution was diluted with ethyl acetate (20 mL) and water (20 mL) and transferred to a separatory funnel. The organic layer was collected and the aqueous layer was extracted with ethyl acetate (2×20 mL). The combined organic layers were dried over magnesium sulfate, filtered and concentrated in vacuo to provide compound A9 (83 mg, 97% yield), which was used without further purification. M.S. found for $C_{23}H_{26}ClN_5O_6S$: 536.3 $(M+H)^+$.

Step 8: Synthesis of Compound A10:

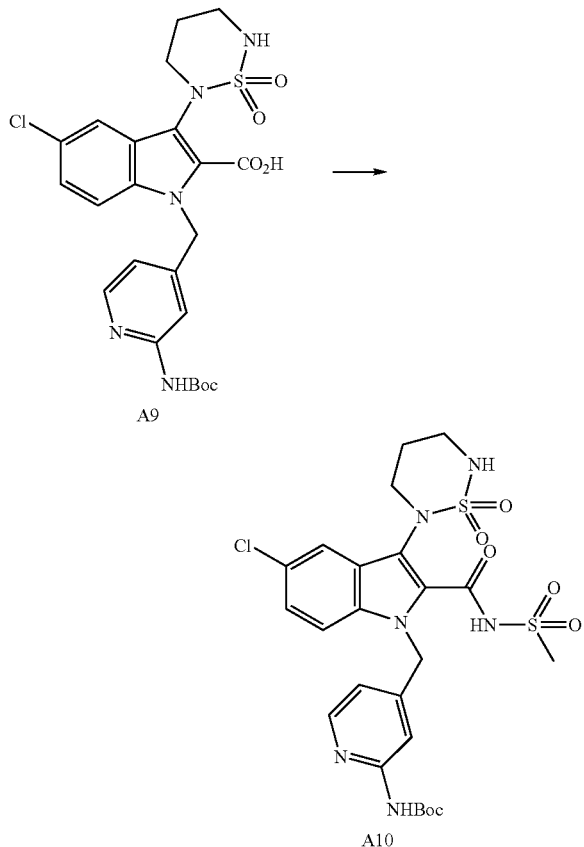

To a solution of compound A9 (75 mg, 0.14 mmol) in tetrahydrofuran (10 mL) was added carbonyldiimidazole (30 mg, 0.17 mmol). The resulting reaction was heated to reflux and allowed to stir at this temperature for 1 hour. The reaction mixture was then cooled to room temperature and methanesulfonamide (30 mg, 0.28 mmol) and 1,8-diazabicyclo(5.4.0)undec-7-ene (42 uL, 0.28 mmol) were added sequentially. The resulting reaction was stirred at room temperature for 18 hours, then diluted with ethyl acetate (50 mL), water (30 mL) and 5% aqueous phosphoric acid (5 mL). The resulting solution was transferred to a separatory funnel and the organic layer was collected. The aqueous layer was extracted with ethyl acetate (2×20 mL) and the combined organic layers were dried over magnesium sulfate, filtered and concentrated in vacuo. The residue obtained was purified using flash column chromatography (40-90% Acetone/Hexanes) on silica gel to provide compound A10 (40 mg, 47% yield). M.S. found for $C_{24}H_{29}ClN_6O_7S_2$: 613.3 $(M+H)^+$.

Step 9: Synthesis of Compound 6:

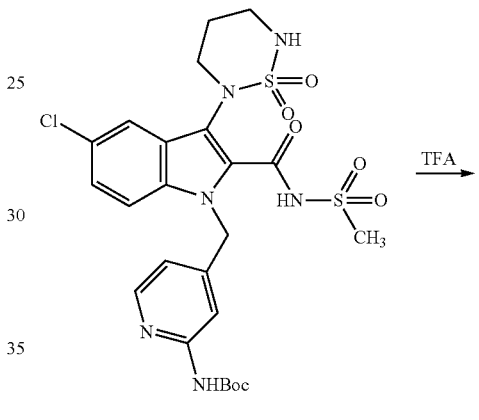

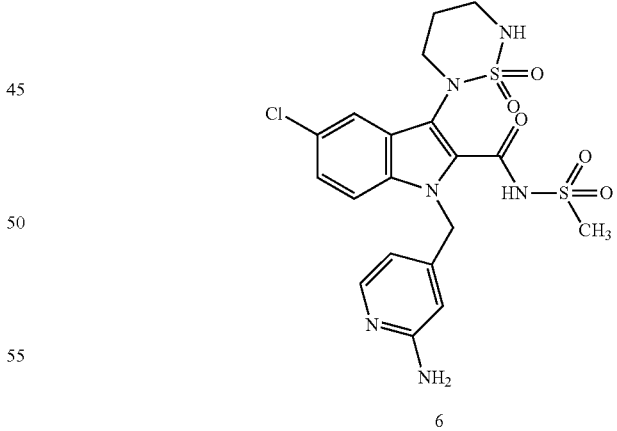

6

Compound A10 (20 mg, 0.0326mmol) was dissolved in trifluoroacetic acid (TFA) (2 mL) and the resulting reaction was allowed to stir at room temperature for 1 hour. The reaction mixture was concentrated in vacuo, and the resulting residue was purified using flash column chromatography on silica gel (5-100% methanol/dichloromethane) to provide compound 6 (12.6 mg, 75% yield). M.S. found for $C_{19}H_{21}ClN_6O_5S_2$: 513.3 $(M+H)^+$.

Example 2

HCV NS5E Polymerase Inhibition Assay

An in vitro transcribed heteropolymeric RNA known as D-RNA or DCoH has been shown to be an efficient template for HCV NS5B polymerase (S.-.E. Behrens et al., EMBO J. 15: 12-22 (1996); WO 96/37619). A chemically synthesized 75-mer version, designated DCoH75, whose sequence matches the 3'-end of D-RNA, and DCoH75ddC, where the 3'-terminal cytidine of DCoH75 is replaced by dideoxycytidine, were used for assaying the NS5B enzyme activity as described in Ferrari et al., 12$^{th}$ International Symposium on HCV and Related Viruses, P-306 (2005). A soluble C-terminal 21-amino acid truncated NS5B enzyme form (NS5B☐CT21) was produced and purified from Escherichia coli as C-terminal polyhistidine-tagged fusion protein as described in Ferrari et al., J. Virol. 73:1649-1654 (1999). A typical assay contained 20 mM Hepes pH 7.3, 10 mM $MgCl_2$, 60 mM NaCl, 100 μg/ml BSA, 20 units/ml RNasin, 7.5 mM DTT, 0.1 μM ATP/GTP/UTP, 0.026 μM CTP, 0.25 mM GALT, 0.03 μM RNA template, 20 μCi/ml [$^{33}$P]-CTP, 2% DMSO, and 30 or 150 nM NS5B enzyme. Reactions were incubated at 22° C. for 2 hours, then stopped by adding 150 mM EDTA, washed in DE81 filter plate in 0.5M di-basic sodium phosphate buffer, pH 7.0, and counted using Packard TopCount after the addition of scintillation cocktail. Polynucleotide synthesis was monitored by the incorporation of radiolabeled CTP. The effect of the 3-Aminosulfonyl Substituted Indole Derivatives on the polymerase activity was evaluated by adding various concentrations of a 3-Aminosulfonyl Substituted Indole Derivative, typically in 10 serial 2-fold dilutions, to the assay mixture. The starting concentrations of the indole derivatives ranged from 200 μM to 1 μM. An $IC_{50}$ value for the inhibitor, defined as the compound concentration that provides 50% inhibition of polymerase activity, was determined by fitting the cpm data to the Hill equation Y-100/(1+10^((LogIC50–X)*HillSlope)), where X is the logarithm of compound concentration, and Y is the % inhibition. Ferrari et al., 12$^{th}$ International Symposium on HCV and Related Viruses, P-306 (2005) described in detail this assay procedure. It should be noted that such an assay as described is exemplary and not intended to limit the scope of the invention. The skilled practitioner can appreciate that modifications including but not limited to RNA template, primer, nucleotides, NS5B polymerase form, buffer composition, can be made to develop similar assays that yield the same result for the efficacy of the compounds and compositions described in the invention.

NS5B polymerase inhibition data for selected 3-Aminosulfonyl Substituted Indole Derivatives of the present invention was obtained using the above method and calculated $IC_{50}$ values ranged from about 0.001 μM to about 25 μM.

Example 3

Cell-Based HCV Replicon Assay

To measure cell-based anti-HCV activity of the 3-Aminosulfonyl Substituted Indole Derivatives of the present invention, replicon cells are seeded at 5000 cells/well in 96-well collagen I-coated Nunc plates in the presence of the 3-Aminosulfonyl Substituted Indole Derivative. Various concentrations of a 3-Aminosulfonyl Substituted Indole Derivative, typically in 10 serial 2-fold dilutions, are then added to the assay mixture; the starting concentration of the test compound will range from 250 μμM to 1 μM. The final concentration in the assay media of DMSO is about 0.5% and of fetal bovine serum is about 5%. Cells are harvested on day 3 by the addition of lx cell lysis buffer (Ambion cat #8721). The replicon RNA level is measured using real time PCR (Taqman assay). The amplicon is located in 5B. The PCR primers are: 5B.2F, ATGGACAGGCGCCCTGA; 5B.2R, TTGATGGGCAGCTTGGTTTC; the probe sequence is FAM-labeled CACGCCATGCGCTGCGG. GAPDH RNA is used as endogenous control and is amplified in the same reaction as NS5B (multiplex PCR) using primers and VIC-labeled probe recommended by the manufacturer (PE Applied Biosystem). The real-time RT-PCR reactions can be run on an ABI PRISM 7900HT Sequence Detection System using the following program: 48° C. for 30 minutes, 95° C. for 10 minutes, 40 cycles of 95° C. for 15 see, 60° C. for 1 minute. The ΔCT values ($CT_{5B}$-$CT_{GAPDH}$) are then plotted against the concentration of test compound and fitted to the sigmoid dose-response model using XLfit4 (MDL). $EC_{50}$ is defined as the concentration of inhibitor necessary to achieve ΔCT=1 over the projected baseline; $EC_{90}$ the concentration necessary to achieve ΔCT=3.2 over the baseline. Alternatively, to quantitate the absolute amount of replicon RNA, a standard curve can be established by including serially diluted T7 transcripts of replicon RNA in the Tatman assay. Taqman reagents can be obtained from PE Applied Biosystems, Such an assay procedure is described in detail in e.g. Malcolm et al., Antimicrobial Agents and Chemotherapy 50: 1013-1020 (2006).

Uses of the 3-Aminosulfonyl Substituted Indole Derivatives

The 3-Aminosulfonyl Substituted Indole Derivatives are useful in human and veterinary medicine for treating or preventing a viral infection or a virus-related disorder in a patient. In accordance with the invention, the 3-Aminosulfonyl Substituted indole Derivatives can be administered to a patient in need of treatment or prevention of a viral infection or a virus-related disorder.

Accordingly, in one embodiment, the invention provides methods for treating a viral infection in a patient comprising administering to the patient an effective amount of at least one 3-Aminosulfonyl Substituted Indole Derivative or a pharmaceutically acceptable salt, solvate, ester or prodrug thereof. In another embodiment, the invention provides methods for treating a virus-related disorder M a patient comprising administering to the patient an effective amount of at least one 3-Aminosulfonyl Substituted Indole Derivative or a pharmaceutically acceptable salt, solvate, ester or prodrug thereof.

Treatment or Prevention of a Viral Infection

The 3-Aminosulfonyl Substituted Indole Derivatives can be used to treat or prevent a viral infection. In one embodiment, the 3-Aminosulfonyl Substituted indole Derivatives can be inhibitors of viral replication. In a specific embodiment, the 3-Aminosulfonyl Substituted Indole Derivatives can be inhibitors of HCV replication. Accordingly, the 3-Aminosulfonyl Substituted Indole Derivatives are useful for treating viral diseases and disorders related to the activity of a virus, such as HCV polymerase.

Examples of viral infections that can be treated or prevented using the present methods, include but are not limited to, hepatitis A infection, hepatitis B infection and hepatitis C infection.

In one embodiment, the viral infection is hepatitis C infection.

In one embodiment, the hepatitis C infection is acute hepatitis C. In another embodiment, the hepatitis C infection is chronic hepatitis C.

The compositions and combinations of the present invention can be useful for treating a patient suffering from infection related to any HCV genotype. HCV types and subtypes may differ in their antigenicity, level of viremia, severity of disease produced, and response to interferon therapy as described in Holland at al., *Pathology*, 30(2):192-195 (1998). The nomenclature set forth in Simmonds et al., *J Gen Virol*, 74(Pt11):2391-2399 (1993) is widely used and classifies isolates into six major genotypes, 1 through 6, with two or more related subtypes, e.g., 1a, 1b. Additional genotypes 7-10 and 11 have been proposed, however the phylogenetic basis on which this classification is based has been questioned, and thus types 7, 8, 9 and 11 isolates have been reassigned as type 6, and type 10 isolates as type 3 (see Lamballerie at al, *J Gen Virol*, 78(Pt1):45-51 (1997)). The major genotypes have been defined as having sequence similarities of between 55 and 72% (mean 64.5%), and subtypes within types as having 75%-86% similarity (mean 80%) when sequenced in the NS-5 region (see Simmonds et al., *J Gen Virol*, 75(Pt 5):1053-1061 (1994)).

Treatment or Prevention of a Virus-Related Disorder

The 3-Aminosulfonyl Substituted Indole Derivatives can be used to treat or prevent a virus-related disorder. Accordingly, the 3-Aminosulfonyl Substituted Indole Derivatives are useful for treating disorders related to the activity of a virus, such as liver inflammation or cirrhosis. Virus-related disorders include, but are not limited to, RNA-dependent polymerase-related disorders and disorders related to HCV infection.

Treatment or Prevention of a RNA-Dependent Polymerase-Related Disorder

The 3-Aminosulfonyl Substituted Indole Derivatives are useful for treating or preventing a RNA dependent polymerase (RdRp) related disorder in a patient. Such disorders include viral infections wherein the infective virus contain a RdRp enzyme.

Accordingly, in one embodiment, the present invention provides a method for treating a RNA dependent polymerase-related disorder in a patient, comprising administering to the patient an effective amount of at least one 3-Aminosulfonyl Substituted Indole Derivative or a pharmaceutically acceptable salt, solvate, ester or prodrug thereof.

Treatment or Prevention of a Disorder Related to HCV Infection

The 3-Aminosulfonyl Substituted Indole Derivatives can also be useful for treating or preventing a disorder related to an HCV infection. Examples of such disorders include, but are not limited to, cirrhosis, portal hypertension, ascites, bone pain, varices, jaundice, hepatic encephalopathy, thyroiditis, porphyria cutanea tarda, cryoglobulinemia, glomerulonephritis, sicca syndrome, thrombocytopenia, lichen planus and diabetes mellitus.

Accordingly, in one embodiment, the invention provides methods for treating an HCV-related disorder in a patient, wherein the method comprises administering to the patient a therapeutically effective amount of at least one 3-Aminosulfonyl Substituted Indole Derivative, or a pharmaceutically acceptable salt, solvate, ester or prodrug thereof.

Combination Therapy

In another embodiment, the present methods for treating or preventing a viral infection can further comprise the administration of one or more additional therapeutic agents which are not 3-Aminosulfonyl Substituted Indole Derivatives. In one embodiment, the additional therapeutic agent is an antiviral agent.

In another embodiment, the additional therapeutic agent is an immunomodulatory agent, such as an immunosuppressive agent.

Accordingly, in one embodiment, the present invention provides methods for treating a viral infection in a patient, the method comprising administering to the patient (i) at least one 3-Aminosulfonyl Substituted Indole Derivative, or a pharmaceutically acceptable salt, solvate, ester or prodrug thereof, and (ii) at least one other antiviral agent that is other than a 3-Aminosulfonyl Substituted Indole Derivative, wherein the amounts administered are together effective to treat or prevent a viral infection.

When administering a combination therapy of the invention to a patient, the therapeutic agents in the combination, or a pharmaceutical composition or compositions comprising the therapeutic agents, may be administered in any order such as, for example, sequentially, concurrently, together, simultaneously and the like. The amounts of the various actives in such combination therapy may be different amounts (different dosage amounts) or same amounts (same dosage amounts). Thus, for non-limiting illustration purposes, a 3-Aminosulfonyl Substituted Indole Derivative and an additional therapeutic agent may be present in fixed amounts (dosage amounts) in a single dosage unit (e.g., a capsule, a tablet and the like). A commercial example of such single dosage unit containing fixed amounts of two different active compounds is VYTORIN® (available from Merck Schering-Plough Pharmaceuticals, Kenilworth, N.J.).

In one embodiment, the at least one 3-Aminosulfonyl Substituted Indole Derivative is administered during at time when the additional antiviral agent(s) exert their prophylactic or therapeutic effect, or vice versa.

In another embodiment, the at least one 3-Aminosulfonyl Substituted Indole Derivative and the additional antiviral agent(s) are administered in doses commonly employed when such agents are used as monotherapy for treating a viral infection.

In another embodiment, the at least one 3-Aminosulfonyl Substituted indole Derivative and the additional antiviral agent(s) are administered in doses lower than the doses commonly employed when such agents are used as monotherapy for treating a viral infection.

In still another embodiment, the at least one 3-Aminosulfonyl Substituted Indole Derivative and the additional antiviral agent(s) act synergistically and are administered in doses lower than the doses commonly employed when such agents are used as monotherapy for treating a viral infection.

In one embodiment, the at least one 3-Aminosulfonyl Substituted Indole Derivative and the additional antiviral agent(s) are present in the same composition. In one embodiment, this composition is suitable for oral administration. In another embodiment, this composition is suitable for intravenous administration.

Viral infections and virus-related disorders that can be treated or prevented using the combination therapy methods of the present invention include, but are not limited to, those listed above.

In one embodiment, the viral infection is HCV infection.

The at least one 3-Aminosulfonyl Substituted Indole Derivative and the additional antiviral agent(s) can act additively or synergistically. A synergistic combination may allow the use of lower dosages of one or more agents and/or less frequent administration of one or more agents of a combination therapy. A lower dosage or less frequent administration of one or more agents may lower toxicity of the therapy without reducing the efficacy of the therapy.

In one embodiment, the administration of at least one 3-Aminosulfonyl Substituted Indole Derivative and the additional antiviral agent(s) may inhibit the resistance of a viral infection to these agents.

Non-limiting examples of other therapeutic agents useful in the present compositions and methods include an HCV polymerase inhibitor, an interferon, a viral replication inhibitor, an antisense agent, a therapeutic vaccine, a viral protease inhibitor, a virion production inhibitor, an antibody therapy (monoclonal or polyclonal), and any agent useful for treating an RNA-dependent polymerase-related disorder.

In one embodiment, the other antiviral agent is a viral protease inhibitor.

In another embodiment, the other antiviral agent is an HCV protease inhibitor.

In another embodiment, the other antiviral agent is an interferon.

In still another embodiment, the other antiviral agent is a viral replication inhibitor.

In another embodiment, the other antiviral agent is an antisense agent.

In another embodiment, the other antiviral agent is a therapeutic vaccine,

In a further embodiment, the other antiviral agent is an virion production inhibitor.

In another embodiment, the other antiviral agent is antibody therapy.

In another embodiment, the other antiviral agents comprise a protease inhibitor and a polymerase inhibitor.

In still another embodiment, the other antiviral agents comprise a protease inhibitor and immunosuppressive agent.

In yet another embodiment, the other antiviral agents comprise a polymerase inhibitor and an immunosuppressive agent.

In a further embodiment, the other antiviral agents comprise a protease inhibitor, a polymerase inhibitor and an immunosuppressive agent.

In another embodiment the other agent is ribavirin.

HCV polymerase inhibitors useful in the present methods and compositions include, but are not limited to VP-19744 (Wyeth/ViroPharma), HCV-796 (Wyeth/ViroPharma), NM-283 (Idenix/Novartis), R-1626 (Roche), MK-0608 (Merck), A848837 (Abbott), GSK-71185 (Glaxo SmithKline), XTL-2125 (XTL Biopharmaceuticals), and those disclosed in Ni et al., *Current Opinion in Drug Discovery and Development*, 7(4):446 (2004); Tan et al., *Nature Reviews*, 1:867 (2002); and Beaulieu et al., *Current Opinion in Investigational Drugs*, 5:838 (2004).

Interferons useful in the present methods and compositions include, but are not limited to, interferon alfa-2a, interferon alfa-2b, interferon alfacon-1 and PEG-interferon alpha conjugates. "PEG-interferon alpha conjugates" are interferon alpha molecules covalently attached to a PEG molecule. Illustrative PEG-interferon alpha conjugates include interferon alpha-2a (Roferon™, Hoffman La-Roche, Nutley, N.J.) in the form of pegylated interferon alpha-2a (e.g., as sold under the trade name Pegasys™), interferon alpha-2b (Intron™, from Schering-Plough Corporation) in the form of pegylated interferon alpha-2b (e.g., as sold under the trade name PEG-Intron™), interferon alpha-2c (Berofor Alpha™, Boehringer Ingelheim, Ingelheim, Germany), interferon alpha fusion polypeptides, or consensus interferon as defined by determination of a consensus sequence of naturally occurring interferon alphas (Infergen™, Amgen, Thousand Oaks, Calif.).

Antibody therapy agents useful in the present methods and compositions include, but Are not limited to, antibodies specific to 1L-1.0 (such as those disclosed in US Patent Publication No. US2005/0101770, humanized 12G8, a humanized monoclonal antibody against human IL-10, plasmids containing the nucleic acids encoding the humanized 12G8 light and heavy chains were deposited with the American Type Culture Collection (ATCC) as deposit numbers PTA-5923 and PTA-5922, respectively), and the like). Viral protease inhibitors useful in the present methods and compositions include, but are not limited to, NS3 serine protease inhibitors (including, but are not limited to, those disclosed in U.S. Pat. Nos. 7,012,066, 6,914,122, 6,911,428, 6,846,802, 6,838,475, 6,800,434, 5,017,380, 4,933,443, 4,812,561 and 4,634,697; and U.S. Patent Publication Nos. US20020160962, US20050176648 and US20050249702), HCV protease inhibitors (e.g., SCH503034 (Schering-Plough), VX-950 (Vertex), GS-9132 (Gilead/Achillion), ITMN-191 (InterMune/Roche)), amprenavir, atazanavir, fosemprenavir, indinavir, lopinavir, ritonavir, nelfinavir, saquinavir, tipranavir and TMC114.

Viral replication inhibitors useful in the present methods and compositions include, but are not limited to, NS3 helicase inhibitors, NS5A inhibitors, ribavirin, viramidine, A-831 (Arrow Therapeutics); an antisense agent or a therapeutic vaccine.

In one embodiment, viral replication inhibitors useful in the present methods and compositions include, but are not limited to, NS3 helicase inhibitors or NS5A inhibitors.

Examples of protease inhbitors useful in the present methods include, but are not limited to, an HCV protease inhibitor and a NS-3 serine protease inhbitor.

Examples of HCV protease inhbitors useful in the present methods include, but are not limited to, those disclosed in Landro et al., *Biochemistry*, 36(311:9340-9348 (1997); Ingallinella et al., *Biochemistry*, 37(25):8906-8914 (1998); Llinàs-Brunet et al., *Bioorg Med Chem Lett*, 8(13):1713-1718 (1998); Martin et al., *Biochemistry*, 37(33):11459-11468 (1998); Dimasi et al., *J Virol*, 71(10):7461-7469 (1997); Martin et al., *Protein Eng*, 10(5):607-614 (1997); Elzouki et al., *J Hepat*, 27(1):42-48 (1997); *BioWorld Today*, 9(217):4 (Nov. 10, 1998); and International Publication Nos. WO 98/14181; WO 98/17679, WO 98/17679, WO 98/22496 and WO 99,07734.

Further examples of protease inhibitors useful in the present methods include, but are not limited to, Additional examples of other therapeutic agents useful in the present methods include, but are not limited to, Levovirin™ (ICN Pharmaceuticals, Costa Mesa, Calif.), VP 50406™ (Viropharma, Incorporated, Exton, Pa.), ISIS 14803™ (ISIS Pharmaceuticals, Carlsbad, Calif.), Heptazyme™ (Ribozyme Pharmaceuticals, Boulder, Colo.), VX-950™ (Vertex Pharmaceuticals, Cambridge, Mass.), Thymosin™ (SeiClone Pharmaceuticals, San Mateo, Calif.), Maxamine™ (Maxim Pharmaceuticals, San Diego, Calif.), NKB-122 (JenKen Bioscience Inc., North Carolina), mycophenolate mofetil (Hoffman-LaRoche, Nutley, N.J.).

The doses and dosage regimen of the other agents used in the combination therapies of the present invention for the treatment or prevention of a viral infection can be determined by the attending clinician, taking into consideration the approved doses and dosage regimen in the package insert; the age, sex and general health of the patient; and the type and severity of the viral infection or related disease or disorder. When administered in combination, the 3-Aminosulfonyl Substituted indole Derivative(s) and the other agent(s) for treating diseases or conditions listed above can be administered simultaneously (i.e., in the same composition or in separate compositions one right after the other) or sequentially. This is particularly useful when the components of the combination are given on different dosing schedules, e.g., one component is administered once daily and another every six hours, or when the preferred pharmaceutical compositions are different, e.g. one is a tablet and one is a capsule. A kit comprising the separate dosage forms is therefore advantageous.

Generally, a total daily dosage of the at least one 3-Aminosulfonyl Substituted Indole Derivative and the additional antiviral agent(s), when administered as combination therapy, can range from about 0.1 to about 2000 mg per day, although variations will necessarily occur depending on the target of the therapy, the patient and the route of administration. In one embodiment, the dosage is from about 10 to about 500 mg/day, administered in a single dose or in 2-4 divided doses. In another embodiment, the dosage is from about 1 to about 200 mg/day, administered in a single dose or in 2-4 divided doses. In still another embodiment, the dosage is from about 1 to about 100 mg/day, administered in a single dose or in 2-4 divided doses. In yet another embodiment, the dosage is from about 1 to about 50 mg/day, administered in a single dose or in 2-4 divided doses. In a further embodiment, the dosage is from about 1 to about 20 mg/day, administered in a single dose or in 2-4 divided doses. In another embodiment, the dosage is from about 500 to about 1500 mg/day, administered in a single dose or in 2-4 divided doses. In still another embodiment, the dosage is from about 500 to about 1000 mg/day, administered in a single dose or in 2-4 divided doses. In yet another embodiment, the dosage is from about 100 to about 500 mg/day, administered in a single dose or in 2-4 divided doses.

In one embodiment, when the other therapeutic agent is INTRON-A interferon alpha 2b (commercially available from Schering-Plough Corp.), this agent is administered by subcutaneous injection at 3MIU(12 mcg)/0.5mL/TIW is for 24 weeks or 48 weeks for first time treatment.

In another embodiment, when the other therapeutic agent is PEG-INTRON interferon alpha 2b pegylated (commercially available from Schering-Plough Corp.), this agent is administered by subcutaneous injection at 1.5 mcg/kg/week, within a range of 40 to 150 mcg/week, for at least 24 weeks.

In another embodiment, when the other therapeutic agent is ROFERON A interferon alpha 2a (commercially available from Hoffmann-La Roche), this agent is administered by subcutaneous or intramuscular injection at 3MIU(11.1 mcg/mL)/TIW for at least 48 to 52 weeks, or alternatively 6MIU/TIW for 12 weeks followed by 3MIU/TIW for 36 weeks.

In still another embodiment, when the other therapeutic agent is PEGASUS interferon alpha 2a pegylated (commercially available from Hoffmann-La Roche), this agent is administered by subcutaneous injection at 180 mcg/1 mL or 180 mcg/0.5 mL, once a week for at least 24 weeks.

In yet another embodiment, when the other therapeutic agent is INFERGEN interferon alphacon-1 (commercially available from Amgen), this agent is administered by subcutaneous injection at 9 mcg/TIW is 24 weeks for first time treatment and up to 15 mcg/TIW for 24 weeks for non-responsive or relapse treatment.

In a further embodiment, when the other therapeutic agent is Ribavirin (commercially available as REBETOL ribavirin from Schering-Plough or COPEGUS ribavirin from Hoffmann-La Roche), this agent is administered at a daily dosage of from about 600 to about 1400 mg/day for at least 24 weeks.

Compositions and Administration

Due to their activity, the 3-Aminosulfonyl Substituted Indole Derivatives are useful in veterinary and human medicine. As described above, the 3-Aminosulfonyl Substituted Indole Derivatives are useful for treating or preventing a viral infection or a virus-related disorder in a patient in need thereof.

When administered to a patient, the IDs can be administered as a component of a composition that comprises a pharmaceutically acceptable carrier or vehicle. The present invention provides pharmaceutical compositions comprising an effective amount of at least one 3-Aminosulfonyl/Substituted Indole Derivative and a pharmaceutically acceptable carrier. In the pharmaceutical compositions and methods of the present invention, the active ingredients will typically be administered in admixture with suitable carrier materials suitably selected with respect to the intended form of administration, i.e. oral tablets, capsules (either solid-filled, semi-solid filled or liquid filled), powders for constitution, oral gels, elixirs, dispersible granules, syrups, suspensions, and the like, and consistent with conventional pharmaceutical practices. For example, for oral administration in the form of tablets or capsules, the active drug component may be combined with any oral non-toxic pharmaceutically acceptable inert carrier, such as lactose, starch, sucrose, cellulose, magnesium stearate, dicalcium phosphate, calcium sulfate, talc, mannitol, ethyl alcohol (liquid forms) and the like. Solid form preparations include powders, tablets, dispersible granules, capsules, cachets and suppositories. Powders and tablets may be comprised of from about 5 to about 95 percent inventive composition. Tablets, powders, cachets and capsules can be used as solid dosage forms suitable for oral administration.

Moreover, when desired or needed, suitable binders, lubricants, disintegrating agents and coloring agents may also be incorporated in the mixture. Suitable binders include starch, gelatin, natural sugars, corn sweeteners, natural and synthetic gums such as acacia, sodium alginate, carboxymethylcellulose, polyethylene glycol and waxes. Among the lubricants there may be mentioned for use in these dosage forms, boric acid, sodium benzoate, sodium acetate, sodium chloride, and the like. Disintegrants include starch, methylcellulose, guar gum and the like. Sweetening and flavoring agents and preservatives may also be included where appropriate.

Liquid form preparations include solutions, suspensions and emulsions and may include water or water-propylene glycol solutions for parenteral injection.

Liquid form preparations may also include solutions for intranasal administration.

Aerosol preparations suitable for inhalation may include solutions and solids in powder form, which may be in combination with a pharmaceutically acceptable carrier, such as an inert compressed gas.

Also included are solid fowl preparations which are intended to be converted, shortly before use, to liquid form in preparations for either oral or parenteral administration. Such liquid forms include solutions, suspensions and emulsions.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby solidify.

The 3-Aminosulfonyl Substituted Indole Derivatives of the present invention may also be deliverable transdermally. The transdermal compositions can take the form of creams, lotions, aerosols and/or emulsions and can be included in a transdermal patch of the matrix or reservoir type as are conventional in the art for this purpose.

Additionally, the compositions of the present invention may be formulated in sustained release form to provide the rate controlled release of any one or more of the components or active ingredients to optimize the therapeutic effects, i.e. anti-inflammatory activity and the like. Suitable dosage forms for sustained release include layered tablets containing layers of varying disintegration rates or controlled release polymeric matrices impregnated with the active components and shaped in tablet form or capsules containing such impregnated or encapsulated porous polymeric matrices.

In one embodiment, the one or more 3-Aminosulfonyl Substituted Indole Derivatives are administered orally.

In another embodiment, the one or more 3-Aminosulfonyl Substituted Indole Derivatives are administered intravenously.

In another embodiment, the one or more 3-Aminosulfonyl Substituted Indole. Derivatives are administered topically.

In still another embodiment, the one or more 3-Aminosulfonyl Substituted indole Derivatives are administered sublingually.

In one embodiment, a pharmaceutical preparation comprising at least one 3-Aminosulfonyl Substituted indole Derivative is in unit dosage form. In such form, the preparation is subdivided into unit doses containing appropriate quantities of the active component, e.g., an effective amount to achieve the desired purpose.

Compositions can be prepared according to conventional mixing, granulating or coating methods, respectively, and the present compositions can contain, in one embodiment, from about 0.1% to about 99% of the 3-Aminosuifonyl Substituted indole Derivative(s) by weight or volume. In various embodiments, the the present compositions can contain, in me embodiment, from about 1% to about 70% or from about 5% to about 60% of the 3-Aminosulfonyl Substituted Indole Derivative(s) by weight or volume.

The quantity of 3-Aminosulfonyl Substituted Indole Derivative in a unit dose of preparation may be varied or adjusted from about 0.1 mg to about 2000 mg. In various embodiment, the quantity is from about 1 mg to about 2000 mg, 100 mg to about 200 mg, 500 mg to about 2000 mg, 100 mg to about 1000 mg, and 1 mg to about 500 mg.

For convenience, the total daily dosage may be divided and administered in portions during the day if desired. In one embodiment, the daily dosage is administered in one portion. In another embodiment, the total daily dosage is administered in two divided doses over a 24 hour period. In another embodiment, the total daily dosage is administered in three divided doses over a 24 hour period. In still another embodiment, the total daily dosage is administered in four divided doses over a 24 hour period.

The amount and frequency of administration of the 3-Aminosulfonyl Substituted Indole Derivatives will be regulated according to the judgment of the attending clinician considering such factors as age, condition and size of the patient as well as severity of the symptoms being treated. Generally, a total daily dosage of the 3-Aminosulfonyl Substituted Indole Derivatives range from about 0.1 to about 2000 mg per day, although variations will necessarily occur depending on the target of the therapy, the patient and the route of administration. In one embodiment, the dosage is from about 1 to about 200 mg/day, administered in a single dose or in 2-4 divided doses. In another embodiment, the dosage is from about 10 to about 2000 mg/day, administered in a single dose or in 2-4 divided doses. In another embodiment, the dosage is from about 100 to about 2000 mg/day, administered in a single dose or in 2-4 divided doses. In still another embodiment, the dosage is from about 500 to about 2000 mg/day, administered in a single dose or in 2-4 divided doses.

The compositions of the invention can further comprise one or more additional therapeutic agents, selected from those listed above herein. Accordingly, in one embodiment, the present invention provides compositions comprising: (i) at least one 3-Aminosulfonyl Substituted Indole Derivative or a pharmaceutically acceptable salt, solvate, ester or prodrug thereof; (ii) one or more additional therapeutic agents that are not a 3-Aminosulfonyl Substituted Indole Derivative; and (iii) a pharmaceutically acceptable carrier, wherein the amounts in the composition are together effective to treat a viral infection or a virus-related disorder.

Kits

In one aspect, the present invention provides a kit comprising a therapeutically effective amount of at least one 3-Aminosulfonyl Substituted Indole Derivative, or a pharmaceutically acceptable salt, solvate, ester or prodrug of said compound and a pharmaceutically acceptable carrier, vehicle or diluent.

In another aspect the present invention provides a kit comprising an amount of at least one 3-Aminosulfonyl Substituted Indole Derivative, or a pharmaceutically acceptable salt, solvate, ester or prodrug of said compound and an amount of at least one additional therapeutic agent listed above, wherein the amounts of the two or more ingredients result in a desired therapeutic effect.

The present invention is not to be limited by the specific embodiments disclosed in the examples that are intended as illustrations of a few aspects of the invention and any embodiments that are functionally equivalent are within the scope of this invention. Indeed, various modifications of the invention in addition to those shown and described herein will become apparent to those skilled in the art and are intended to fall within the scope of the appended claims.

A number of references have been cited herein, the entire disclosures of which are incorporated herein by reference.

What is claimed is:

1. A compound having the formula:

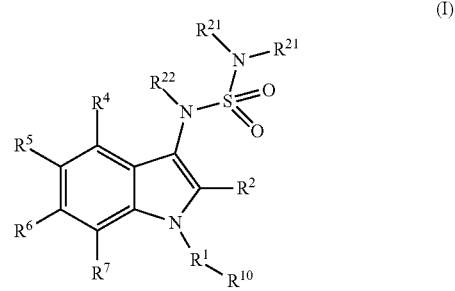

(I)

or a pharmaceutically acceptable salt thereof, wherein:

$R^1$ is a bond, $-[C(R^{12})_2]_r-$, $-[C(R^{12})_2]_r-O-[C(R^{12})_2]_q-$, $-[C(R^{12})_2]_r-N(R^9)-[C(R^{12})_2]_q-$, $-[C(R^{12})_2]_q-CH=CH-[C(R^{12})_2]_q-$, $-[C(R^{12})_2]_q-C\equiv C-[C(R^{12})_2]_q-$, or $-[C(R^{12})_2]_q-SO_2-[C(R^{12})_2]_q-$;

$R^2$ is $-[C(R^{12})_2]_q-C(O)N(R^9)SOR^{11}$, $-[C(R^{12})_2]_q-C(O)N(R^9)SO_2R^{11}$, $-[C(R^{12})_2]_q-C(O)N(R^9)SO_2N(R^9)_2$,

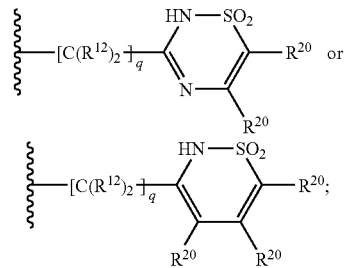

$R^4$, $R^5$, $R^6$ and $R^7$ are each, independently, H, alkyl, alkenyl, alkynyl, aryl, $-[C(R^{12})_2]_q$-cycloalkyl, $-[C(R^{12})_2]_q$-cycloalkenyl, $-[C(R^{12})_2]_q$-heterocycloalkyl, $-[C(R^{12})_2]_q$-heterocycloalkenyl, $-[C(R^{12})_2]_q$-heteroaryl, $-[C(R^{12})_2]_q$-haloalkyl, $-[C(R^{12})_2]_q$-hydroxyalkyl, halo, hydroxy, $-OR^9$, $-CN$, $-[C(R^{12})_2]_q-C(O)R^8$, $-[C(R^{12})_2]_q-C(O)OR^9$, $-[C(R^{12})_2]_q-C(O)N(R^9)_2$, $-[C(R^{12})_2]_q-OR^9$, $-[C(R^{12})_2]_q-N(R^9)_2$, $-[C(R^{12})_2]_q-NHC(O)R^8$, $-[C(R^{12})_2]_q-NR^8C(O)N(R^9)_2$, $-[C(R^{12})_2]_q-NHSO_2R^{11}$, $-[C(R^{12})_2]_q-S(O)_pR^{11}$, $-[C(R^{12})_2]_q-SO_2N(R^9)_2$ or $-SO_2N(R^9)C(O)N(R^9)_2$;

each occurrence of $R^8$ is independently H, alkyl, alkenyl, alkynyl, $-[C(R^{12})_2]_q$-aryl, $-[C(R^{12})_2]_q$-cycloalkyl, $-[C(R^{12})_2]_q$-cycloalkenyl, $-[C(R^{12})_2]_q$-heterocycloalkyl, $-[C(R^{12})_2]_q$-heterocycloalkenyl, $-[C(R^{12})_2]_q$-heteroaryl, haloalkyl or hydroxyalkyl;

each occurrence of $R^9$ is independently H, alkyl, alkenyl, alkynyl, $-[C(R^{12})_2]_q$-aryl, $-[C(R^{12})_2]_q$-cycloalkyl, $-[C(R^{12})_2]_q$-cycloalkenyl, $-[C(R^{12})_2]_q$-heterocycloalkyl, $-[C(R^{12})_2]_q$-heterocycloalkenyl, $-[C(R^{12})_2]_q$-heteroaryl, haloalkyl or hydroxyalkyl;

$R^{10}$ is H, cycloalkyl, cycloalkenyl, heterocycloalkyl, heterocycloalkenyl, aryl, heteroaryl, wherein a cycloalkyl, cycloalkenyl, heterocycloalkyl, heterocycloalkenyl, aryl or heteroaryl group can be optionally and independently substituted with up to 4 substituents, which are each independently selected from H, alkyl, alkenyl, alkynyl, aryl, $-[C(R^{12})_2]_q$-cycloalkyl, $-[C(R^{12})_2]_q$-cycloalkenyl, $-[C(R^{12})_2]_q$-heterocycloalkyl, $-[C(R^{12})_2]_q$-heterocycloalkenyl, $-[C(R^{12})_2]_q$-heteroaryl, $-[C(R^{12})_2]_q$-haloalkyl, $-[C(R^{12})_2]_q$-hydroxyalkyl, halo, hydroxy, $-OR^9$, $-CN$, $-[C(R^{12})_2]_q-C(O)R^8$, $-[C(R^{12})_2]_q-C(O)OR^9$, $-[C(R^{12})_2]_q-C(O)N(R^9)_2$, $-[C(R^{12})_2]_q-OR^9$, $-[C(R^{12})_2]_q-N(R^9)_2$, $-[C(R^{12})_2]_q-NHC(O)R^8$, $-[C(R^{12})_2]_q-NR^8C(O)N(R^9)_2$, $-[C(R^{12})_2]_q-NHSO_2R^{11}$, $-[C(R^{12})_2]_q-S(O)_pR^{11}$, $-[C(R^{12})_2]_q-SO_2N(R^9)_2$ and $-SO_2N(R^9)C(O)N(R^9)_2$, such that when $R^1$ is a bond, $R^{10}$ is not H;

each occurrence of $R^{11}$ is independently alkyl, aryl, cycloalkyl, cycloalkenyl, heterocycloalkyl, heterocycloalkenyl, heteroaryl, haloalkyl, hydroxy or hydroxyalkyl, wherein a cycloalkyl, cycloalkenyl, heterocycloalkyl, heterocycloalkenyl, aryl or heteroaryl group can be optionally and independently substituted with up to 4 substituents, which are each independently selected from $-H$, alkyl, alkenyl, alkynyl, aryl, $-[C(R^{12})_2]_q$-cycloalkyl, $-[C(R^{12})_2]_q$-cycloalkenyl, $-[C(R^{12})_2]_q$-heterocycloalkyl, $-[C(R^{12})_2]_q$-heterocycloalkenyl, $-[C(R^{12})_2]_q$-heteroaryl, $-[C(R^{12})_2]_q$-haloalkyl, $-[C(R^{12})_2]_q$-hydroxyalkyl, halo, hydroxy, $-OR^9$, $-CN$, $-[C(R^{12})_2]_q-C(O)R^8$, $-[C(R^{12})_2]_q-C(O)OR^9$, $-[C(R^{12})_2]_q-C(O)N(R^9)_2$, $-[C(R^{12})_2]_q-OR^9$, $-[C(R^{12})_2]_q-N(R^9)_2$, $-[C(R^{12})_2]_q-NHC(O)R^8$, $-[C(R^{12})_2]_q-NR^8C(O)N(R^9)_2$, $-[C(R^{12})_2]_q-NHSO_2$alkyl, $-[C(R^{12})_2]_q-NHSO_2$cycloalkyl, $-[C(R^{12})_2]_q-NHSO_2$aryl, $-[C(R^{12})_2]_q-SO_2N(R^9)_2$ and $-SO_2N(R^9)C(O)N(R^9)_2$;

each occurrence of $R^{12}$ is independently H, halo, $-N(R^9)_2$, $-OR^9$, alkyl, cycloalkyl, cycloalkenyl, heterocycloalkyl or heterocycloalkenyl, wherein a cycloalkyl, cycloalkenyl, heterocycloalkyl or heterocycloalkenyl group can be optionally and independently substituted with up to 4 substituents, which are each independently selected from alkyl, halo, haloalkyl, hydroxyalkyl, hydroxy, $-CN$, $-C(O)$alkyl, $-C(O)O$alkyl, $-C(O)NH$alkyl, $-C(O)N(\text{alkyl})_2$, $-O$-alkyl, $-NH_2$, $-NH(\text{alkyl})$, $-N(\text{alkyl})_2$, $-NHC(O)$alkyl, $-NHSO_2$alkyl, $-SO_2$alkyl or $-SO_2NH$-alkyl, or two $R^{12}$ groups, together with the carbon atoms to which they are attached, join to form a cycloalkyl, heterocycloalkyl or $C=O$ group;

each occurrence of $R^{20}$ is independently alkyl, aryl, cycloalkyl, heterocycloalkyl or heteroaryl, or both $R^{20}$ groups and the carbon atoms to which they are attached, join to form a cycloalkyl, cycloheteroalkyl, aryl or heteroaryl group wherein a cycloalkyl, cycloheteroalkyl, aryl or heteroaryl group can be substituted with up to 4 groups, which are each independently selected from alkyl, alkenyl, alkynyl, halo, hydroxy, $-OR^9$, $-CN$, $-[C(R^{12})_2]_q$-cycloalkyl, $-[C(R^{12})_2]_q$-cycloalkenyl, $-[C(R^{12})_2]_q$-heterocycloalkyl, $-[C(R^{12})_2]_q$-heterocycloalkenyl, $-[C(R^{12})_2]_q$-haloalkyl, $-[C(R^{12})_2]_q$-hydroxyalkyl, $-[C(R^{12})_2]_q-C(O)R^8$, $-[C(R^{12})_2]_q-C(O)OR^9$, $-[C(R^{12})_2]_q-C(O)N(R^9)_2$, $-[C(R^{12})_2]_q-OR^9$, $-[C(R^{12})_2]_q-N(R^9)_2$, $-[C(R^{12})_2]_q-NHC(O)R^8$, $-[C(R^{12})_2]_q-NR^8C(O)N(R^9)_2$, $-[C(R^{12})_2]_q-NHSO_2R^{11}$, $-[C(R^{12})_2]_q-S(O)_pR^{11}$, $-[C(R^{12})_2]_q-SO_2N(R^9)_2$ and $-SO_2N(R^9)C(O)N(R^9)_2$;

$R^{21}$ is H, alkyl, aryl, cycloalkyl, heterocycloalkyl, heteroaryl or haloalkyl, or $R^{21}$ and $R^{22}$ and the nitrogen atoms to which they are attached, join to form a group having the formula:

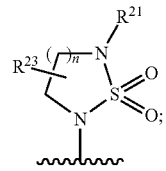

$R^{22}$ is H, alkyl, aryl, cycloalkyl, heterocycloalkyl, heteroaryl or haloalkyl;

$R^{23}$ is an optional substituent selected from alkyl, aryl, $-CN$, $-OH$, $-O$-alkyl, cycloalkyl, halo, heterocycloalkyl, and heteroaryl;

n is an integer ranging from 1 to 3;

each occurrence of p is independently 0, 1 or 2;

each occurrence of q is independently an integer ranging from 0 to 4; and each occurrence of r is independently an integer ranging from 1 to 4.

2. The compound of claim 1, wherein $R^2$ is —C(O)NHSO$_2$R$^{11}$ or —C(O)NHSO$_2$N(R$^9$)$_2$ wherein R$^9$ is H, alkyl, aryl, cycloalkyl, heteroaryl or heterocycloalkyl, and R$^{11}$ is alkyl, aryl, cycloalkyl, haloalkyl, heteroaryl, heterocycloalkyl or hydroxyalkyl.

3. The compound of claim 2, wherein $R^{21}$ and $R^{22}$ and the nitrogen atoms to which they are attached, join to from a group having the formula:

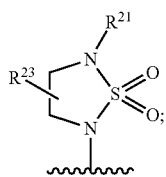

$R^{21}$ is H, alkyl, haloalkyl, and heterocycloalkyl; and
$R^{23}$ represents up to 4 optional and additional substituents each independently selected from H, alkyl, halo, haloalkyl, hydroxyl, and heterocycloalkyl.

4. The compound of claim 2, wherein $R^1$ is —CH$_2$—.

5. The compound of claim 2, wherein $R^4$ and $R^7$ are each independently H, alkyl, halo or hydroxy;
$R^5$ is H, alkyl, —O-alkyl, —O-haloalkyl, cycloalkyl, halo, haloalkyl, hydroxy, hydroxyalkyl, —NH$_2$ or —CN; and
$R^6$ is H, alkyl, —O-alkyl, —O-haloalkyl, cycloalkyl, halo, haloalkyl, hydroxy, hydroxyalkyl, —NH$_2$ or —CN.

6. The compound of claim 2, wherein $R^{10}$ is aryl or heteroaryl.

7. The compound of claim 1 having the formula:

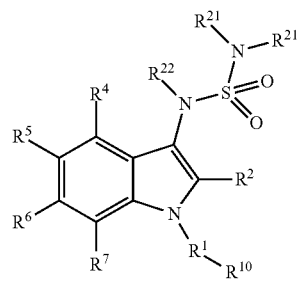

or a pharmaceutically acceptable salt, thereof, wherein:
$R^1$ is —CH$_2$—, —CH$_2$CH$_2$—, —CH(CH$_3$)—, —C(CH$_3$)$_2$—, or

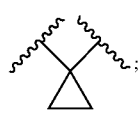 [SMILES: *C1(*)CC1]

$R^2$ is —C(O)NHSO$_2$R$^{11}$, —C(O)NHSO$_2$N(R$^9$)$_2$, —C(O)N(alkyl)SO$_2$R$^{11}$ or —C(O)N(alkyl)SO$_2$N(R$^9$)$_2$;
$R^4$, $R^5$, $R^6$ and $R^7$ are each, independently, H, alkyl, —[C(R$^{12}$)$_2$]$_q$-cycloalkyl, —[C(R$^{12}$)$_2$]$_q$-heterocycloalkyl, haloalkyl, halo, hydroxy, —OR$^9$ or —N(R$^9$)$_2$;
each occurrence of R$^9$ is independently H, alkyl, cycloalkyl, heterocycloalkyl, haloalkyl or hydroxyalkyl;

$R^{10}$ is:

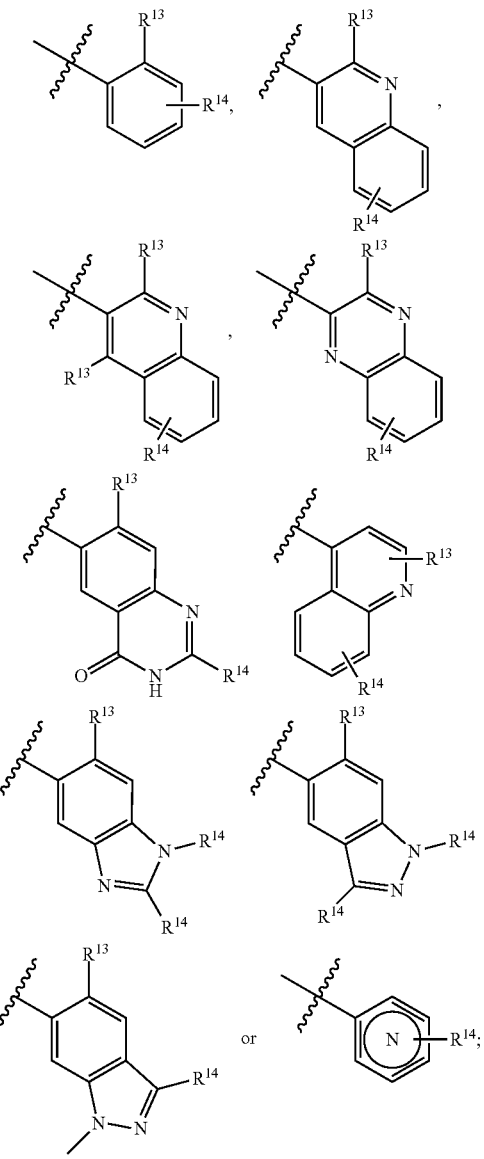

each occurrence of R$^{11}$ is independently alkyl, aryl, cycloalkyl, haloalkyl, heteroaryl, heterocycloalkyl or hydroxyalkyl;

each occurrence of R$^{12}$ is independently H, halo, —N(alkyl)$_2$, —OH, —O-alkyl, alkyl, cycloalkyl or heterocycloalkyl, or two R$^{12}$ groups, together with the carbon atoms to which they are attached, join to form a cycloalkyl, heterocycloalkyl or C═O group;

$R^{13}$ is H, F, Br or Cl;

$R^{14}$ represents up to 4 optional and additional substituents, each independently selected from alkyl, cycloalkyl, CF$_3$, —CN, halo, —O-alkyl, —O-haloalkyl, —NHSO$_2$-alkyl, —NO$_2$, —C(O)NH$_2$, —C(O)NH-alkyl, —C(O)OH, hydroxy, —NH$_2$, —SO$_2$alkyl, —SO$_2$NHalkyl, —S-alkyl, —CH$_2$NH$_2$, —CH$_2$OH, —SO$_2$NH$_2$, —NHC(O)-alkyl, —C(O)O-alkyl, —C(O) heterocycloalkyl and heteroaryl;

$R^{21}$ is H, alkyl, haloalkyl, and heterocycloalkyl or $R^{21}$ $R^{22}$ and the nitrogen atoms to which they are attached, join to from a group having the formula:

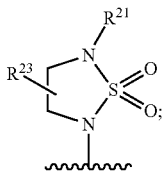

$R^{23}$ represents up to 4 optional and additional substituents each independently selected from H, alkyl, halo, hydroxyl, and heterocycloalkyl;

each occurrence of q is independently an integer ranging from 0 to 4; and

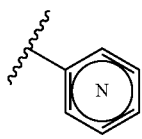

represents a pyridyl group, wherein the ring nitrogen atom can be at any of the five unsubstituted ring atom positions.

8. A compound having the formula:

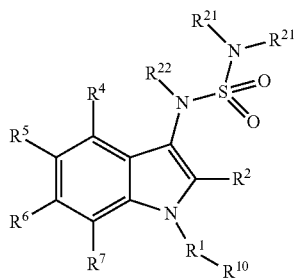

(II)

or a pharmaceutically acceptable salt thereof, wherein:

$R^1$ is a bond, $-[C(R^{12})_2]_r-$, $-[C(R^{12})_2]_r-O-[C(R^{12})_2]_q-$, $-[C(R^{12})_2]_r-N(R^9)-[C(R^{12})_2]_q-$, $-[C(R^{12})_2]_q-CH=CH-[C(R^{12})_2]_q-$, $-[C(R^{12})_2]_q-C\equiv C-[C(R^{12})_2]_q-$, or $-[C(R^{12})_2]_q-SO_2-[C(R^{12})_2]_q-$;

$R^2$ is $-C(O)R^9$, $-C(O)OR^9$, $-C(O)OCH_2OR^9$, $-C(O)N(R^9)_2$, $-[C(R^{12})_2]_q-C(O)OR^9$, $-[C(R^{12})_2]_q-C(O)N(R^9)_2$, -alkyl, $-[C(R^{12})_2]_q$-aryl, $-[C(R^{12})_2]_q$-cycloalkyl, $-[C(R^{12})_2]_q$-cycloalkenyl, $-[C(R^{12})_2]_q$-heterocycloalkyl, $-[C(R^{12})_2]_q$-heteroaryl or $-[C(R^{12})_2]_q$-heterocycloalkenyl, wherein an aryl, cycloalkyl, cycloalkenyl, heterocycloalkyl, heterocycloalkenyl or heteroaryl group can be optionally substituted with up to 4 substituents, which are the same or different, and are selected from alkyl, alkenyl, alkynyl, aryl, $-[C(R^{12})_2]_q$-cycloalkyl, $-[C(R^{12})_2]_q$-cycloalkenyl, $-[C(R^{12})_2]_q$-heterocycloalkyl, $-[C(R^{12})_2]_q$-heterocycloalkenyl, $-[C(R^{12})_2]_q$-heteroaryl, $-[C(R^{12})_2]_q$-haloalkyl, $-[C(R^{12})_2]_q$-hydroxyalkyl, halo, hydroxy, $-OR^9$, $-CN$, $-[C(R^{12})_2]_q-C(O)R^8$, $-[C(R^{12})_2]_q-C(O)OR^9$, $-[C(R^{12})_2]_q-C(O)N(R^9)_2$, $-[C(R^{12})_2]_q-OR^9$, $-[C(R^{12})_2]_q-N(R^9)_2$, $-[C(R^{12})_2]_q-NHC(O)R^8$, $-[C(R^{12})_2]_q-NR^8C(O)N(R^9)_2$, $-[C(R^{12})_2]_q-NHSO_2R^{11}$, $-[C(R^{12})_2]_q-S(O)_pR^{11}$, $-[C(R^{12})_2]_q-SO_2N(R^9)_2$ and $-SO_2N(R^9)C(O)N(R^9)_2$;

$R^4$ is H, alkyl, halo or hydroxy;

$R^5$ is H, alkyl, $-$O-alkly, $-$O-haloalkyl, cycloalkyl, halo, haloalkyl, hydroxy, hydroxyalkyl, $-NH_2$ or $-CN$;

$R^6$ is H, alkyl, $-$O-alkyl, $-$O-haloalkyl, cycloalkyl, halo, haloalky, hydroxy, hydroxyalkyl, $-NH_2$ or $-CN$;

$R^7$ is H, alkyl, halo or hydroxy;

each occurrence of $R^8$ is independently H, alkyl, alkenyl, alkynyl, $-[C(R^{12})_2]_q$-aryl, $-[C(R^{12})_2]_q$-cycloalkyl, $-[C(R^{12})_2]_q$-cycloalkenyl, $-[C(R^{12})_2]_q$-heterocycloalkyl, $-[C(R^{12})_2]_q$-heterocycloalkenyl, $-[C(R^{12})_2]_q$-heteroaryl, haloalkyl or hydroxyalkyl;

each occurrence of $R^9$ is independently H, alkyl, alkenyl, alkynyl, $-[C(R^{12})_2]_q$-aryl, $-[C(R^{12})_2]_q$-cycloalkyl, $-[C(R^{12})_2]_q$-cycloalkenyl, $-[C(R^{12})_2]_q$-heterocycloalkyl, $-[C(R^{12})_2]_q$-heterocycloalkenyl, $-[C(R^{12})_2]_q$-heteroaryl, haloalkyl or hydroxyalkyl;

$R^{10}$ is H, cycloalkyl, cycloalkenyl, heterocycloalkyl, heterocycloalkenyl, aryl, heteroaryl, wherein a cycloalkyl, cycloalkenyl, heterocycloalkyl, heterocycloalkenyl, aryl or heteroaryl group can be optionally and independently substituted with up to 4 substituents, which are each independently selected from $-H$, alkyl, alkenyl, alkynyl, aryl, $-[C(R^{12})_2]_q$-cycloalkyl, $-[C(R^{12})_2]_q$-cycloalkenyl, $-[C(R^{12})_2]_q$-heterocycloalkyl, $-[C(R^{12})_2]_q$-heterocycloalkenyl, $-[C(R^{12})_2]_q$-heteroaryl, $-[C(R^{12})_2]_q$-haloalkyl, $-[C(R^{12})_2]_q$-hydroxyalkyl, halo, hydroxy, $-OR^9$, $-CN$, $-[C(R^{12})_2]_q-C(O)R^8$, $-[C(R^{12})_2]_q-C(O)OR^9$, $-[C(R^{12})_2]_q-C(O)N(R^9)_2$, $-[C(R^{12})_2]_q-OR^9$, $-[C(R^{12})_2]_q-N(R^9)_2$, $-[C(R^{12})_2]_q-NHC(O)R^8$, $-[C(R^{12})_2]_q-NR^8C(O)N(R^9)_2$, $-[C(R^{12})_2]_q-NHSO_2R^{11}$, $-[C(R^{12})_2]_q-S(O)_pR^{11}$, $-[C(R^{12})_2]_q-SO_2N(R^9)_2$ and $-SO_2N(R^9)C(O)N(R^9)_2$, such that when $R^1$ is a bond, $R^{10}$ is not H;

each occurrence of $R^{11}$ is independently alkyl, aryl, cycloalkyl, cycloalkenyl, heterocycloalkyl, heterocycloalkenyl, heteroaryl, haloalkyl, hydroxy or hydroxyalkyl, wherein a cycloalkyl, cycloalkenyl, heterocycloalkyl, heterocycloalkenyl, aryl or heteroaryl group can be optionally and independently substituted with up to 4 substituents, which are each independently selected from $-H$, alkyl, alkenyl, alkynyl, aryl, $-[C(R^{12})_2]_q$-cycloalkyl, $-[C(R^{12})_2]_q$-cycloalkenyl, $-[C(R^{12})_2]_q$-heterocycloalkyl, $-[C(R^{12})_2]_q$-heterocycloalkenyl, $-[C(R^{12})_2]_q$-heteroaryl, $-[C(R^{12})_2]_q$-haloalkyl, $-[C(R^{12})_2]_q$-hydroxyalkyl, halo, hydroxy, $-OR^9$, $-CN$, $-[C(R^{12})_2]_q-C(O)R^8$, $-[C(R^{12})_2]_q-C(O)OR^9$, $-[C(R^{12})_2]_q-C(O)N(R^9)_2$, $-[C(R^{12})_2]_q-OR^9$, $-[C(R^{12})_2]_q-N(R^9)_2$, $-[C(R^{12})_2]_q-NHC(O)R^8$, $-[C(R^{12})_2]_q-NR^8C(O)N(R^9)_2$, $-[C(R^{12})_2]_q-NHSO_2$alkyl, $-[C(R^{12})_2]_q-NHSO_2$cycloalkyl, $-[C(R^{12})_2]_q-NHSO_2$aryl, $-[C(R^{12})_2]_q-SO_2N(R^9)_2$ and $-SO_2N(R^9)C(O)N(R^9)_2$;

each occurrence of $R^{12}$ is independently H, halo, $-N(R^9)_2$, $-OR^9$, alkyl, cycloalkyl, cycloalkenyl, heterocycloalkyl or heterocycloalkenyl, wherein a cycloalkyl, cycloalkenyl, heterocycloalkyl or heterocycloalkenyl group can be optionally and independently substituted with up to 4 substituents, which are each independently selected from alkyl, halo, haloalkyl, hydroxyalkyl, hydroxy, $-CN$, $-C(O)$alkyl, $-C(O)$Oalkyl, $-C(O)NH$alkyl, $-C(O)N($alkyl$)_2$, $-O$-alkyl, —NH$_2$, —NH(alkyl), —N(alkyl)$_2$, —NHC(O)alkyl, —NHSO$_2$alkyl, —SO$_2$alkyl or —SO$_2$NH-alkyl, or two R$^{12}$ groups, together with the carbon atoms to which they are attached, join to form a cycloalkyl, heterocycloalkyl or C=O group;

R$^{21}$ is H, alkyl, aryl, cycloalkyl, heterocycloalkyl, heteroaryl or haloalkyl, or R$^{21}$ and R$^{22}$ and the nitrogen atoms to which they are attached, join to form a group having the formula:

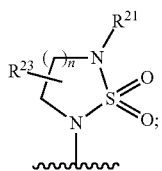

R$^{22}$ is H, alkyl, aryl, cycloalkyl, heterocycloalkyl, heteroaryl or haloalkyl;

R$^{23}$ is an optional substituent selected from alkyl, aryl, —CN, —OH, —O-alkyl, cycloalkyl, halo, heterocycloalkyl, and heteroaryl;

n is an integer ranging from 1 to 3;

each occurrence of p is independently 0, 1 or 2;

each occurrence of q is independently an integer ranging from 0 to 4; and each occurrence of r is independently an integer ranging from 1 to 4.

9. The compound of claim 8, wherein R$^2$ is —C(O)OR$^9$ or —C(O)N(R$^9$)$_2$, wherein R$^9$ is H, alkyl, aryl, cycloalkyl, heteroaryl or heterocycloalkyl.

10. The compound of claim 9, wherein R$^{21}$ and R$^{22}$ and the nitrogen atoms to which they are attached, join to form a group having the formula:

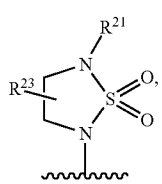

wherein R$^{21}$ is H, alkyl, haloalkyl, and heterocycloalkyl; and

R$^{23}$ represents up to 4 optional and additional substituents each independently selected from H, alkyl, halo, hydroxyl, and heterocycloalkyl.

11. The compound of claim 9, wherein R$^1$ is —CH$_2$—, —CH$_2$CH$_2$—, —CH(CH$_3$)—, —C(CH$_3$)$_2$—, or

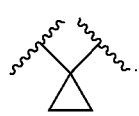

12. The compound of claim 9, wherein R$^{10}$ is aryl or heteroaryl.

13. The compound of claim 8 having the formula:

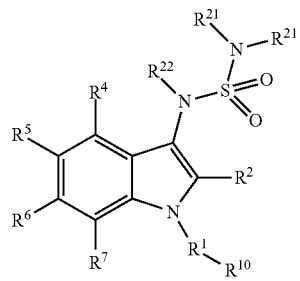

or a pharmaceutically acceptable salt thereof, wherein:

R$^1$ is —CH$_2$—, —CH$_2$CH$_2$—, —CH(CH$_3$)—, —C(CH$_3$)$_2$—, or

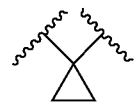

R$^2$ is —C(O)OR$^9$ or —C(O)N(R$^9$)$_2$, wherein R$^9$ is H, alkyl, aryl, cycloalkyl, heteroaryl or heterocycloalkyl;

R$^4$, R$^5$, R$^6$ and R$^7$ are each, independently, H, alkyl, —[C(R$^{12}$)$_2$]$_q$-cycloalkyl, —[C(R$^{12}$)$_2$]$_q$-heterocycloalkyl, haloalkyl, halo, hydroxy, —OR$^9$ or —N(R$^9$)$_2$;

each occurrence of R$^9$ is independently H, alkyl, cycloalkyl, heterocycloalkyl, haloalkyl or hydroxyalkyl;

R$^{10}$ is:

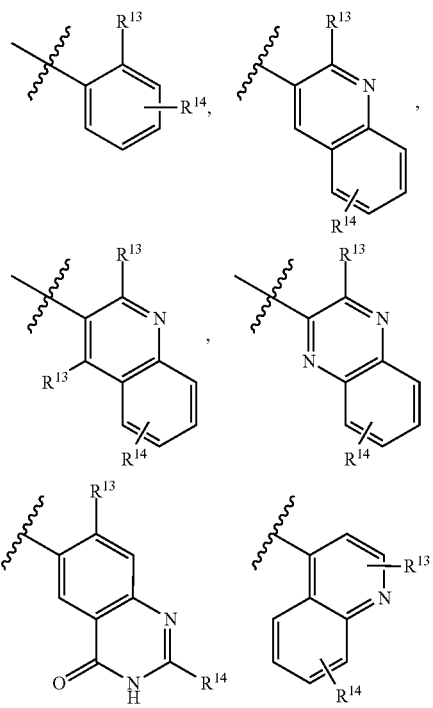

99

-continued

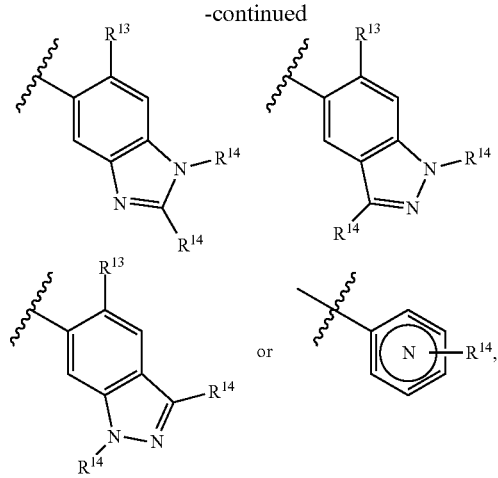

such that when R¹ is a bond, R¹⁰ is not H;
each occurrence of R¹¹ is independently alkyl, aryl, cycloalkyl, haloalkyl, heteroaryl, heterocycloalkyl or hydroxyalkyl;
each occurrence of R¹² is independently H, halo, —N(alkyl)₂, —OH, —O-alkyl, alkyl, cycloalkyl or heterocycloalkyl, or two R¹² groups, together with the carbon atoms to which they are attached, join to form a cycloalkyl, heterocycloalkyl or C=O group;
R¹³ is H, F, Br or Cl;
R¹⁴ represents up to 4 optional and additional substituents, each independently selected from alkyl, cycloalkyl, CF₃, —CN, halo, —O-alkyl, —O-haloalkyl, —NHSO₂-alkyl, —C(O)NH₂, —C(O)NH-alkyl, —C(O)OH, hydroxy, —NH₂, —SO₂alkyl, —SO₂NHalkyl, —S-alkyl, —CH₂NH₂, —CH₂OH, —SO₂NH₂, —NHC(O)-alkyl, —C(O)O-alkyl, —C(O)-heterocycloalkyl and heteroaryl;
R²¹ is H, alkyl, haloalkyl, and heterocycloalkyl or R²¹ and R²² and the nitrogen atoms to which they are attached, join to from a group having the formula:

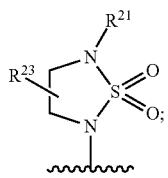

R²³ represents up to 4 optional and additional substituents each independently selected from H, alkyl, halo, —OH and heterocycloalkyl;
each occurrence of q is independently an integer ranging from 0 to 4; and

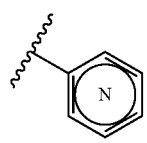

represents a pyridyl group, wherein the ring nitrogen atom can be at any of the five unsubstituted ring atom positions.

100

14. A compound having the structure:

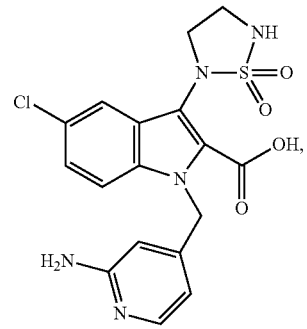

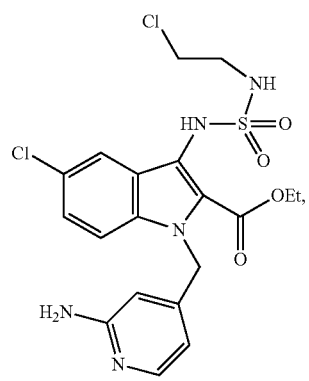

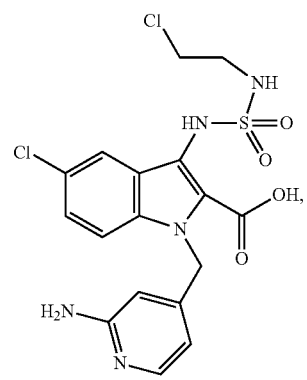

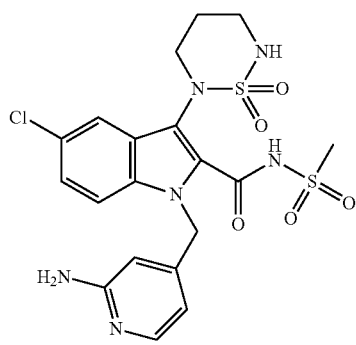

| 101 -continued | 102 -continued |
|---|---|
| 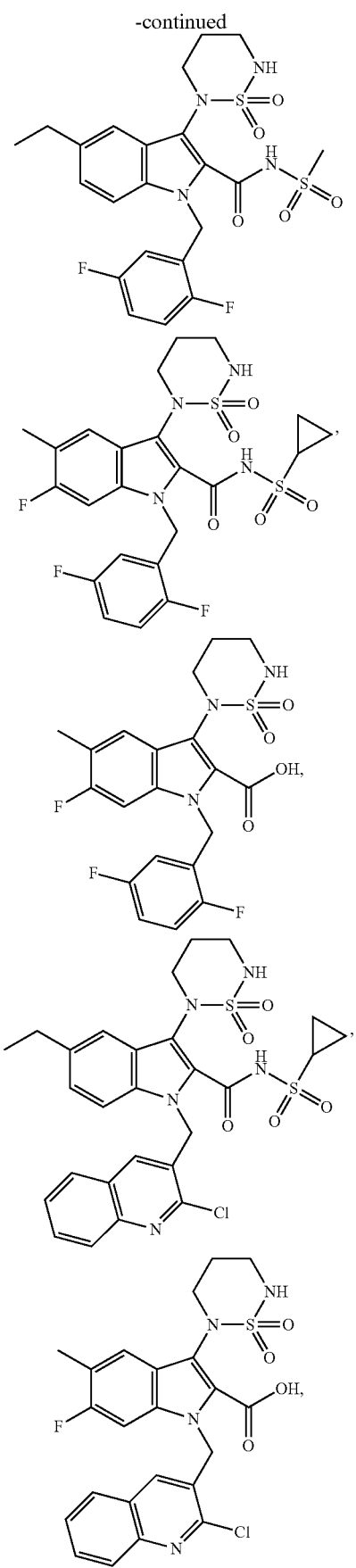 | 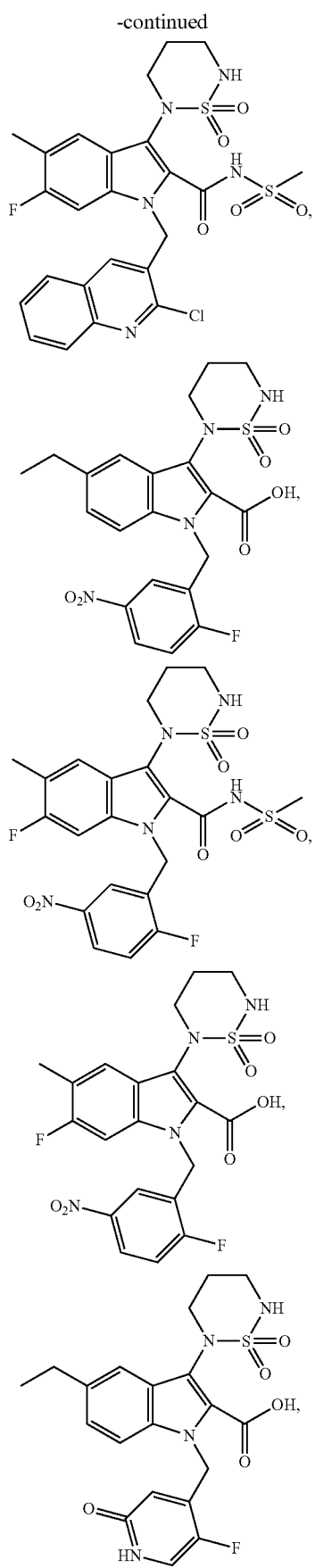 |

-continued
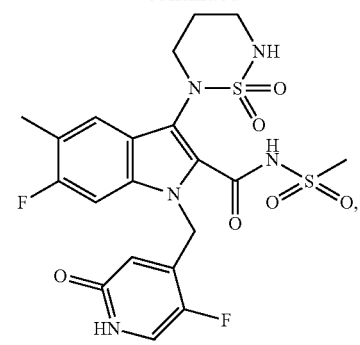
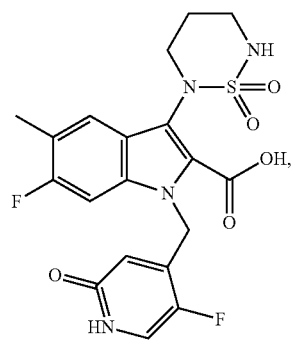
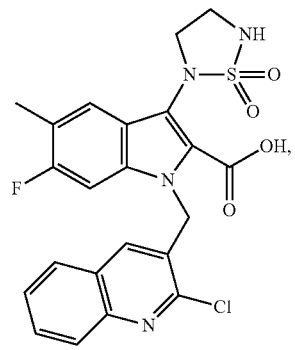
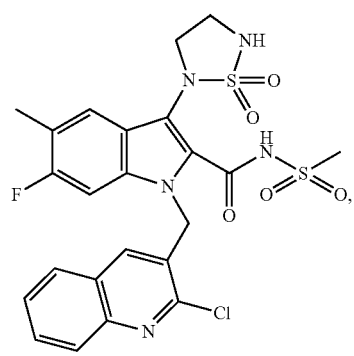
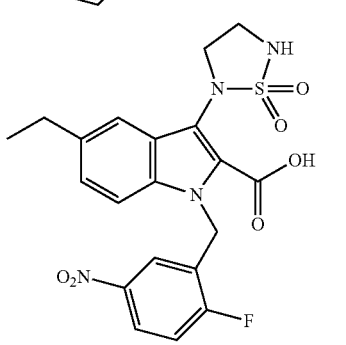
or
-continued
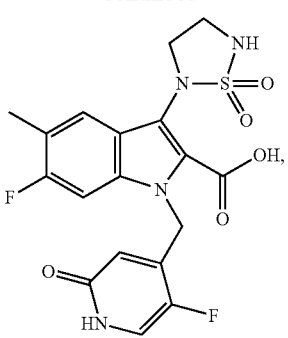
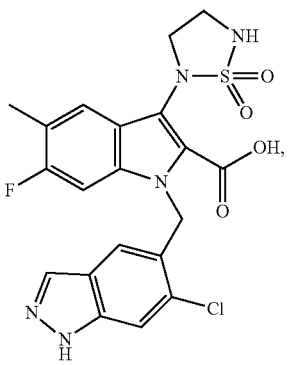
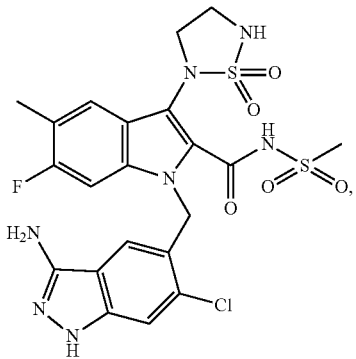
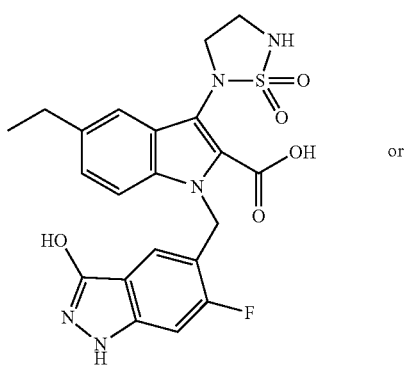
or

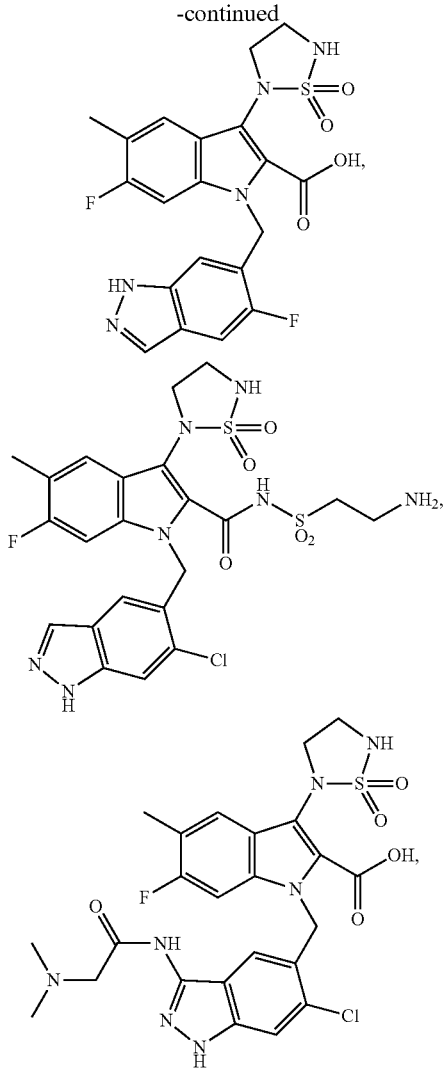
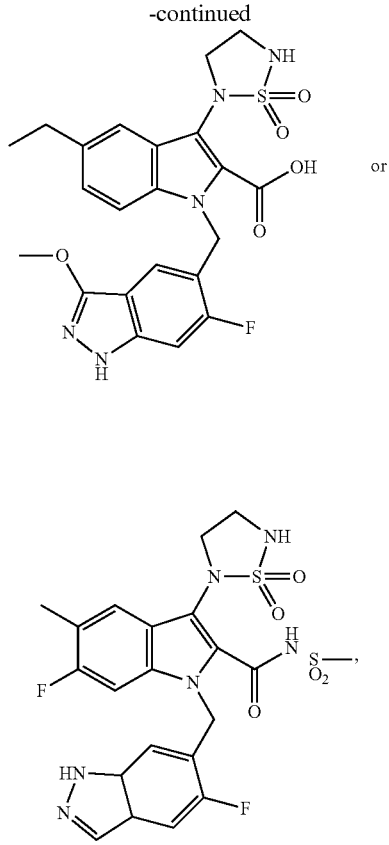
or a pharmaceutically acceptable salt thereof.
15. A composition comprising at least one compound of claim 1 or a pharmaceutically acceptable salt, and at least one pharmaceutically acceptable carrier.
\* \* \* \* \*